US012648911B2

(12) United States Patent
Koziara et al.

(10) Patent No.: US 12,648,911 B2
(45) Date of Patent: *Jun. 9, 2026

(54) PHARMACEUTICAL FORMULATIONS COMPRISING TENOFOVIR ALAFENAMIDE AND EMTRICITABINE

(71) Applicant: Gilead Sciences, Inc., Foster City, CA (US)

(72) Inventors: Joanna M. Koziara, Foster City, CA (US); Scott McCallister, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/464,945

(22) Filed: Jan. 30, 2026

(65) Prior Publication Data

US 2026/0151344 A1 Jun. 4, 2026

Related U.S. Application Data

(63) Continuation of application No. 19/048,549, filed on Feb. 7, 2025, which is a continuation of application No. 18/782,290, filed on Jul. 24, 2024, now abandoned, which is a continuation of application No. 18/539,583, filed on Dec. 14, 2023, now abandoned, (Continued)

(51) Int. Cl.

| | |
|---|---|
| ***A61K 9/20*** | (2006.01) |
| ***A61K 9/00*** | (2006.01) |
| ***A61K 9/24*** | (2006.01) |
| ***A61K 9/28*** | (2006.01) |
| ***A61K 31/513*** | (2006.01) |
| ***A61K 31/675*** | (2006.01) |

(52) U.S. Cl.

CPC .......... *A61K 9/2054* (2013.01); *A61K 9/0053* (2013.01); *A61K 9/2013* (2013.01); *A61K 9/209* (2013.01); *A61K 9/284* (2013.01); *A61K 9/2866* (2013.01); *A61K 31/513* (2013.01); *A61K 31/675* (2013.01)

(58) Field of Classification Search

CPC .. A61K 9/2054; A61K 9/0053; A61K 9/2013; A61K 9/209; A61K 9/284; A61K 9/2866; A61K 31/513; A61K 31/675

See application file for complete search history.

(56) References Cited

U.S. PATENT DOCUMENTS 5,914,331 A 6/1999 Liotta et al.
6,642,245 B1 11/2003 Liotta et al.
(Continued)

FOREIGN PATENT DOCUMENTS

WO WO 2002/008241 A2 1/2002
WO WO 2003/016306 A1 2/2003
(Continued)

OTHER PUBLICATIONS

U.S. Appl. No. 16/690,272, filed Nov. 21, 2019, Koziara et al.
(Continued)

*Primary Examiner* — Trevor Love
(74) *Attorney, Agent, or Firm* — Fish & Richardson P.C.

(57) ABSTRACT

The invention provides a solid oral dosage form comprising tenofovir alafenamide or a pharmaceutically acceptable salt thereof, and emtricitabine or a pharmaceutically acceptable salt thereof.

29 Claims, 14 Drawing Sheets

Related U.S. Application Data which is a continuation of application No. 18/204,012, filed on May 31, 2023, now abandoned, which is a continuation of application No. 17/984,290, filed on Nov. 10, 2022, now abandoned, which is a continuation of application No. 17/667,674, filed on Feb. 9, 2022, now abandoned, which is a continuation of application No. 17/386,089, filed on Jul. 27, 2021, now abandoned, which is a continuation of application No. 17/148,765, filed on Jan. 14, 2021, now abandoned, which is a continuation of application No. 16/923,139, filed on Jul. 8, 2020, now abandoned, which is a continuation of application No. 16/690,272, filed on Nov. 21, 2019, now abandoned, which is a continuation of application No. 15/197,491, filed on Jun. 29, 2016, now abandoned.

(60) Provisional application No. 62/317,286, filed on Apr. 1, 2016, provisional application No. 62/301,429, filed on Feb. 29, 2016, provisional application No. 62/298,373, filed on Feb. 22, 2016, provisional application No. 62/187,113, filed on Jun. 30, 2015.

(56) References Cited

U.S. PATENT DOCUMENTS

| | | | |
|---|---|---|---|
| 6,703,396 | B1 | 3/2004 | Liotta et al. |
| 6,838,464 | B2 | 1/2005 | Pease et al. |
| 7,067,522 | B2 | 6/2006 | Pease et al. |
| 7,125,879 | B2 | 10/2006 | Guillemont et al. |
| 7,176,220 | B2 | 2/2007 | Satoh et al. |
| 7,390,791 | B2 | 6/2008 | Becker et al. |
| 7,635,704 | B2 | 12/2009 | Satoh et al. |
| 7,803,788 | B2 | 9/2010 | Becker et al. |
| 8,080,551 | B2 | 12/2011 | Guillemont et al. |
| 8,101,629 | B2 | 1/2012 | Guillemont et al. |
| 8,148,374 | B2 | 4/2012 | Desai et al. |
| 8,592,397 | B2 | 11/2013 | Dahl et al. |
| 8,598,185 | B2 | 12/2013 | Dahl et al. |
| 8,633,219 | B2 | 1/2014 | Matsuzaki et al. |
| 8,716,264 | B2 | 5/2014 | Dahl et al. |
| 8,754,065 | B2 | 6/2014 | Liu et al. |
| 8,981,103 | B2 | 3/2015 | Ando et al. |
| 9,018,192 | B2 | 4/2015 | Dahl et al. |
| 9,044,509 | B2 | 6/2015 | Heneine et al. |
| 9,216,996 | B2 | 12/2015 | Jin et al. |
| 9,296,769 | B2 | 3/2016 | Liu et al. |
| 9,457,036 | B2 | 10/2016 | Dahl et al. |
| 9,545,414 | B2 | 1/2017 | Dahl et al. |
| 9,663,528 | B2 | 5/2017 | Desai et al. |
| 9,682,084 | B2 | 6/2017 | Carra et al. |
| 9,708,342 | B2 | 7/2017 | Carra et al. |
| 9,732,092 | B2 | 8/2017 | Jin et al. |
| 9,744,181 | B2 | 8/2017 | Dahl et al. |
| 9,891,239 | B2 | 2/2018 | Desai et al. |
| 2004/0224916 | A1 | 11/2004 | Dahl et al. |
| 2007/0077295 | A1 | 4/2007 | Dahl et al. |
| 2007/0219243 | A1 | 9/2007 | Kearney et al. |
| 2013/0243857 | A1 | 9/2013 | Oliyai et al. |
| 2014/0246719 | A1 | 9/2014 | Dhaoui et al. |
| 2014/0296266 | A1 | 10/2014 | Hu et al. |
| 2015/0111856 | A1 | 4/2015 | Dahl et al. |
| 2017/0000807 | A1 | 1/2017 | Koziara et al. |
| 2017/0027967 | A1 | 2/2017 | Koziara et al. |
| 2017/0057976 | A1 | 3/2017 | Jin et al. |
| 2017/0079999 | A1 | 3/2017 | Dahl et al. |
| 2017/0114074 | A1 | 4/2017 | Jin et al. |
| 2017/0136000 | A1 | 5/2017 | Kearney et al. |
| 2018/0177734 | A1 | 6/2018 | Koziara et al. |
| 2025/0281412 | A1 | 9/2025 | Koziara et al. |

FOREIGN PATENT DOCUMENTS

| | | | |
|---|---|---|---|
| WO | WO 2004/024078 | A2 | 3/2004 |
| WO | WO 2004/064845 | A1 | 8/2004 |
| WO | WO 2004/064846 | A1 | 8/2004 |
| WO | WO 2006/030807 | A1 | 3/2006 |
| WO | WO 2006/116764 | A1 | 11/2006 |
| WO | WO 2006/135933 | A2 | 12/2006 |
| WO | WO 2009/135179 | A2 | 11/2009 |
| WO | WO 2010/091197 | A2 | 8/2010 |
| WO | WO 2011/035231 | A1 | 3/2011 |
| WO | WO 2012/068535 | A1 | 5/2012 |
| WO | WO 2013/025788 | A1 | 2/2013 |
| WO | WO 2013/116720 | A1 | 8/2013 |
| WO | WO 2014/184553 | A1 | 11/2014 |
| WO | WO 2015/022351 | A1 | 2/2015 |
| WO | WO 2015/030853 | A1 | 5/2015 |
| WO | WO 2015/085976 | A1 | 6/2015 |
| WO | WO 2015/196116 | A1 | 12/2015 |
| WO | WO 2017/004244 | A1 | 1/2017 |

OTHER PUBLICATIONS

U.S. Appl. No. 16/923,139, filed Jul. 8, 2020, Koziara et al.
U.S. Appl. No. 17/148,765, filed Jan. 14, 2021, Koziara et al.
U.S. Appl. No. 17/386,089, filed Jul. 27, 2021, Koziara et al.
U.S. Appl. No. 17/667,674, filed Feb. 9, 2022, Koziara et al.
U.S. Appl. No. 17/984,290, filed Nov. 10, 2022, Koziara et al.
U.S. Appl. No. 18/204,012, filed May 31, 2023, Koziara et al.
U.S. Appl. No. 18/539,583, filed Jul. 24, 2024, Koziara et al.
U.S. Appl. No. 18/782,290, filed Jul. 24, 2024, Koziara et al.
U.S. Appl. No. 19/451,093, filed Jan. 16, 2026, Koziara et al.
U.S. Appl. No. 19/451,185, filed Jan. 16, 2026, Koziara et al.
U.S. Appl. No. 19/461,014, filed Jan. 27, 2026, Koziara et al.
U.S. Appl. No. 19/545,594, filed Feb. 20, 2026, Koziara et al.
[No Author Listed], "Assessment report: Genvoya," European Medicines Agency, Sep. 24, 2015, 159 pages.
[No Author Listed], "European Medicines Agency Validates Gilead's Marketing Application for Fixed-Dose Combination of Emtricitabine and Tenofovir Alafenamide for HIV Treatment," Business Wire, May 28, 2015, 2 pages.
[No Author Listed], "Highlights of Prescribing Information: ODEFSEY," Gilead Sciences, Mar. 2016, 42 pages.
[No Author Listed], "Truvada 200 mg/245 mg film-coated tablets: Summary of Product Characteristics," Gilead Sciences Ltd, dated Sep. 11, 2020, 59 pages.
[The Tablet], 2nd ed., Ritschel et el. (eds.), 2002, pp. 64-65 (with machine translation).
Anonymous, "A Clinical Overview of Tenofovir Alafenamide," The Body PRO: The HIV Resource for Health Professionals, May 23, 2013, 3 pages.
Astuti et al., "Single-Tablet Regimens in HIV Therapy," Infect Dis Ther, Jun. 2014, 3(1): 1-17.
Bastin et al., "Salt Selection and Optimisation Procedures for Pharmaceutical New Chemical Entities," Organic Process Research and Development, Jul. 19, 2000, 4(5):427-435.
Berge et al., "Pharmaceutical Salts," J. Pharma Sci., 1977, 66(1): 1-19.
Brittain, "Overview of the Solid Dosage Form Preformulation Program," Preformulation in Solid Dosage Form Development, CRC Press, Jan. 2008, Chapter 4.1, pp. 347-355.
Buckley, "Desiccants for Pharmaceutical Applications," Pharmaceutical Technology Europe, Jan. 2005, 16-19.
ClinicalTrials.gov [online], "History of Changes for Study: NCT01797445; Study to Evaluate the Safety and Efficacy of Elvitegravir/CobicistaUEmtricitabine/Tenofovir Alafenamide Versus Elvitegravir/CobicistaUEmtricitabine/ Tenofovir Disoproxil Fumarate in HIV-1 Positive, Antiretroviral Treatment-Naive Adults," NCT01797445, Feb. 18, 2020, retrieved on Dec. 11, 2023, retrieved from URL <https://classic.clinicaltrials.gov/ct2/history/NCT01797445>, 22 pages.
ClinicalTrials.gov [online], "History of Changes for Study: NCT01815736; Open-Label Study to Evaluate Switching From a TDF-Containing Combination Regimen to a T AF-Containing Com-

(56) References Cited

OTHER PUBLICATIONS bination Single Tablet Regimen (STR) in Virologically-Suppressed, HIV-1 Positive Subjects," NCT01815736, Mar. 22, 2021, retrieved on Dec. 11, 2023, retrieved from URL <https://classic.clinicaltrials.gov/ct2/history/NCT01815736>, 26 pages.
ClinicalTrials.gov [online], "History of Changes for Study: NCT02345252; Switch Study to Evaluate the Safety and Efficacy of Emtricitabine/Rilpivirine/Tenofovir Alafenamide (FTC/RPV/TAF) Fixed Dose Combination (FDC) in HIV-1 Positive Adults Who Are Virologically Suppressed on Emtricitabine/Rilpivirine/Tenofovir Disoproxil Fumarate (FTC/RPV/TDF)," Dec. 16, 2019, retrieved on Jun. 2, 2025, retrieved from URL <https://classic.clinicaltrials.gov/ct2/history/NCT02345252>, 30 pages.
Coffey, "Comparison of 2 Tenofovir Prodrugs: TAF (GS 7340) and TDF," AETC: National Coordinating Resource Center, May 2013, retrieved on Jun. 14, 2018, URL <https://aidsetc.org/blog/comparison-2-tenofovir-prodrugs-taf-gs-7340-and-tdf>, 3 pages.
Collins, "Pipeline ART: tenofovir alafenamide (TAF)" HIV Treatment Bulletin, Mar. 24, 2015, [retrieved on Aug. 27, 2018], URL <http://i-base.info/htb/27932, 4 pages.
Costagliola, "Demographics of HIV and aging," Curr. Opin. HIV AIDS, Jul. 2014, 9(4): 294-301.
Cunningham et al., "Formulation of acetylsalicylic acid tablets for aqueous enteric film coating," Pharmaceutical Technology, Sep. 2001, 25(9):38-43.
Du et al., "The Influence of Excipients on the Stability of the Moisture Sensitive Drugs Aspirin and Niacinamide: Comparison of Tablets Containing Lactose Monohydrate with Tablets Containing Anhydrous Lactose," Pharmaceutical Development and Technology, Apr. 30, 2001, 6(2):159-166.
EMEA [online], "Guideline on the Investigation of Bioequivalence," EMA.Europa.eu, Jan. 2010, retrieved on Jun. 14, 2018, URL <http://www.ema.europa.eu/docs/en_GB/document_library/Scientific_guideline/2010/01/WC500070039.pdf>, 27 pages.
FDA.gov [online], Guidance for Industry: Bioavailability and Bioequivalence Studies for Orally Administered Drug Products—General Considerations,: FDA, Jul. 2002, retrieved on Jun. 14, 2018, URL <https://www.fda.gov/downloads/Drugs/Guidances/ucm154838>, 27 pages.
Gilead.com [online] "European Medicines Agency Validates Gilead's Marketing Application for Fixed-Dose Combination of Emtricitabine and Tenofovir Alafenamide for HIV Treatment," May 28, 2015, retrieved on Sep. 1, 2025, retrieved from URL <https://www.gilead.com/news/news-details/2015/european-medicines-agency-validates-gileads-marketing-application-for-fixed-dose-combination-of-emtricitabine-and-tenofovir-alafenamide-for-hiv-treatment>, 2 pages.
Gilead.com [online] "Gilead Discontinues Development of GS 9005 and GS 7340; Company Continues Commitment to Research Efforts in HIV," Oct. 21, 2004, retrieved on Sep. 3, 2025, retrieved from URL <https://www.gilead.com/news/news-details/2004/gilead-discontinues-development-of-gs-9005-and-gs-7340-company-continues-commitment-to-research-efforts-in-hiv>, 1 page.
Gilead.com [online] "Gilead Submits New Drug Application to U.S. Food and Drug Administration for Fixed-Dose Combination of Emtricitabine/Tenofovir Alafenamide for HIV Treatment," Apr. 7, 2015, retrieved on Sep. 16, 2022, retrieved from URL <https://www.gilead.com/news-and-press/press-room/press-releases/2015/4/gilead-submits-new-drug-application-to-us-food-and-drug-administration-for-fixeddose-combination-of-emtricitabinetenofovir-alafenamide-for-hiv-tre>, 2 pages.
Markowitz et al, "Phase I/II study of the pharmacokinetics, safety and antiretroviral activity of tenofovir alafenamide, a new prodrug of the HIV reverse transcriptase inhibitor tenofovir, in HIV-infected adults," Journal of Antimicrobial Chemotherapy, 2014, 69:(5):1362-1369.
Martinez [online], "CROI 2012: El nuevo profármaco de tenofovir muestra una eficacia superior a la formulación actual en un pequeño estudio (CROI 2012: The new prodrug of tenofovir shows superior efficacy to the current formulation in a small study)," Mar. 23, 2012,[retrieved on Mar. 4, 2019] URL <http://gtt-vih.org/actualizate/la_noticia_del_dia/22-03-12>, 4 pages (with English translation).
Mihranyan et al., "Moisture sorption by cellulose powders of varying crystallinity," International Journal of Pharmaceutics, Jan. 28, 2004, 269(2):433-442.
Murakami et al., "Implications of Efficient Hepatic Delivery by Tenofovir Alafenamide (GS-7340) for Hepatitis B Virus Therapy." Antimicrob Agents Chemother, Jun. 2015, 59(6): 3563-3569, doi: 10.1128/AAC.00128.15.
Narang et al., "Impact of Excipient Interactions on Solid Dosage Form Stability," Pharmaceutical Research, Jun. 16, 2012, 29(10):2660-2683.
Niazi, Handbook of Pharmaceutical Manufacturing Formulations: Compressed solid products, 2nd Ed., vol. 1, Informa Healthcare, 2009, p. 314 and 315.
Niazi, Handbook of Pharmaceutical Manufacturing Formulations: Compressed solid products, 2nd Ed., vol. 1, Informa Healthcare, 2009, pp. 203 and 250.
Niazi, Handbook of Pharmaceutical Manufacturing Formulations: Compressed solid products, 2nd Ed., vol. 1, Informa Healthcare, 2009, pp. 218 and 379.
Niazi, Handbook of Pharmaceutical Manufacturing Formulations: Compressed solid products, 2nd Ed., vol. 1, Informa Healthcare, 2009, pp. 242 and 449.
Pharmaceutics: The Science of Dosage Form Design, 2nd ed., Aulton (ed.), 2002, pp. 128-131.
Ruane et al., "Antiviral Activity, Safety, and Pharmacokinetics/Pharmacodynamics of Tenofovir Alafenamide as 10-Day Monotherapy in HIV-1-Positive Adults," Journal of Acquired Immune Deficiency Syndromes, Aug. 1, 2013, 63(4):449-455.
Saag, "Emtricitabine, a new antiretroviral agent with activity against HIV and hepatitis B virus," Clinical Infectious Diseases, Jan. 1, 2006, 42(1):126-13.
Sax et al., "Tenofovir alafenamide vs. tenofovir disoproxil fumarate in single tablet regimens for initial HIV-1 therapy: a randomized phase 2 study," Journal of Acquired Immune Deficiency Syndromes, Sep. 1, 2014, 67(1):52-58.
Sax et al., "Tenofovir alafenamide versus tenofovir disoproxil fumarate, coformulated with elvitegravir, cobicistat, and emtricitabine, for initial treatment of HIV-1 infection: two randomised, double-blind, phase 3, non-inferiority trials," Lancet, Jun. 2015, 385:2606-2615.
Telaprolu et al., "A Review on Pharmaceutical Excipients," International Journal of Research in Pharmaceutical and Nano Sciences, Jul./Aug. 2013, 2(4):423-431.
Truvada TM FDA label approval. NDA 21-752 from Aug. 2, 2014, pp. 6-56.
Administrative Judgment in CN Appln. No. 201680045136.1, mailed on Sep. 29, 2024, 23 pages (with English translation).
AU Examination Report No. 1 in Australia Appln. No. 2016287500, dated May 8, 2018, 5 pages.
AU Examination Report No. 1 in Australian Appln. No. 2016285916, dated May 15, 2018, 3 pages.
Australia Office Action in AU Appln. No. 2021202009, mailed on Apr. 13, 2022, 3 pages.
Australian Office Action in AU Appln. No. 2019210558, dated Apr. 3, 2020, 3 pages.
Chinese Office Action in CN Appln. No. 201680045136.1, dated Aug. 17, 2020, 17 pages (with English translation).
Chinese Office Action in CN Appln. No. 201680045136.1, mailed on Jan. 10, 2023, 13 pages (with English translation).
Chinese Office Action in CN Appln. No. 201680045136.1, mailed on Jun. 23, 2021, 11 pages (with English translation).
CL Opposition, *Laboratorio Bamberg Limitada* v. *Gilead Sciences, INC.* in CL Appln. No. 3320-2017, dated Sep. 14, 2018, 28 pages (with translated summary).
CO Office Action in Colombia Appln. No. NC2017/0013293, dated Jan. 2, 2018, 4 pages (with English Translation).
CO Opposition Official Letter No. 493 in Colombian Appln. No. NC2017/0013293, dated Dec. 17, 2018, 12 pages.
CO Opposition Official Letter No. 530 in Colombian Appln. No. NC2017/0013293, dated Dec. 17, 2018, 29 pages.

(56) References Cited

OTHER PUBLICATIONS

Colombian Office Action in CO Appln. No. NC2017/0013293, dated Dec. 7, 2020, 30 pages (with English translation).
Colombian Office Action in CO Appln. No. NC2017/0013293, dated Jun. 24, 2020, 27 pages (with English translation).
Colombian Office Action in CO Appln. No. NC2017/0013293, mailed on Mar. 2, 2021, 9 pages (with English translation).
CU Office Action in Cuba Appln. No. 2017-0168, dated Feb. 9, 2018, 4 pages.
Decision in Opposition Proceedings against European Patent No. 4070787, mailed on Feb. 20, 2025, 33 pages.
Decision in Opposition Proceedings against European Patent No. 4070788, mailed on Feb. 21, 2025, 33 pages.
DO Office Action in Dominican Republic Appln. No. P2017-0306, dated Apr. 4, 2018, 7 pages (with English Translation).
EC Opposition, "*Formulaciones Farmaceuticas* v. *Gilead Sciences, INC*." in Ecuadorian Appln. No. IEPI-2017-84331, dated Dec. 3, 2018, 11 pages (with translated summary).
EPO Communication pursuant to Rules 161 and 162 in European Application No. 16739321, dated Feb. 22, 2018, 3 pages.
European Office Action in EP Application No. 16739625.8, mailed on Jul. 9, 2019, 5 pages.
European Office Action in EP Appln. No. 19199257.7, mailed on Mar. 3, 2021, 3 pages.
European Office Action in EP Appln. No. 22176524.1, mailed on Sep. 15, 2022, 5 pages.
Extended European Search Report in EP Appln. No. 19199257.7, mailed on Dec. 17, 2019, 8 pages.
Extended European Search Report in EP Appln. No. 23162978.3, mailed on Aug. 31, 2023, 7 pages.
Extended European Search Report in EP Appln. No. 24216441.6, mailed on Apr. 23, 2025, 10 pages.
Japanese Office Action in JP Application No. 2020-029330, mailed on Dec. 11, 2020, 3 pages (with English translation).
Japanese Office Action in JP Application No. 2020-029330, mailed on Jun. 4, 2021, 5 pages (with English translation).
Japanese Office Action in JP Appln. No. 2021-142184, mailed on Aug. 15, 2022, 5 pages (with English translation).
JP Office Action in Japanese Appln. No. 2017-566409, dated Nov. 1, 2018, 17 pages (with English Translation).
JP Office Action in Japanese Appln. No. 2017-568191, dated Nov. 1, 2018, 7 pages (with English Translation).
Korean Office Action in KR Appln. No. 10-2018-7002382, dated Jan. 2, 2020.
Notice of Oppoisition against IN Patent No. 397784, mailed on Jul. 19, 2024, 28 pages.
Notice of Opposition against EP Patent No. 4070787, filed Dec. 11, 2023, 15 pages.
Notice of Opposition against EP Patent No. 4070788, filed Dec. 11, 2023, 15 pages.
Notice of Opposition in EP Appln. No. 23162978.3, filed on Sep. 1, 2025, 16 pages.
Notice of Opposition in EP Appln. No. 23162978.3, filed on Sep. 3, 2025, 25 pages.
Notice of Opposition in EP Appln. No. 23162978.3, filed on Sep. 4, 2025, 12 pages.
NZ First Examination Report in New Zealand Appln. No. 738524, dated May 17, 2018, 4 pages.
NZ First Examination Report in New Zealand Appln. No. 738533, dated May 17, 2018, 5 pages.
NZ Office Action issued in New Zealand Appln. No. 738533, dated Jan. 30, 2019, 4 pages.
PA Notification 81 Communication in Panama Appln. No. PI/2017/91917-01, dated Feb. 6, 2018, 3 pages (with English translation).
PCT International Preliminary Report on Patentability in International Appln. No. PCT/US2016/040158, dated Jan. 2, 2018, 8 pages.
PCT International Search Report and Written Opinion in International Appln. No. PCT/US2016/039762, dated Sep. 9, 2016, 9 pages.
PCT International Search Report in International Appln. No. PCT/US2016/040158, dated Sep. 26, 2016, 4 pages.
PCT Preliminary Report on Patentability in International Appln. No. PCT/US2016/039762, dated Jan. 2, 2018, 6 pages.
Reexamination Decision in CN Appln. No. 201680045136.1, mailed on May 26, 2023, 30 pages (with English translation).
Summons to Attend Oral Proceedings in EP Appln. No. 22176524.1, mailed on Jul. 4, 2024, 25 pages.
Summons to Attend Oral Proceedings in EP Appln. No. 22176537.3, mailed on Jul. 4, 2024, 25 pages.
Supplementary European Search Report in EP Appln. No. 22176524.1, mailed on Aug. 29, 2022, 6 pages.
Supplementary European Search Report in EP Appln. No. 22176537.3, mailed on Aug. 26, 2022, 6 pages.
VN Office Action issued in Vietnam Appln. No. 1-2018-00239, dated Feb. 13, 2018, 4 pages (with English translation).

PHARMACEUTICAL FORMULATIONS COMPRISING TENOFOVIR ALAFENAMIDE AND EMTRICITABINE

TECHNICAL FIELD

Pharmaceutical formulations suitable for treating viral infections such as HIV are disclosed, in particular solid oral dosage forms including emtricitabine and tenofovir alafenamide. Pharmaceutical formulations suitable for treating viral infections such as HIV, and in particular solid oral dosage forms including rilpivirine, emtricitabine and tenofovir alafenamide, are also disclosed.

BACKGROUND

Human immunodeficiency virus, type 1 (HIV-1) infection is a life-threatening and serious disease of major public health significance, with approximately 35 million people infected worldwide (Joint United Nations Programme on HIV/AIDS (UNAIDS). Global report: UNAIDS report on the global AIDS epidemic, 2013). Standard of care for the treatment of HIV-1 infection uses combination antiretroviral therapy (ART) to suppress viral replication to below detectable limits, increase CD4 cell counts, and halt disease progression.

The success of potent and well-tolerated ART means that morbidity and mortality in the HIV-infected population is increasingly driven by non-AIDS associated comorbidities. Clinical attention has become more focused on optimizing tolerability, long-term safety, and adherence (Costagliola D. Demographics of HIV and aging. *Curr. Opin. HIV AIDS,* 2014, 9 (4), 294). There remains a significant medical need for safe and effective new therapies that take into consideration the aging patient population, non-HIV-related comorbidities, virologic resistance, and regimen simplification.

SUMMARY

The inventors have successfully formulated an oral dosage form containing tenofovir alafenamide and emtricitabine. This oral dosage form may be suitable for use in medicine, and in particular in treating viral infections such as HIV.

The inventors have found that it is possible to formulate solid oral dosage forms that are intended to be pharmaceutically acceptable (i.e. pharmacologically efficacious and physically acceptable) while reducing the total amount of excipients necessary to achieve stability. Accordingly, in one aspect the invention provides a solid oral dosage form comprising 25 mg tenofovir alafenamide or a pharmaceutically acceptable salt thereof, and 200 mg emtricitabine or a pharmaceutically acceptable salt thereof, wherein the dosage form has a total weight of less than 850 mg (e.g. less than 800 mg or less than 700 mg). In a further aspect a solid oral dosage form comprising 25 mg tenofovir alafenamide or a pharmaceutically acceptable salt thereof, and 200 mg emtricitabine or a pharmaceutically acceptable salt thereof is provided, wherein the dosage form has a total weight of less than 500 mg (e.g. less than 400 mg). In another aspect a solid oral dosage form comprising 10 mg tenofovir alafenamide, or a pharmaceutically acceptable salt thereof, and 200 mg emtricitabine or a pharmaceutically acceptable salt thereof, is provided, wherein the dosage form has a total weight of less than 850 mg (e.g. less than 800 mg or less than 700 mg). In a further aspect a solid oral dosage form comprising 10 mg tenofovir alafenamide or a pharmaceutically acceptable salt thereof, and 200 mg emtricitabine or a pharmaceutically acceptable salt thereof is provided, wherein the dosage form has a total weight of less than 500 mg (e.g. less than 400 mg).

In one embodiment, the oral dosage form is a tablet. In some embodiments, the dosage forms and tablets of the invention will contain two (and only two) active pharmaceutical ingredients: tenofovir alafenamide or a pharmaceutically acceptable salt thereof and emtricitabine or a pharmaceutically acceptable salt thereof.

The inventors have demonstrated that it is possible to formulate stable compositions containing tenofovir alafenamide and emtricitabine that exhibit acceptable stability. Accordingly, in another aspect the invention provides a composition comprising (a) tenofovir alafenamide or a pharmaceutically acceptable salt thereof, and (b) emtricitabine or a pharmaceutically acceptable salt thereof, where the total quantity of degradation products derived from the tenofovir alafenamide or the pharmaceutically acceptable salt thereof is less than 3% after storage for one month at 40° C./75% RH in open conditions. Such compositions may further comprise rilpivirine or a pharmaceutically acceptable salt thereof.

The inventors have also found that there is a relationship between the stability of tenofovir alafenamide and the concentration of tenofovir alafenamide within a given composition. Accordingly, in another aspect the invention provides a solid composition comprising tenofovir alafenamide or a pharmaceutically acceptable salt thereof wherein the proportion of tenofovir alafenamide or a pharmaceutically acceptable salt thereof in the composition is from about 2.5% to about 12% by weight. Another aspect provides a solid composition comprising tenofovir alafenamide or a pharmaceutically acceptable salt thereof wherein the proportion of tenofovir alafenamide or a pharmaceutically acceptable salt thereof in the composition is from about 4% to about 12% by weight. Another aspect provides a solid composition comprising from about 5% to about 15% by weight tenofovir alafenamide hemifumarate. Another aspect provides a solid composition comprising from about 2% to about 4% by weight tenofovir alafenamide hemifumarate.

In another aspect, a dry granulated mixture of (a) tenofovir alafenamide or a pharmaceutically acceptable salt thereof, and (b) emtricitabine or a pharmaceutically acceptable salt thereof is provided.

In another aspect, a kit comprising (a) a tablet comprising tenofovir alafenamide or a pharmaceutically acceptable salt thereof, and emtricitabine or a pharmaceutically acceptable salt thereof, and (b) a desiccant (e.g. silica gel) is provided. In another aspect, a kit comprising (a) a tablet comprising tenofovir alafenamide or a pharmaceutically acceptable salt thereof, and emtricitabine or a pharmaceutically acceptable salt thereof, and (b) a desiccant (e.g. silica gel) is provided, wherein the total quantity of degradation products derived from the tenofovir alafenamide or the pharmaceutically acceptable salt thereof is less than 2% after storage for twelve months at 30° C./75% RH. In another aspect, a kit comprising (a) a tablet comprising tenofovir alafenamide or a pharmaceutically acceptable salt thereof, and emtricitabine or a pharmaceutically acceptable salt thereof, and (b) a desiccant (e.g. silica gel) is provided, wherein the total quantity of degradation products derived from the tenofovir alafenamide or the pharmaceutically acceptable salt thereof is less than 2.5% after storage for three months at 40° C./75% RH.

Methods of producing solid oral dosage forms such as tablets are also provided, as discussed in more detail below.

In addition, methods for treating patients are provided, which are also discussed in more detail below.

BRIEF DESCRIPTION OF DRAWINGS

FIG. 3A shows the total degradation of tenofovir alafenamide hemifumarate at 40° C./75% RH under open conditions.

DETAILED DESCRIPTION

Figure 1:
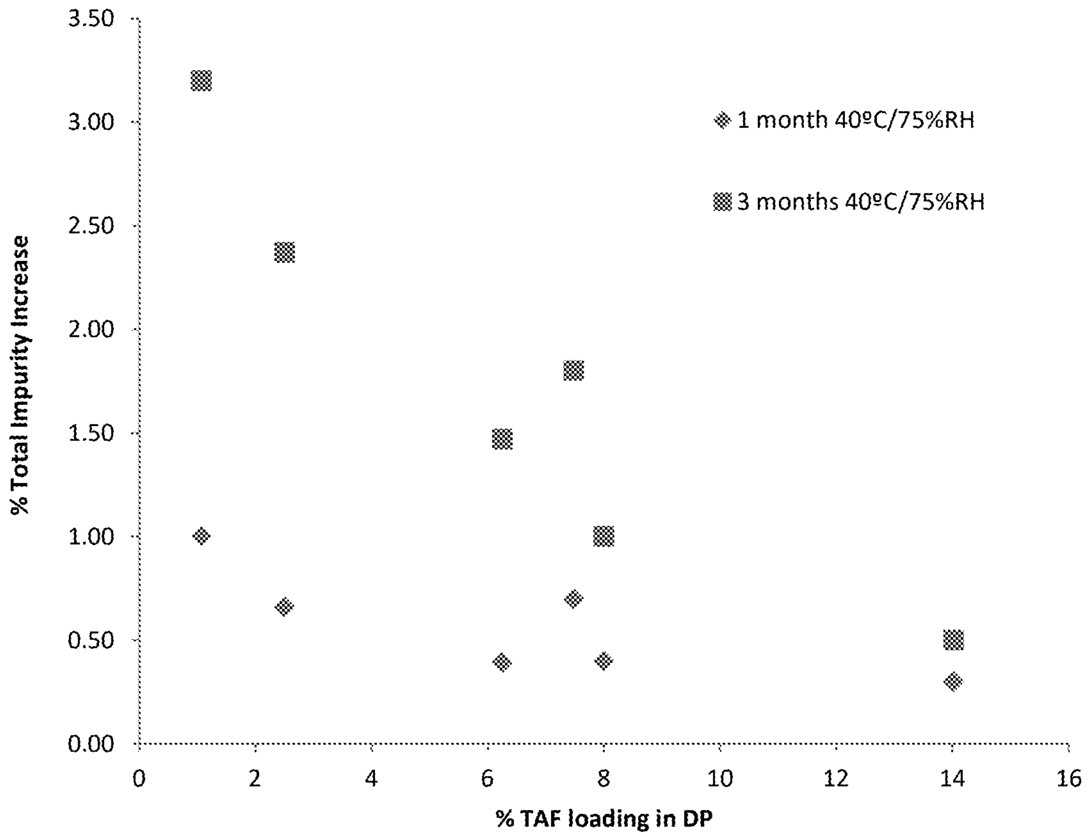
FIG. 1 shows the percent of degradation of tenofovir alafenamide hemifumarate as a function of drug load.

In some embodiments, the oral dosage forms disclosed herein comprise three active pharmaceutical ingredients: rilpivirine (or a pharmaceutically acceptable salt thereof), tenofovir alafenamide (or a pharmaceutically acceptable salt thereof), and emtricitabine (or a pharmaceutically acceptable salt thereof). In some embodiments, the oral dosage forms consist of two (i.e. only two) active pharmaceutical ingredients: tenofovir alafenamide (or a pharmaceutically acceptable salt thereof), and emtricitabine (or a pharmaceutically acceptable salt thereof).

Rilpivirine

Rilpivirine (R or RPV), a diarylpyrimidine derivative, is a potent non-nucleoside reverse transcriptase inhibitor (NNRTI) with in vitro activity against wild type HIV-1 and NNRTI-resistant mutants. It has the following formula (see WO2003/016306):

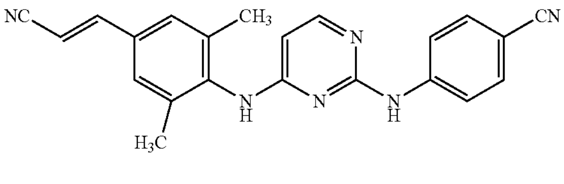 [SMILES: Cc1cc(/C=C/C#N)cc(C)c1Nc1ccnc(Nc2ccc(C#N)cc2)n1]

Its IUPAC name is 4-{[4-({4-[(E)-2-cyanoethenyl]-2,6-dimethylphenyl}amino)pyrimidin-2-yl]amino}benzonitrile. It is currently authorised as part of EDURANT® (rilpivirine HCl 27.5 mg, equivalent to 25 mg rilpivirine) and COMPLERA®/EVIPLERA® (rilpivirine HCl 27.5 mg, tenofovir disoproxil fumarate 300 mg, 200 mg emtricitabine).

Solid oral dosage forms disclosed herein include rilpivirine, usually in the form of a pharmaceutically acceptable salt. Rilpivirine can be present within an oral dosage form in solvated or unsolvated form, and references to "rilpivirine" include both of these forms. Typically, rilpivirine is in the form of rilpivirine HCl, having the formula below:

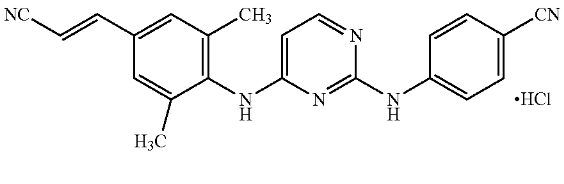 [SMILES: Cc1cc(/C=C/C#N)cc(C)c1Nc1ccnc(Nc2ccc(C#N)cc2)n1 ; Cl]

In certain specific embodiments, solid oral dosage forms containing 25 mg of rilpivirine, e.g. as about 27.5 mg of rilpivirine HCl, are provided.

As used herein, and in the absence of a specific reference to a particular pharmaceutically acceptable salt and/or solvate of rilpivirine (e.g. rilpivirine hydrochloride), any dosages, whether expressed in e.g. milligrams or as a % by weight, should be taken as referring to the amount of rilpivirine free base, i.e. the amount of:

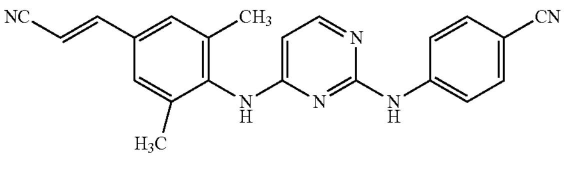 [SMILES: Cc1cc(/C=C/C#N)cc(C)c1Nc1ccnc(Nc2ccc(C#N)cc2)n1]

For example, therefore, a reference to "25 mg rilpivirine or a pharmaceutically acceptable salt and/or solvate thereof" means an amount of rilpivirine or a pharmaceutically acceptable salt and/or solvate thereof which provides the same amount of rilpivirine as 25 mg of rilpivirine free base.

Tenofovir Alafenamide

Tenofovir alafenamide (TAF) is a nucleotide reverse transcriptase inhibitor having the formula below (see WO02/08241 A2):

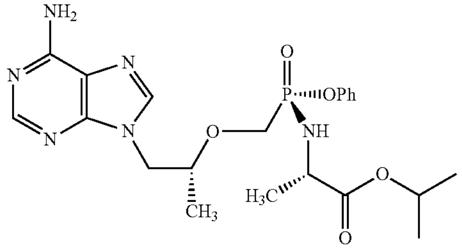 [SMILES: CC(C)OC(=O)[C@H](C)N[P@](=O)(CO[C@H](C)Cn1cnc2c(N)ncnc21)Oc1ccccc1]

Its IUPAC name is(S)-isopropyl-2-(((S)-((((R)-1-(6-amino-9H-purin-9-yl)propan-2-yl)oxy)methyl)(phenoxy)phosphoryl)amino)propanoate. It is also referred to as {9-[(R)-2-[[(S)-[[(S)-1-(isopropoxycarbonyl)ethyl] amino] phenoxyphosphinyl]-methoxy]propyl]adenine}.

Solid oral dosage forms of the invention include tenofovir alafenamide, usually in the form of a pharmaceutically acceptable salt. Tenofovir alafenamide can be present within an oral dosage form in solvated or unsolvated form, and references to "tenofovir alafenamide" include both of these forms. In particular, tenofovir alafenamide may be associated with fumarate, such as monofumarate or hemifumarate. Typically, tenofovir alafenamide is in the form of tenofovir alafenamide hemifumarate having the formula below (see WO 2013/025788 A1):

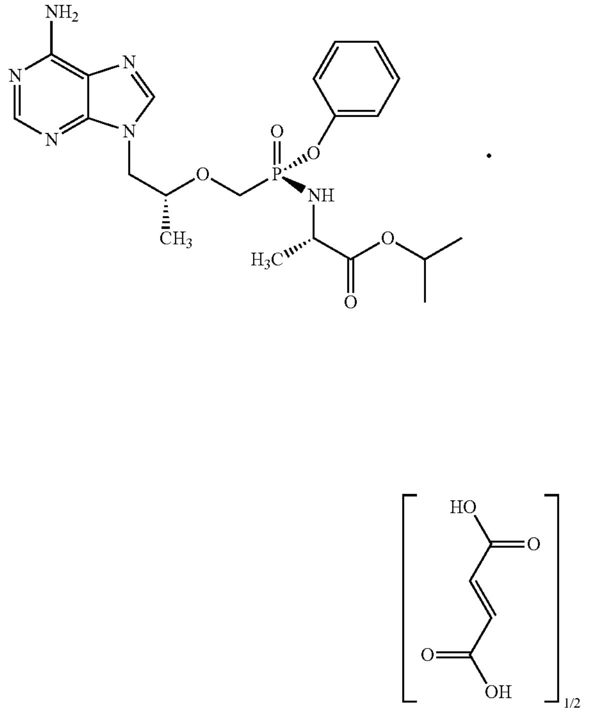

As used herein, and in the absence of a specific reference to a particular pharmaceutically acceptable salt and/or solvate of tenofovir alafenamide, any dosages, whether expressed in e.g. milligrams or as a % by weight, should be taken as referring to the amount of tenofovir alafenamide, i.e. the amount of:

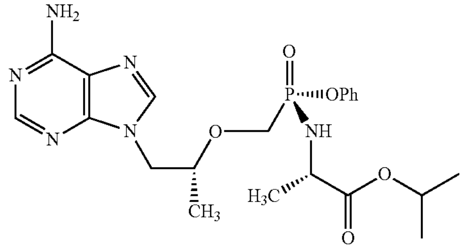 [SMILES: CC(C)OC(=O)[C@H](C)N[P@](=O)(CO[C@H](C)Cn1cnc2c(N)ncnc21)Oc1ccccc1]

For example, therefore, a reference to "25 mg tenofovir alafenamide or a pharmaceutically acceptable salt and/or solvate thereof" means an amount of tenofovir alafenamide or a pharmaceutically acceptable salt and/or solvate thereof which provides the same amount of tenofovir alafenamide as 25 mg of tenofovir alafenamide free base.

The amount of tenofovir alafenamide in a solid oral dosage form provided herein is generally between 10 mg and 30 mg, for instance within the range of 20 mg to 30 mg, and in some cases between 24 mg and 28 mg. In certain embodiments, the solid oral dosage form contains 10 mg tenofovir alafenamide e.g. as about 11 mg of tenofovir alafenamide hemifumarate. In other certain specific embodiments, solid oral dosage forms containing 25 mg of tenofovir alafenamide e.g. as about 28 mg of tenofovir alafenamide hemifumarate, are provided.

Emtricitabine

Emtricitabine (FTC) is a nucleoside reverse transcriptase inhibitor having the formula below:

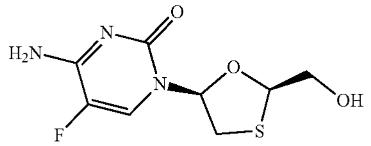 [SMILES: Nc1nc(=O)n([C@@H]2CS[C@H](CO)O2)cc1F]

Its IUPAC name is 4-amino-5-fluoro-1-[(2R,5S)-2-(hydroxymethyl)-1,3-oxathiolan-5-yl]-1,2-dihydropyrimidin-2-one. It is also referred to as 5-fluoro-1-[(2R,5S)-2-(hydroxymethyl)-1,3-oxathiolan-5-yl]cytosine. It is currently authorised as part of EMTRIVA® (emtricitabine 200 mg), TRUVADA® (emtricitabine 200 mg, tenofovir disoproxil fumarate 300 mg), ATRIPLA® (emtricitabine 200 mg, efavirenz 600 mg, tenofovir disoproxil fumarate 300 mg) and STRIBILD® (emtricitabine 200 mg, cobicistat 150 mg, tenofovir disoproxil fumarate 300 mg, elvitegravir 150 mg) and COMPLERA®/EVIPLERA®.

Solid oral dosage forms disclosed herein include emtricitabine, optionally as a pharmaceutically acceptable salt. Emtricitabine can be present within an oral dosage form in solvated or unsolvated form, and references to "emtricitabine" include both of these forms. Typically, emtricitabine is present as a free base.

As used herein, and in the absence of a specific reference to a particular pharmaceutically acceptable salt and/or solvate of emtricitabine, any dosages, whether expressed in e.g. milligrams or as a % by weight, should be taken as referring to the amount of emtricitabine, i.e. the amount of:

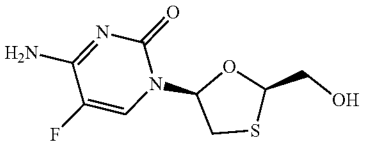 [SMILES: Nc1nc(=O)n([C@@H]2CS[C@H](CO)O2)cc1F]

For example, therefore, a reference to "200 mg emtricitabine or a pharmaceutically acceptable salt and/or solvate thereof" means an amount of emtricitabine or a pharmaceutically acceptable salt and/or solvate thereof which provides the same amount of emtricitabine as 200 mg of emtricitabine free base.

The amount of emtricitabine in a solid oral dosage form provided herein is generally between 180 mg and 220 mg, for instance between 190 mg and 210 mg, and in some cases between 195 mg and 205 mg. In certain specific embodiments, solid oral dosage forms containing 200 mg of emtricitabine are provided.

Solid Oral Dosage Forms

The inventors have successfully formulated emtricitabine and tenofovir alafenamide in a single, stable dosage form that is intended to be pharmacologically efficacious and physically acceptable. The inventors have also successfully formulated rilpivirine, emtricitabine and tenofovir alafenamide in a single, stable dosage form that is intended to be pharmacologically efficacious and physically acceptable. The solid oral dosage forms disclosed herein are intended for pharmaceutical use in human subjects. Accordingly, they must be of an appropriate size and weight for oral human administration (e.g. they should have a total weight of less than about 1.5 g, preferably less than 1.0 g), in addition to being therapeutically efficacious.

In addition to the clinical benefits described above may result from the use of tenofovir alafenamide, the dosage forms of the present invention may afford further advantages. In certain embodiments, the inventors have determined that it is possible to formulate emtricitabine and tenofovir alafenamide into a solid oral dosage form which has a total weight of less than about 850 mg, for instance less than about 750 mg, less than about 500 mg, or less than about 400 mg. In other embodiments containing a third active ingredient (rilpivirine), the inventors have determined that it is possible to formulate the three active ingredients (i.e., rilpivirine, emtricitabine and tenofovir alafenamide) into a solid oral dosage form which has a total weight of less than about 1.0 g, for instance less than about 800 mg, or even less than about 700 mg. This is advantageous given that COMPLERA® has a total weight of about 1200 mg. TRUVADA® has a total weight of about 1000 mg. The provision of a relatively small dosage form (in particular a tablet) represents a clinical advantage because it may be expected to increase patient convenience and thus compliance as compared to larger dosage forms which are more burdensome for patients to swallow. In specific embodiments, the solid oral dosage form of the invention has a total weight of between 600 and 700 mg. In certain embodiments, particularly those containing emtricitabine and tenofovir alafenamide without a third active ingredient, the solid oral dosage form has a total weight of between about 300 mg and about 700 mg, or between about 300 mg and about 500 mg. By way of comparison, TRUVADA® contains about 500 mg of excipients, whereas the presently disclosed dosage forms comprise less than 300 mg of excipients, such as less than 250 mg of excipients, or 200 mg of excipients or less. For example, in certain embodiments, solid oral dosage forms disclosed include between 100 mg and 650 mg of excipients, or between 100 mg and 500 mg of excipients. In certain embodiments, the solid oral dosage forms disclosed herein include between 100 mg and 200 mg of excipients, or between 100 mg and 175 mg of excipients, or between 100 mg and 150 mg of excipients. In certain embodiments, solid oral dosage forms disclosed herein comprise between 120 mg and 150 mg of excipients. In such embodiments, the dosage forms will typically comprise as active ingredients (a) 10 mg or 25 mg tenofovir alafenamide or a pharmaceutically acceptable salt thereof, and (b) 200 mg emtricitabine or a pharmaceutically acceptable salt thereof. For instance, the dosage forms may comprise as active ingredients (a) 10 mg tenofovir alafenamide or a pharmaceutically acceptable salt thereof, and (b) 200 mg emtricitabine or a pharmaceutically acceptable salt thereof. Alternatively, the dosage forms may comprise as active ingredients (a) 25 mg tenofovir alafenamide or a pharmaceutically acceptable salt thereof, and (b) 200 mg emtricitabine or a pharmaceutically acceptable salt thereof. In certain embodiments, the dosage forms will typically comprise as active ingredients (a) 11 mg or 28 mg tenofovir alafenamide hemifumarate, and (b) 200 mg emtricitabine. For instance, the dosage forms may comprise as active ingredients (a) 11 mg tenofovir alafenamide hemifumarate, and (b) 200 mg emtricitabine. Alternatively, the dosage forms may comprise as active ingredients (a) 28 mg tenofovir alafenamide hemifumarate, and (b) 200 mg emtricitabine.

Similarly, where a third active ingredient is present, by way of comparison, COMPLERA® contains over 650 mg of excipients, whereas the presently disclosed dosage forms may comprise less than 600 mg of excipients, such as less than 500 mg of excipients, or less than 400 mg of excipients. For example, solid oral dosage forms disclosed herein may comprise between 200 and 600 mg of excipients, or between 250 mg and 550 mg of excipients, or between 300 mg and 500 mg of excipients. In some embodiments, solid oral dosage forms disclosed herein comprise between 350 mg and 450 mg of excipients. In such embodiments, the dosage forms will typically comprise as active ingredients (a) 25 mg rilpivirine or a pharmaceutically acceptable salt thereof, (b) 25 mg tenofovir alafenamide or a pharmaceutically acceptable salt thereof, and (c) 200 mg emtricitabine or a pharmaceutically acceptable salt thereof. In certain embodiments, the dosage forms will typically comprise as active ingredients (a) 27.5 mg rilpivirine hydrochloride, (b) 28 mg tenofovir alafenamide hemifumarate, and (c) 200 mg emtricitabine.

In certain embodiments, the solid oral dosage forms described herein will be in the form of a tablet. In particular embodiments, they are in the form of a monolayer tablet. In particular embodiments, particularly where a third active ingredient is present in the composition, they may be in the form of a multilayer tablet. This is because the inventors have found that the use of multilayer tablets may assist in optimizing the properties of the dosage form, particularly the stability (e.g. of tenofovir alafenamide). They have also discovered that the use of multilayer tablets may affect the dissolution profile of one or more of the active ingredients within the dosage form, and is therefore likely to have an impact on the in vivo pharmacokinetics of the dosage form. In particular, it has been observed that the dissolution of rilpivirine varies depending on whether the tablet is a monolayer or multilayer tablet. The provision of a tablet with particular pharmacokinetic parameters, e.g. pharmacokinetic parameters that are bioequivalent with existing medicines (or medicines at an advanced stage of the regulatory procedure) is a particular advantage that may be afforded by the present invention. Achieving bioequivalence may require the use of a multilayer tablet.

In one embodiment, a tablet comprising (a) tenofovir alafenamide or a pharmaceutically acceptable salt thereof, and (b) emtricitabine or a pharmaceutically acceptable salt thereof is provided. In one embodiment, the tablet is a monolayer tablet. In one embodiment, the tablet is substantially free of rilpivirine or a pharmaceutically acceptable salt thereof (e.g. the tablet contains less than 1% by weight rilpivirine or a pharmaceutically acceptable salt thereof). In one embodiment, the tablet does not contain lactose and/or starch.

In one embodiment, a multilayer tablet comprising (a) rilpivirine or a pharmaceutically acceptable salt thereof, (b) tenofovir alafenamide or a pharmaceutically acceptable salt thereof, and (c) emtricitabine or a pharmaceutically acceptable salt thereof is provided. In some embodiments, each layer contains at least one of (a), (b), and (c). For instance, the tablet may comprise (a) a first layer comprising rilpivirine or a pharmaceutically acceptable salt thereof, (b) a second layer comprising tenofovir alafenamide or a pharmaceutically acceptable salt thereof, and (c) further comprises emtricitabine or a pharmaceutically acceptable salt thereof. In such embodiments, typically (a) the first layer is substantially free of tenofovir alafenamide or a pharmaceutically acceptable salt thereof, and/or (b) the second layer is substantially free of rilpivirine or a pharmaceutically acceptable salt thereof. In one embodiment (a) the first layer is substantially free of tenofovir alafenamide or a pharmaceutically acceptable salt thereof (e.g. the first layer contains less than 1% by weight tenofovir alafenamide or a pharmaceutically acceptable salt thereof), and (b) the second layer is substantially free of rilpivirine or a pharmaceutically acceptable salt thereof (e.g. the second layer contains less than 1% by weight rilpivirine or a pharmaceutically acceptable salt thereof).

A particular embodiment provides a tablet, wherein the first layer comprises rilpivirine or a pharmaceutically acceptable salt thereof and is substantially free of tenofovir alafenamide or a pharmaceutically acceptable salt thereof (e.g. the first layer contains less than 1% by weight tenofovir alafenamide or a pharmaceutically acceptable salt thereof), and (b) the second layer comprises tenofovir alafenamide or a pharmaceutically acceptable salt thereof and emtricitabine or a pharmaceutically acceptable salt thereof and is substantially free of rilpivirine or a pharmaceutically acceptable salt thereof (e.g. the second layer contains less than 1% by weight rilpivirine or a pharmaceutically acceptable salt thereof). In a particular embodiment, the invention provides a tablet, wherein (a) the first layer comprises 27.5 mg rilpivirine hydrochloride and is substantially free of tenofovir alafenamide or a pharmaceutically acceptable salt thereof (e.g. the first layer contains less than 1% by weight tenofovir alafenamide or a pharmaceutically acceptable salt thereof), and (b) the second layer comprises 28 mg tenofovir alafenamide hemifumarate and 200 mg emtricitabine and is substantially free of rilpivirine or a pharmaceutically acceptable salt thereof (e.g. the second layer contains less than 1% by weight rilpivirine or a pharmaceutically acceptable salt thereof), wherein the first layer has a total weight of less than about 400 mg, such as about 300 mg, and the second layer has a total weight of less than about 450 mg, such as about 350 mg. In one embodiment, the layer containing tenofovir alafenamide or a pharmaceutically acceptable salt thereof does not contain lactose and/or starch.

The tablets disclosed herein are typically immediate release tablets. In one embodiment, the invention provides a tablet which releases at least 80% of (a) tenofovir alafenamide and/or (b) emtricitabine in 20 minutes, measured using USP apparatus II, in 500 ml of 50 mM sodium citrate pH 5.5, at 37° C. and paddle speed of 75 rpm. Typically, the tablets disclosed herein release at least 90% of (a) tenofovir alafenamide and/or (b) emtricitabine in 20 minutes, measured using USP apparatus II, in 500 ml of 50 mM sodium citrate pH 5.5, at 37° C. and paddle speed of 75 rpm. In some embodiments, a tablet that releases less than 50% of rilpivirine in 60 minutes is provided, measured using USP Apparatus II, in 1000 ml of pH 4.5 sodium acetate with 2% polysorbate 20 at 37° C. and paddle speed of 75 rpm.

Tablets disclosed herein will generally have a hardness within the range 13-19 kP (kilopond), and, in certain specific embodiments, have a hardness of 16 kP. Hardness can conveniently be assessed by driving an anvil to compress a tablet at a constant loading rate until it fractures, operating in accordance with USP <1217> (using e.g. a TBH 220, ERWEKA GmbH, Heusenstamm Germany hardness tester).

Tablets of the invention will generally have a friability of <1% by weight. Friability can be assessed according to USP <1216>.

The core of a tablet provided herein may have a hardness of between 13-19 kP, and a friability of <1% by weight.

Tablets will typically include one or more excipients. Excipients should be compatible with the other ingredients of the formulation and physiologically innocuous to the recipient thereof. Examples of suitable excipients are well known to the person skilled in the art of tablet formulation and may be found e.g. in *Handbook of Pharmaceutical Excipients* (eds. Rowe, Sheskey & Quinn), 6th edition 2009. As used herein the term "excipients" is intended to refer to inter alia basifying agents, solubilisers, glidants, fillers, binders, lubricant, diluents, preservatives, surface active agents, dispersing agents and the like. The term also includes agents such as sweetening agents, flavoring agents, coloring agents and preserving agents. Such components will generally be present in admixture within the tablet.

Examples of solubilisers include, but are not limited to, ionic surfactants (including both ionic and non-ionic surfactants) such as sodium lauryl sulphate, cetyltrimethylammonium bromide, polysorbates (such as polysorbate 20 or 80), poloxamers (such as poloxamer 188 or 207), and macrogols. In a particular embodiment, a tablet that comprises rilpivirine or a pharmaceutically acceptable salt thereof, includes a polysorbate, in particular polysorbate 20. In certain specific embodiments, the amount of polysorbate 20 in a tablet of the invention is less than about 5 mg, such as less than about 1 mg, or about 0.5 mg.

Examples of lubricants, glidants and flow aids include, but are not limited to, magnesium stearate, calcium stearate, stearic acid, hydrogenated vegetable oil, glyceryl palmitostearate, glyceryl behenate, sodium stearyl fumarate, colloidal silicon dioxide, and talc. The amount of lubricant in a tablet can generally be between about 0.5-5% by weight. In certain specific embodiments, tablets of the invention include magnesium stearate. In certain embodiments, the tablet includes less than about 20 mg magnesium stearate.

Examples of disintegrants include, but are not limited to, starches, celluloses, cross-linked PVP, sodium starch glycolate, croscarmellose sodium, etc.

Examples of fillers (also known as bulking agents or diluents) include, but are not limited to, starches, maltodextrins, polyols (such as lactose), and celluloses. Tablets provided herein may include lactose and/or microcrystalline cellulose. Lactose can be used in anhydrous or hydrated form (e.g. monohydrate), and is typically prepared by spray drying, fluid bed granulation, or roller drying. In certain embodiments, tablets provided herein include less than about 250 mg lactose, in particular less than about 200 mg lactose, and/or less than about 250 mg microcrystalline cellulose, in particular less than about 200 mg microcrystalline cellulose. Lactose monohydrate is preferred.

Examples of binders include, but are not limited to, cross-linked PVP, HPMC, microcrystalline cellulose, sucrose, starches, etc.

Tablets provided herein may be uncoated or coated (in which case they include a coating). Although uncoated tablets may be used, it is more usual to provide a coated tablet, in which case a conventional non-enteric coating may be used. Film coatings are known in the art and can be composed of hydrophilic polymer materials, but are not limited to, polysaccharide materials, such as hydroxypropylmethyl cellulose (HPMC), methylcellulose, hydroxyethyl cellulose (HEC), hydroxypropyl cellulose (HPC), poly(vinylalcohol-co-ethylene glycol) and other water soluble polymers. Though the water soluble material included in the film coating of the present invention may include a single polymer material, it may also be formed using a mixture of more than one polymer. The coating may be white or coloured e.g. gray. Suitable coatings include, but are not limited to, polymeric film coatings such as those comprising polyvinyl alcohol e.g. 'Opadry® II' (which includes part-hydrolysed PVA, titanium dioxide, macrogol 3350 and talc, with optional colouring such as iron oxide or indigo carmine or iron oxide yellow or FD&C yellow #6). The amount of coating will generally be between about 2-4% of the core's weight, and in certain specific embodiments, about 3%. Unless specifically stated otherwise, where the dosage form is coated, it is to be understood that a reference to % weight of the tablet means that of the total tablet, i.e. including the coating.

Pharmacokinetics

The inventors have found that it is possible to formulate rilpivirine (in particular rilpivirine hydrochloride), emtricitabine and tenofovir alafenamide (in particular tenofovir alafenamide hemifumarate) in a solid oral dosage form which is capable of demonstrating bioequivalence, i.e. equivalent systemic exposure ($AUC_{inf}$, $C_{max}$), for each active ingredient compared to standard comparators. In particular, in some embodiments the tablets of the invention provide plasma concentrations ($AUC_{inf}$, $C_{max}$) of one or more of the three active pharmaceutical ingredients that are bioequivalent to the plasma concentrations produced by the administration of EDURANT® (rilpivirine HCl, 27.5 mg) and/or a fixed dose combination of elvitegravir, cobicistat, emtricitabine, and tenofovir alafenamide hemifumarate (E/C/F/TAF) (corresponding to 150/150/200/10 mg of free base), the latter of which is the subject of a New Drug Application filed in November 2014 with the U.S. Food and Drug Administration, which was approved in November 2015 as GENVOYA®. Achieving bioequivalence of rilpivirine to the currently approved rilpivirine single agent formulation, EDURANT®, was initially a challenge because the dissolution of rilpivirine was found to vary depending on the properties of the dosage form in which the rilpivirine was presented. Based on the findings of the inventors and the present disclosure, the skilled person is able to provide dosage forms which provide such bioequivalence (see for instance the examples, below).

Accordingly, in one embodiment a solid oral dosage form (in particular a tablet) is provided as described herein, wherein the dosage form:

(a) releases emtricitabine in vivo in fed human subjects to provide a plasma $C_{max}$ of from about 1250 to about 2050 ng/ml and/or a $AUC_{inf}$ of from about 7650 to about 12050 h·ng/mL, and/or (b) releases rilpivirine in vivo in fed human subjects to provide a plasma $C_{max}$ of from about 90 to about 160 ng/ml and/or a $AUC_{inf}$ of from about 3050 to about 4850 h·ng/mL, and/or (c) releases tenofovir alafenamide in vivo in fed human subjects to provide a plasma $C_{max}$ of from about 150 to about 260 ng/ml and/or a $AUC_{inf}$ of from about 200 and 340 h·ng/mL.

In some embodiments, the solid oral dosage form will exhibit properties (a) and (b). In other embodiments, the solid oral dosage form will exhibit properties (a) and (c). In some embodiments, the solid oral dosage form will exhibit properties (b) and (c). In some embodiments, the solid oral dosage form will exhibit properties (a), (b) and (c).

In some embodiments, a solid oral dosage form (in particular a tablet) as described herein is provided, for which:

(a) the 90% confidence interval of log-transformed $C_{max}$ and log-transformed $AUC_{inf}$ for rilpivirine in fed human subjects fall completely within the range 80-125% of the log-transformed $C_{max}$ and log-transformed $AUC_{inf}$, respectively, of a reference tablet, wherein the reference tablet has (i) a core consisting of 27.5 mg rilpivirine hydrochloride, lactose monohydrate, croscarmellose sodium, polyvinylpyrrolidone, polysorbate 20, silicified microcrystalline cellulose and magnesium stearate, and (ii) a film coating consisting of a mixture of lactose monohydrate, hypromellose 2910, titanium dioxide E171, polyethylene glycol (macrogol 3000) and triacetin, and/or (b) the 90% confidence interval of log-transformed $C_{max}$ and log-transformed $AUC_{inf}$ for emtricitabine in fed human subjects fall completely within the range 80-125% of the log-transformed $C_{max}$ and log-transformed $AUC_{inf}$, respectively, of a reference tablet, wherein the reference tablet has (i) a core consisting of 150 mg elvitegravir, 60.8 mg lactose monohydrate, 241.5 mg microcrystalline cellulose, 7.5 mg hydroxypropyl cellulose, 11.3 mg sodium lauryl sulfate, 65.8 mg croscarmellose sodium, 200 mg emtricitabine, 11.2 mg tenofovir alafenamide hemifumarate, 288.5 mg cobicistat on silicon dioxide (corresponding to 150 mg of cobicistat), 13.5 mg magnesium stearate, and (ii) a film coating consisting of 31.5 mg of a mixture of polyvinyl alcohol, titanium dioxide, polyethylene glycol, talc, indigo carmine and iron oxide (such as Opadry® II Green), and/or (c) the 90% confidence interval of log-transformed $C_{max}$ and log-transformed $AUC_{inf}$ for tenofovir alafenamide in fed human subjects fall completely within the range 80-125% of the log-transformed $C_{max}$ and log-transformed $AUC_{inf}$, respectively, of a reference tablet, wherein the reference tablet has (i) a core consisting of 150 mg elvitegravir, 60.8 mg lactose monohydrate, 241.5 mg microcrystalline cellulose, 7.5 mg hydroxypropyl cellulose, 11.3 mg sodium lauryl sulfate, 65.8 mg croscarmellose sodium, 200 mg emtricitabine, 11.2 mg tenofovir alafenamide hemifumarate, 288.5 mg cobicistat on silicon dioxide (corresponding to 150 mg of cobicistat), 13.5 mg magnesium stearate, and (ii) a film coating consisting of 31.5 mg of a mixture of polyvinyl alcohol, titanium dioxide, polyethylene glycol, talc, indigo carmine and iron oxide (such as Opadry® II Green).

In some embodiments, the solid oral dosage form will exhibit properties (a) and (b). In other embodiments, the solid oral dosage form will exhibit properties (a) and (c). In some embodiments, the solid oral dosage form will exhibit properties (b) and (c). In some embodiments, the solid oral dosage form will exhibit properties (a), (b) and (c).

$C_{max}$

As used herein, $C_{max}$ is the maximum observed plasma/serum concentration of drug.

In particular embodiments, solid oral dosage forms of the invention provide a plasma $C_{max}$ of rilpivirine in fed patients of from about 90 to about 160 ng/ml, e.g. about 120 ng/ml.

In certain specific embodiments, solid oral dosage forms of the invention provide a plasma $C_{max}$ of emtricitabine in fed patients of from about 1250 to about 2050 ng/mL, e.g. about 1600 ng/ml.

In certain specific embodiments, solid oral dosage forms of the invention provide a plasma $C_{max}$ of tenofovir alafenamide in fed patients of from about 150 to about 260 ng/ml, e.g. about 200 ng/mL.

$AUC_{inf}$

As used herein, $AUC_{inf}$ is the area under the plasma/serum concentration versus time curve extrapolated to infinite time, calculated as $AUC_{0\text{-}last}+(C_{last}/\lambda_z)$.

In certain specific embodiments, solid oral dosage forms of the invention provide a plasma $AUC_{inf}$ of rilpivirine in fed patients of from about 3050 to about 4850 h·ng/mL, e.g. about 3850 h·ng/mL.

In certain specific embodiments, solid oral dosage forms of the invention provide a plasma $AUC_{inf}$ of emtricitabine in fed patients of from about 7650 to about 12050 h·ng/mL, e.g. about 9600 h·ng/mL.

In certain specific embodiments, solid oral dosage forms of the invention provide a plasma $AUC_{inf}$ of tenofovir alafenamide in fed patients of from about 200 and 340 h·ng/mL, e.g. about 260 h·ng/mL.

$AUC_{last}$

As used herein, $AUC_{last}$ is the area under the plasma/serum concentration versus time curve from time zero to the last quantifiable concentration.

In certain specific embodiments, solid oral dosage forms of the invention provide a plasma $AUC_{last}$ of rilpivirine in fed patients of from about 2950 to about 4650 h·ng/mL, e.g. about 3700 h·ng/mL.

In certain specific embodiments, solid oral dosage forms of the invention provide a plasma $AUC_{last}$ of emtricitabine in fed patients of from about 7500 to about 12000 h·ng/mL, e.g. about 9400 h·ng/mL.

In certain specific embodiments, solid oral dosage forms of the invention provide a plasma $AUC_{last}$ of tenofovir alafenamide in fed patients of from about 200 and 315 h·ng/mL, e.g. about 250 h·ng/mL.

$C_{last}$

As used herein, $C_{last}$ is the last observed quantifiable plasma/serum concentration of the drug.

$C_{max}$, $C_{last}$, $AUC_{inf}$, and $AUC_{last}$ are standard pharmacokinetic parameters that can be estimated manually or by using modelling software well known in the art, such as the Pharsight WinNonlin package using a non-compartmental model. The general basis for calculation of these quantities is well-known (e.g. see Rowland & Tozer (2010) *Clinical Pharmacokinetics and Pharmacodynamics: Concepts and Applications* ISBN 978-0781750097, or Jambhekar & Breen (2012) Basic Pharmacokinetics ISBN 978-0853699804). Typically the parameters will be assessed as the average (e.g. geometric or arithmetic mean) from within a group of at least 12 (and normally between 24 and 36) healthy human adults. Parameters should be measured in accordance with standards and practices which would be acceptable to a pharmaceutical regulatory agency such as FDA, EMA, MHLW, or WHO. The values may be based on measurements taken at appropriate intervals following the time of tablet ingestion, such as every hour, or at increasingly sparse sampling intervals, such as 1, 3, 5, 7, 9, 11, 13, 15, 20, and 24 hours after ingestion. They can be assessed either following a single-dose of drug or at steady state, but will typically be assessed following a single-dose.

The inventors have also found that it is possible to formulate emtricitabine and tenofovir alafenamide (in particular tenofovir alafenamide hemifumarate) in a solid oral dosage form which is capable of demonstrating bioequivalence, i.e. equivalent systemic exposure ($AUC_{inf}$, $C_{max}$), for each active ingredient compared to standard comparators. In particular, some embodiments the tablets of the invention provide plasma concentrations ($AUC_{inf}$, $C_{max}$) of one or more of the active pharmaceutical ingredients that are bioequivalent to the plasma concentrations produced by the administration of a fixed dose combination of elvitegravir, cobicistat, emtricitabine, and tenofovir alafenamide hemifumarate (E/C/F/TAF) (corresponding to 150/150/200/10 mg of free base), the latter of which is the subject of a New Drug Application filed in November 2014 with the U.S. Food and Drug Administration. In some embodiments the tablets of the invention, when co-administered with elvitegravir (EVG) 150 mg tablets and cobicistat (COBI) 150 mg tablets, provide plasma concentrations ($AUC_{inf}$, $C_{max}$) of one or more of the active pharmaceutical ingredients that are bioequivalent to the plasma concentrations produced by the administration of a fixed dose combination of elvitegravir, cobicistat, emtricitabine, and tenofovir alafenamide hemifumarate (E/C/F/TAF) (corresponding to 150/150/200/10 mg of free base). In some embodiments the tablets of the invention provide plasma concentrations ($AUC_{inf}$, $C_{max}$) of one or more of the active pharmaceutical ingredients that are bioequivalent to the plasma concentrations produced by the co-administration of Emtriva® (emtricitabine) 200 mg capsules and tenofovir alafenamide hemifumarate (TAF) 25 mg single-agent tablets.

Based on the findings of the inventors and the present disclosure, the skilled person is able to provide dosage forms which provide such bioequivalence (see for instance the examples, below).

Accordingly, in one embodiment a solid oral dosage form (in particular a tablet) is provided as described herein, wherein the dosage form:

(a) releases emtricitabine in vivo in fed human subjects to provide a plasma $C_{max}$ of from about 1300 to about 2100 ng/mL and/or a $AUC_{inf}$ of from about 8200 to about 13200 h·ng/mL, and/or (b) releases tenofovir alafenamide in vivo in fed human subjects to provide a plasma $C_{max}$ of from about 240 to about 390 ng/mL and/or a $AUC_{inf}$ of from about 280 and 450 h·ng/mL.

In one embodiment a solid oral dosage form (in particular a tablet) is provided as described herein, wherein the dosage form:

(a) releases emtricitabine in vivo in fed human subjects to provide a plasma $C_{max}$ of from about 1250 to about 2050 ng/mL and/or a $AUC_{inf}$ of from about 8500 to about 13400 h·ng/mL, and/or (b) releases tenofovir alafenamide in vivo in fed human subjects to provide a plasma $C_{max}$ of from about 200 to about 360 ng/mL and/or a $AUC_{inf}$ of from about 300 and 500 h·ng/mL.

In one embodiment a solid oral dosage form (in particular a tablet) is provided as described herein, wherein the dosage form:

(a) releases emtricitabine in vivo in fed human subjects to provide a plasma $C_{max}$ of from about 1400 to about 2300 ng/mL and/or a $AUC_{inf}$ of from about 7400 to about 11600 h·ng/mL, and/or (b) releases tenofovir alafenamide in vivo in fed human subjects to provide a plasma $C_{max}$ of from about 160 to about 270 ng/ml and/or a $AUC_{inf}$ of from about 190 and 320 h·ng/mL.

In some embodiments, a solid oral dosage form (in particular a tablet) as described herein is provided, for which the 90% confidence intervals of log-transformed $C_{max}$ and log-transformed $AUC_{inf}$ for emtricitabine and tenofovir alafenamide hemifumarate in fed human subjects fall completely within the range 80-125% of the log-transformed $C_{max}$ and log-transformed $AUC_{inf}$, respectively, of a reference tablet, wherein the reference tablet has (i) a core consisting of 150 mg elvitegravir, 60.8 mg lactose monohydrate, 241.5 mg microcrystalline cellulose, 7.5 mg hydroxypropyl cellulose, 11.3 mg sodium lauryl sulfate, 65.8 mg croscarmellose sodium, 200 mg emtricitabine, 11.2 mg tenofovir alafenamide hemifumarate, 288.5 mg cobicistat on silicon dioxide (corresponding to 150 mg of cobicistat), 13.5 mg magnesium stearate, and (ii) a film coating consisting of 31.5 mg of a mixture of polyvinyl alcohol, titanium dioxide, polyethylene glycol, talc, indigo carmine and iron oxide (such as Opadry® II Green).

In some embodiments, a solid oral dosage form (in particular a tablet) as described herein is provided, for which, when co-administered with elvitegravir (EVG) 150 mg tablets and cobicistat (COBI) 150 mg tablets, the 90% confidence intervals of log-transformed $C_{max}$ and log-transformed $AUC_{inf}$ for emtricitabine and tenofovir alafenamide hemifumarate in fed human subjects fall completely within the range 80-125% of the log-transformed $C_{max}$ and log-transformed $AUC_{inf}$, respectively, of a reference tablet, wherein the reference tablet has (i) a core consisting of 150 mg elvitegravir, 60.8 mg lactose monohydrate, 241.5 mg microcrystalline cellulose, 7.5 mg hydroxypropyl cellulose, 11.3 mg sodium lauryl sulfate, 65.8 mg croscarmellose sodium, 200 mg emtricitabine, 11.2 mg tenofovir alafenamide hemifumarate, 288.5 mg cobicistat on silicon dioxide (corresponding to 150 mg of cobicistat), 13.5 mg magnesium stearate, and (ii) a film coating consisting of 31.5 mg of a mixture of polyvinyl alcohol, titanium dioxide, polyethylene glycol, talc, indigo carmine and iron oxide (such as Opadry® II Green).

In some embodiments, a solid oral dosage form (in particular a tablet) as described herein is provided, for which the 90% confidence intervals of log-transformed $C_{max}$ and log-transformed $AUC_{inf}$ for emtricitabine and tenofovir alafenamide hemifumarate in fed human subjects fall completely within the range 80-125% of the log-transformed $C_{max}$ and log-transformed $AUC_{inf}$, respectively, of a reference therapy, wherein the reference therapy consists of administration of (i) a tenofovir alafenamide hemifumarate tablet, consisting of 25 mg tenofovir alafenamide (as the hemifumarate salt), lactose monohydrate, microcrystalline cellulose, croscarmellose sodium, magnesium stearate, wherein the tablets are film coated with polyvinyl alcohol, titanium dioxide, polyethylene glycol, talc and yellow iron oxide, and (ii) an emtricitabine hard gelatin capsule, consisting of 200 mg emtricitabine, crospovidone, magnesium stearate, microcrystalline cellulose, povidone, titanium dioxide, gelatin and blue #2/indigo carmine aluminium lake.

$C_{max}$

In certain specific embodiments, solid oral dosage forms of the invention provide a plasma $C_{max}$ of emtricitabine in fed patients of from about 1300 to about 2100 ng/ml, e.g. about 1660 ng/mL.

In certain specific embodiments, solid oral dosage forms of the invention provide a plasma $C_{max}$ of emtricitabine in fed patients of from about 1250 to about 2050 ng/mL, e.g. about 1600 ng/mL.

In certain specific embodiments, solid oral dosage forms of the invention provide a plasma $C_{max}$ of emtricitabine in fed patients of from about 1400 to about 2300 ng/ml, e.g. about 1800 ng/mL.

In certain specific embodiments, solid oral dosage forms of the invention provide a plasma $C_{max}$ of tenofovir alafenamide in fed patients of from about 240 to about 390 ng/mL, e.g. about 300 ng/ml.

In certain specific embodiments, solid oral dosage forms of the invention provide a plasma $C_{max}$ of tenofovir alafenamide in fed patients of from about 200 to about 360 ng/mL, e.g. about 280 ng/ml.

In certain specific embodiments, solid oral dosage forms of the invention provide a plasma $C_{max}$ of tenofovir alafenamide in fed patients of from about 160 to about 270 ng/ml, e.g. about 200 ng/ml.

$AUC_{inf}$

In certain specific embodiments, solid oral dosage forms of the invention provide a plasma $AUC_{inf}$ of emtricitabine in fed patients of from about 8200 to about 13200 h·ng/mL, e.g. about 10500 h·ng/mL.

In certain specific embodiments, solid oral dosage forms of the invention provide a plasma $AUC_{inf}$ of emtricitabine in fed patients of from about 8500 to about 13400 h·ng/mL, e.g. about 9700 h·ng/ml.

In certain specific embodiments, solid oral dosage forms of the invention provide a plasma $AUC_{inf}$ of emtricitabine in fed patients of from about 7400 to about 11600 h·ng/mL, e.g. about 9300 h·ng/mL.

In certain specific embodiments, solid oral dosage forms of the invention provide a plasma $AUC_{inf}$ of tenofovir alafenamide in fed patients of from about 280 and 450 h·ng/mL, e.g. about 350 h·ng/mL.

In certain specific embodiments, solid oral dosage forms of the invention provide a plasma $AUC_{inf}$ of tenofovir alafenamide in fed patients of from about 300 and 500 h·ng/mL, e.g. about 400 h·ng/mL.

In certain specific embodiments, solid oral dosage forms of the invention provide a plasma $AUC_{inf}$ of tenofovir alafenamide in fed patients of from about 190 and 320 h·ng/mL, e.g. about 250 h·ng/mL.

$AUC_{last}$

In certain specific embodiments, solid oral dosage forms of the invention provide a plasma $AUC_{last}$ of emtricitabine in fed patients of from about 8000 to about 13000 h·ng/mL, e.g. about 10200 h·ng/mL.

In certain specific embodiments, solid oral dosage forms of the invention provide a plasma $AUC_{last}$ of emtricitabine in fed patients of from about 7500 to about 11800 h·ng/mL, e.g. about 9400 h·ng/mL.

In certain specific embodiments, solid oral dosage forms of the invention provide a plasma $AUC_{last}$ of emtricitabine in fed patients of from about 7200 to about 11400 h·ng/mL, e.g. about 9000 h·ng/mL.

In certain specific embodiments, solid oral dosage forms of the invention provide a plasma $AUC_{last}$ of tenofovir alafenamide in fed patients of from about 260 and 430 h·ng/mL, e.g. about 340 h·ng/mL.

In certain specific embodiments, solid oral dosage forms of the invention provide a plasma $AUC_{last}$ of tenofovir alafenamide in fed patients of from about 280 and 470 h·ng/mL, e.g. about 370 h·ng/mL.

In certain specific embodiments, solid oral dosage forms of the invention provide a plasma $AUC_{last}$ of tenofovir alafenamide in fed patients of from about 170 and 310 h·ng/mL, e.g. about 250 h·ng/mL.

$C_{last}$

It is well known in the bioavailability and bioequivalence arts how to determine whether any particular tablet meets regulatory requirements for equivalent bioavailability and pharmacokinetic bioequivalence e.g. see: Niazi (2014) *Handbook of Bioequivalence Testing,* 2nd Edition, ISBN 978-1482226379*; Guidance for Industry Bioavailability and Bioequivalence Studies for Orally Administered Drug Products—General Considerations* FDA March 2003; and *Guideline On The Investigation Of Bioequivalence*, EMEA 2010 CPMP/EWP/QWP/1401/98 Rev. 1/Corr **. To ensure statistical power a study to measure the $C_{max}$, $AUC_{last}$ and $AUC_{inf}$ values will be performed in multiple subjects e.g. in a group of at least 12 (and normally between 24 and 36) healthy human adults.

Because determining the $C_{max}$, $AUC_{last}$ and $AUC_{inf}$ values is necessarily destructive these parameters will not be determined directly for the dosage form (in particular the tablet) in question, but rather for a dosage form made by the same manufacturing process with the same components. Thus a batch of a dosage form (e.g. tablets) can be made by a particular process, and the 90% confidence interval of $C_{max}$, $AUC_{last}$ and $AUC_{inf}$ will be assessed on a sample of those tablets. If these values meet the 80-125% requirement noted above then tablets made by the manufacturing process in question are tablets of the present invention.

Stability

As mentioned above and as explained in more detail in the examples below, the stability of tenofovir alafenamide deteriorates in the presence of emtricitabine. The degradation of tenofovir alafenamide is further accelerated in the presence of rilpivirine. Known degradation products of tenofovir alafenamide include PMPA and PMPA anhydride. Similarly, the stability of emtricitabine in the presence of tenofovir alafenamide and, optionally, rilpivirine HCl is a challenge in formulating a composition comprising these three active ingredients. Known degradation products of emtricitabine include cyclic-FTU-1 and FTU.

The inventors have found that solid oral dosage forms of the invention are stable, i.e. they have acceptable shelf-life, despite the dosage forms containing tenofovir alafenamide and emtricitabine, and, optionally, rilpivirine. Accordingly, solid oral dosage forms that do not comprise a pharmaceutically unacceptable amount of a tenofovir alafenamide degradation product are provided. Also provided is a composition comprising (a) tenofovir alafenamide or a pharmaceutically acceptable salt thereof, and (b) emtricitabine or a pharmaceutically acceptable salt thereof, where the total quantity of degradation products derived from the tenofovir alafenamide or the pharmaceutically acceptable salt thereof is less than 5% (for instance less than about 4.2%, such as less than 4%) after storage for six months at 40° C./75% RH in closed conditions. Also provided is a composition comprising (a) tenofovir alafenamide or a pharmaceutically acceptable salt thereof, and (b) emtricitabine or a pharmaceutically acceptable salt thereof, where the total quantity of degradation products derived from the tenofovir alafenamide or the pharmaceutically acceptable salt thereof is less than 2.5% (such as less than 2%, for instance about 1.7% or about 1.8%) after storage for three months at 40° C./75% RH in closed conditions. Also provided is a composition comprising (a) tenofovir alafenamide or a pharmaceutically acceptable salt thereof, and (b) emtricitabine or a pharmaceutically acceptable salt thereof, where the total quantity of degradation products derived from the tenofovir alafenamide or the pharmaceutically acceptable salt thereof is less than 3% (such as less than 2%) after storage for one month at 40° C./75% RH in open conditions. In a preferred embodiment, the composition is a tablet. In another embodiment, a kit comprising (a) the tablet comprising tenofovir alafenamide or a pharmaceutically acceptable salt thereof, and emtricitabine or a pharmaceutically acceptable salt thereof, and (b) a desiccant (e.g. silica gel) is provided. Optionally, the composition further comprises rilpivirine or a pharmaceutically acceptable salt thereof.

The inventors have conducted drug load studies and have realized that the chemical stability of tenofovir alafenamide varies depending on the proportion of tenofovir alafenamide within a given composition. Accordingly, in some embodiments, a solid composition comprising tenofovir alafenamide or a pharmaceutically acceptable salt thereof is provided, wherein the proportion of tenofovir alafenamide or a pharmaceutically acceptable salt thereof in the composition is from about 2.5% to about 12% by weight. In some embodiments, a solid composition comprising tenofovir alafenamide or a pharmaceutically acceptable salt thereof is provided, wherein the proportion of tenofovir alafenamide or a pharmaceutically acceptable salt thereof in the composition is from about 4% to about 12% by weight. In some embodiments, a solid composition is provided which comprises from about 5% to about 15% by weight tenofovir alafenamide hemifumarate, e.g. about 7% to about 9% by weight tenofovir alafenamide hemifumarate, in particular about 8% by weight tenofovir alafenamide hemifumarate. In another embodiment, a solid composition comprising from about 2-4% by weight tenofovir alafenamide hemifumarate is provided, e.g. 2.5% by weight tenofovir alafenamide hemifumarate. In some embodiments, a solid composition comprising about 2.6%, about 2.7%, about 2.8%, about 2.9%, about 3.0%, about 3.1%, about 3.2%, about 3.3%, about 3.4%, or about 3.5% by weight tenofovir alafenamide hemifumarate. The composition may take various forms. It may, for example, be in the form of a powder. In other embodiments, the composition is a compressed dosage form, such as a tablet.

In addition, tenofovir alafenamide undergoes solid-state hydrolysis and accordingly the inclusion of desiccant may assist in facilitating an acceptable shelf-life. Thus, a kit is provided which comprises (a) a tablet comprising tenofovir alafenamide or a pharmaceutically acceptable salt thereof, and emtricitabine or a pharmaceutically acceptable salt thereof, and (b) a desiccant. In some embodiments, a kit is provided which comprises (a) a tablet comprising rilpivirine or a pharmaceutically acceptable salt thereof, tenofovir alafenamide or a pharmaceutically acceptable salt thereof, and emtricitabine or a pharmaceutically acceptable salt thereof, and (b) a desiccant. The inventors have observed that the stability of tenofovir alafenamide in certain formulations is dependent on desiccant level. In certain embodiments, therefore, the kit includes silica gel as a desiccant. In certain specific embodiments, the kit includes 3 g silica gel as a desiccant. The kit may optionally further include polyester coil packing material. In certain embodiments, the total quantity of degradation products derived from the tenofovir alafenamide or the pharmaceutically acceptable salt thereof in the tablet is less than about 2%, e.g., less than about 1.5% or less than about 1%, after storage for 12 months at 30° C./75% RH. In certain embodiments, the total quantity of degradation products derived from the tenofovir alafenamide or the pharmaceutically acceptable salt thereof is less than 2.5% (such as less than 2%, for instance about 1.7% or about 1.8%) after storage for three months at 40° C./75% RH. The kit of the invention may comprise a bottle suitable for storing the oral dosage forms described herein.

The use of multilayer tablets of the type described above may also assist in optimizing the stability of the dosage forms. For instance, a tablet is provided which comprises (a) 25 mg rilpivirine or a pharmaceutically acceptable salt thereof, (b) 25 mg tenofovir alafenamide or a pharmaceutically acceptable salt thereof, and (c) 200 mg emtricitabine or a pharmaceutically acceptable salt thereof, wherein (a) and (b) are segregated, and wherein the tablet has a total weight of less than about 1.5 g. Multilayer tablets are described in further detail above and in the examples below.

The invention provides a multilayer tablet comprising (a) rilpivirine or a pharmaceutically acceptable salt thereof, (b) tenofovir alafenamide or a pharmaceutically acceptable salt thereof, and (c) emtricitabine or a pharmaceutically acceptable salt thereof.

In an embodiment, the multilayer tablet disclosed herein comprises (a) a first layer comprising rilpivirine or a pharmaceutically acceptable salt thereof, (b) a second layer containing tenofovir alafenamide or a pharmaceutically acceptable salt thereof, and (c) further comprises emtricitabine or a pharmaceutically acceptable salt thereof.

In an embodiment of the multilayer tablet disclosed herein, (a) the first layer is substantially free of tenofovir alafenamide or a pharmaceutically acceptable salt thereof, and/or (b) the second layer is substantially free of rilpivirine or a pharmaceutically acceptable salt thereof.

In an embodiment of the multilayer tablet disclosed herein, (a) the first layer comprises rilpivirine or a pharmaceutically acceptable salt thereof and is substantially free of tenofovir alafenamide or a pharmaceutically acceptable salt thereof, and (b) the second layer comprises tenofovir alafenamide or a pharmaceutically acceptable salt thereof and emtricitabine or a pharmaceutically acceptable salt thereof and is substantially free of rilpivirine or a pharmaceutically acceptable salt thereof.

In an embodiment of the multilayer tablet disclosed herein, the first layer is substantially free of emtricitabine.

In one embodiment, the multilayer tablet disclosed herein comprises 25±3 mg of rilpivirine. In one embodiment, the multilayer tablet disclosed herein comprises 200±20 mg of emtricitabine. In one embodiment, the multilayer tablet disclosed herein comprises 25±3 mg of tenofovir alafenamide.

In one embodiment, the multilayer tablet disclosed herein comprises 27.5±3 mg of rilpivirine HCl. In one embodiment, the multilayer tablet disclosed herein comprises 200±20 mg of emtricitabine. In one embodiment, the multilayer tablet disclosed herein comprises 28±3 mg of tenofovir alafenamide hemifumarate.

In one embodiment, the first layer of the multilayer tablet disclosed herein comprises one or more excipients, for example one or more diluents, disintegrants, binders, or lubricants.

In one embodiment, the first layer of the multilayer tablet comprises a basifying agent. In one embodiment, the basifying agent is selected from croscarmellose sodium, calcium carbonate, sodium hydroxide, aluminium oxide, alkali metal hydroxides (e.g. such as sodium hydroxide, potassium hydroxide and lithium hydroxide), alkaline earth metal hydroxides (e.g. calcium hydroxide, and magnesium hydroxide), aluminium hydroxide, dihydroaluminum, sodium carbonate, aluminium magnesium hydroxide sulfate, aluminium hydroxide magnesium carbonate, ammonium hydroxides, magnesium carbonate, magnesium stearate, piperazine, sodium acetate, sodium citrate, sodium tartrate, sodium maleate, and sodium succinate and mixtures thereof.

In one embodiment, the first layer of the multilayer tablet of the invention comprises croscarmellose sodium and polysorbate 20. In one embodiment, the first layer of the multilayer tablet of the invention comprises lactose monohydrate, povidone, croscarmellose sodium, polysorbate 20, microcrystalline cellulose, and magnesium stearate.

In one embodiment a tablet is provided wherein less than about 15 weight percent of the first layer is rilpivirine hydrochloride. In one embodiment a tablet is provided wherein less than about 12.2 weight percent of the first layer is rilpivirine hydrochloride. In one embodiment a tablet is provided wherein less than about 12 weight percent of the first layer is rilpivirine hydrochloride.

In one embodiment a tablet is provided wherein the first layer comprises 27.5±1.4 mg of rilpivirine hydrochloride and wherein the total weight of the first layer is at least about 230 mg.

In one embodiment a tablet is provided wherein the first layer comprises 27.5±1.4 mg of rilpivirine hydrochloride and wherein the total weight of the first layer is at least about 240 mg.

In one embodiment a tablet is provided wherein the first layer comprises 27.5±1.4 mg of rilpivirine hydrochloride and wherein the total weight of the first layer is at least about 250 mg.

In one embodiment a tablet is provided wherein the first layer comprises 27.5±1.4 mg of rilpivirine hydrochloride and wherein the total weight of the first layer is at least about 260 mg.

In one embodiment a tablet is provided wherein the first layer comprises 27.5±1.4 mg of rilpivirine hydrochloride and wherein the total weight of the first layer is at least about 270 mg.

In one embodiment a tablet is provided wherein the first layer comprises 27.5±1.4 mg of rilpivirine hydrochloride and wherein the total weight of the first layer is at least about 280 mg.

In one embodiment a tablet is provided wherein the first layer comprises 27.5±1.4 mg of rilpivirine hydrochloride and wherein the total weight of the first layer is at least about 290 mg.

In one embodiment a tablet is provided wherein the first layer comprises 27.5±1.4 mg of rilpivirine hydrochloride and wherein the total weight of the first layer is at least about 300 mg.

In one embodiment a tablet is provided wherein the first layer comprises 27.5±1.4 mg of rilpivirine hydrochloride and wherein the total weight of the first layer is at least about 230 mg and is less than about 325 mg.

In one embodiment a tablet is provided wherein the first layer comprises 27.5±1.4 mg of rilpivirine hydrochloride and wherein the total weight of the first layer is at least about 300 mg and is less than about 325 mg.

In one embodiment a tablet is provided wherein the first layer comprises 27.5±1.4 mg of rilpivirine hydrochloride and wherein the total weight of the first layer is at least about 290 mg and is less than about 310 mg.

In one embodiment, the first layer of the multilayer tablet of the invention has a total weight of 300±75 mg, or 300±25 mg, or 300±10 mg, or 300 mg.

In one embodiment, the first layer of the multilayer tablet comprises:

| Ingredient | Mass (mg) |
|---|---|
| Rilpivirine or a salt thereof | 20-35 |
| Microcrystalline cellulose | 40-100 |
| Croscarmellose sodium | 1-30 |
| Lactose | 150-250 |
| Povidone | 1-10 |
| Polysorbate 20 | 0.1-5 |
| Magnesium stearate | 1-10 |

In one embodiment, the first layer of the multilayer tablet comprises:

| Ingredient | Mass (mg) |
|---|---|
| Rilpivirine HCl | 24-31 |
| Microcrystalline cellulose | 50-80 |
| Croscarmellose sodium | 2-20 |
| Lactose | 130-230 |
| Povidone | 2-5 |
| Polysorbate 20 | 0.1-2 |
| Magnesium stearate | 2-6 |

In one embodiment, the first layer of the multilayer tablet comprises:

| Ingredient | Mass (mg) |
|---|---|
| Rilpivirine HCl | 27.5 ± 3 |
| Microcrystalline cellulose | 60.0 ± 12 |
| Croscarmellose sodium | 15 ± 3 |
| Lactose monohydrate | 189 ± 40 |
| Povidone | 3.3 ± 1 |
| Polysorbate 20 | 0.4 ± 0.1 |
| Magnesium stearate | 3.0 ± 1 |

In one embodiment, the first layer of the multilayer tablet consists of:

| Ingredient | Mass (mg) |
|---|---|
| Rilpivirine HCl | 27.5 ± 2.8 |
| Microcrystalline cellulose | 60.0 ± 6.0 |
| Croscarmellose sodium | 16.1 ± 1.6 |
| Lactose | 189.8 ± 19.0 |
| Povidone | 3.3 ± 0.3 |
| Polysorbate 20 | 0.4 ± 0.04 |
| Magnesium stearate | 3.0 ± 0.3 |

In one embodiment, the first layer of the multilayer tablet consists of:

| Ingredient | Mass (mg) |
|---|---|
| Rilpivirine HCl | 27.5 ± 1.4 |
| Microcrystalline cellulose | 60.0 ± 3.0 |
| Croscarmellose sodium | 16.1 ± 0.8 |
| Lactose | 189.8 ± 9.5 |
| Povidone | 3.3 ± 0.17 |
| Polysorbate 20 | 0.4 ± 0.02 |
| Magnesium stearate | 3.0 ± 0.15 |

In one embodiment, the first layer of the multilayer tablet consists of:

| Ingredient | Mass (mg) |
|---|---|
| Rilpivirine HCl | 27.5 |
| Microcrystalline cellulose | 60.00 |
| Croscarmellose sodium | 16.10 |
| Lactose | 189.8 |
| Povidone | 3.25 |
| Polysorbate 20 | 0.35 |
| Magnesium stearate | 3.00 |

In one embodiment, the first layer of the multilayer tablet consists of:

| Ingredient | Mass (mg) |
|---|---|
| Intragranular | |
| Rilpivirine HCl | 27.5 |
| Lactose monohydrate | 55.10 |
| Polysorbate 20 | 0.35 |
| Povidone K29/32 | 3.25 |
| Croscarmellose sodium | 1.10 |
| Extragranular | |
| Lactose Monohydrate | 134.70 |
| Croscarmellose sodium | 15.00 |
| Microcrystalline sodium | 60.00 |
| Magnesium stearate | 3.00 |
| Total layer weight | 300 |

In one embodiment, the second layer of the multilayer tablet comprises one or more excipients, for example, one or more diluents, disintegrants, binders, or lubricants.

In one embodiment, the second layer of the multilayer tablet comprises microcrystalline cellulose and croscarmellose sodium.

In one embodiment, the second layer of the multilayer tablet comprises microcrystalline cellulose, croscarmellose sodium and magnesium stearate.

In one embodiment, the second layer of the multilayer tablet comprises 20-30 mg of croscarmellose sodium. In one embodiment, the second layer of the multilayer tablet comprises 80-90 mg of microcrystalline sodium. In one embodiment, the second layer of the multilayer tablet comprises 1-7 mg of magnesium stearate.

In one embodiment, the second layer of the multilayer tablet does not comprise lactose. In one embodiment, the second layer of the multilayer tablet does not comprise starch. In one embodiment, the second layer of the multilayer tablet comprises neither lactose nor starch.

In one embodiment, the second layer of the multilayer tablet has a total weight of less than 600 mg, or less than 500 mg, or less than 400 mg, or less than 375 mg. In one embodiment, the second layer of the multilayer tablet has a total weight of 350 mg±50 mg or 350 mg±25 mg, or 350 mg±5 mg, or 350 mg.

In one embodiment, over 40% by weight of the second layer of the multilayer tablet is emtricitabine or a salt thereof and tenofovir alafenamide or a salt thereof. In one embodiment, over 50% by weight of the second layer of the multilayer tablet is emtricitabine or a salt thereof and tenofovir alafenamide or a salt thereof. In one embodiment of the invention, over 60% by weight of the second layer of the multilayer tablet is emtricitabine or a salt thereof and tenofovir alafenamide or a salt thereof. In one embodiment, over 64% by weight of the second layer of the multilayer tablet is emtricitabine or a salt thereof and tenofovir alafenamide or a salt thereof. In one embodiment of the invention, over 65% by weight of the second layer of the multilayer tablet is emtricitabine and tenofovir alafenamide hemifumarate.

In one embodiment, the second layer of the multilayer tablet contains less than 250 mg of excipients, for example less than 200 mg, or less than 150 mg, or less than 130 mg, or less than 120 mg of excipients.

In one embodiment, at least 50% by weight of the second layer of the multilayer tablet is emtricitabine. In one embodiment of the invention, at least 55% by weight of the second layer of the multilayer tablet is emtricitabine.

In one embodiment, at least 5% by weight of the second layer of the multilayer tablet is tenofovir alafenamide hemifumarate. In one embodiment, at least 7% by weight of the second layer of the multilayer tablet is tenofovir alafenamide hemifumarate. In one embodiment, at least 8% by weight of the second layer of the multilayer tablet is tenofovir alafenamide hemifumarate.

In one embodiment, less than 20% by weight of the second layer of the multilayer tablet is croscarmellose sodium. In one embodiment, less than 10% by weight of the second layer of the multilayer tablet is croscarmellose sodium. The use of croscarmellose sodium may provide particular advantages in terms of stabilizing the tenofovir alafenamide or a pharmaceutically acceptable salt thereof. For instance, the inventors have found that the use of about 7 to 9% (e.g. about 8%) croscarmellose sodium by weight of the second layer may provide enhanced stability relative to other amounts of croscarmellose sodium (e.g. 6% by weight) and/or other disintegrants e.g. polyvinylpyrrolidone.

In one embodiment, less than 40% by weight of the second layer of the multilayer tablet is microcrystalline cellulose. In one embodiment, less than 30% by weight of the second layer of the multilayer tablet is microcrystalline cellulose. In one embodiment, less than 26% by weight of the second layer of the multilayer tablet is microcrystalline cellulose.

In one embodiment, the total weight of the second layer is less than 200% of the total weight of the first layer. In one embodiment, the total weight of the second layer is less than 150% of the total weight of the first layer. In one embodiment, the total weight of the second layer is less than 130% of the total weight of the first layer. In one embodiment, the total weight of the second layer is less than 120% of the total weight of the first layer. In one embodiment, the total weight of the second layer is less than 117% of the total weight of the first layer.

In one embodiment, the second layer of the multilayer tablet comprises:

| Ingredient | Mass (mg) |
|---|---|
| Emtricitabine or a salt thereof | 150-250 |
| Tenofovir alafenamide or a salt thereof | 20-35 |
| Croscarmellose sodium | 20-35 |
| Microcrystalline cellulose | 70-100 |
| Magnesium stearate | 1-7 |

-continued

In one embodiment, the second layer of the multilayer tablet comprises:

| Ingredient | Mass (mg) |
|---|---|
| Emtricitabine | 170-230 |
| Tenofovir alafenamide hemifumarate | 22-32 |
| Croscarmellose sodium | 20-35 |
| Microcrystalline cellulose | 70-100 |
| Magnesium stearate | 1-7 |

In one embodiment, the second layer of the multilayer tablet consists of:

| Ingredient | Mass (mg) |
|---|---|
| Emtricitabine | 200 ± 20 |
| Tenofovir alafenamide hemifumarate | 28 ± 3 |
| Croscarmellose sodium | 28 ± 3 |
| Microcrystalline cellulose | 89 ± 9 |
| Magnesium stearate | 5.2 ± 1.1 |

In one embodiment, the second layer of the multilayer tablet consists of:

| Ingredient | Mass (mg) |
|---|---|
| Emtricitabine | 200 ± 10 |
| Tenofovir alafenamide hemifumarate | 28 ± 1.4 |
| Croscarmellose sodium | 28 ± 1.4 |
| Microcrystalline cellulose | 89 ± 4 |
| Magnesium stearate | 5.2 ± 0.5 |

In one embodiment, the second layer of the multilayer tablet consists of:

| Ingredient | Mass (mg) |
|---|---|
| Emtricitabine | 199.99 |
| Tenofovir alafenamide hemifumarate | 28.04 |
| Croscarmellose sodium | 28.00 |
| Microcrystalline cellulose | 88.69 |
| Magnesium stearate | 5.20 |

In one embodiment, the second layer of the multilayer tablet consists of:

| Ingredient | Mass (mg) |
|---|---|
| Intragranular | |
| Emtricitabine | 199.99 |
| Tenofovir alafenamide hemifumarate | 28.04 |
| Croscarmellose sodium | 28.00 |
| Microcrystalline cellulose | 88.69 |
| Magnesium stearate | 2.60 |
| Extragranular | |
| Magnesium stearate | 2.60 |
| Total layer weight | 350 |

In one embodiment of the multilayer tablet of the invention, the first layer is in contact with the second layer.

In one embodiment, the multilayer tablet further comprises a third layer that is between and that separates the first layer and the second layer. In one embodiment, the third layer of the multilayer tablet comprises lactose monohydrate, or microcrystalline cellulose, or a mixture thereof.

In one embodiment, the multilayer tablet further comprises a film coating. In one embodiment the film coating comprises polyvinyl alcohol, polyethylene glycol, talc, titanium dioxide, and black iron oxide. In one embodiment the film coating consists of 19.5±10 mg of Opadry II 85F17636 Gray.

In one embodiment, a tablet is provided comprising a first layer consisting of:

| Ingredient | Mass (mg) |
|---|---|
| Rilpivirine HCl | 27.5 ± 3 |
| Microcrystalline cellulose | 60.0 ± 12 |
| Croscarmellose sodium | 16 ± 3 |
| Lactose monohydrate | 189 ± 40 |
| Povidone | 3.3 ± 1 |
| Polysorbate 20 | 0.4 ± 0.1 |
| Magnesium stearate | 3.0 ± 1 |

and a second layer consisting of:

| Ingredient | Mass (mg) |
|---|---|
| Emtricitabine | 200 ± 20 |
| Tenofovir alafenamide hemifumarate | 28 ± 3 |
| Croscarmellose sodium | 28 ± 3 |
| Microcrystalline cellulose | 89 ± 9 |
| Magnesium stearate | 5.2 ± 1.1 |

In one embodiment, a tablet is provided comprising a first layer consisting of:

| Ingredient | Mass (mg) |
|---|---|
| Rilpivirine HCl | 27.5 ± 1.4 |
| Microcrystalline cellulose | 60.0 ± 3.0 |
| Croscarmellose sodium | 16.1 ± 0.8 |
| Lactose | 189.8 ± 9.5 |
| Povidone | 3.3 ± 0.17 |
| Polysorbate 20 | 0.4 ± 0.02 |
| Magnesium stearate | 3.0 ± 0.15 |

and a second layer consisting of:

| Ingredient | Mass (mg) |
|---|---|
| Emtricitabine | 200 ± 10 |
| Tenofovir alafenamide hemifumarate | 28 ± 1.4 |
| Croscarmellose sodium | 28 ± 1.4 |
| Microcrystalline cellulose | 89 ± 4 |
| Magnesium stearate | 5.2 ± 0.5 |

In one embodiment, a tablet is provided comprising a first layer consisting of:

| | Weight (mg) | % w/w (in layer) |
|---|---|---|
| Intragranular | | |
| Rilpivirine HCl | 27.50 | 9.2 |
| Lactose Monohydrate | 55.10 | 18.4 |
| Polysorbate 20 | 0.35 | 0.12 |
| Povidone K29/32 | 3.25 | 1.1 |
| Croscarmellose sodium | 1.10 | 0.37 |
| Extragranular | | |
| Lactose Monohydrate | 134.70 | 44.9 |
| Croscarmellose sodium | 15.00 | 5.0 |
| Microcrystalline cellulose | 60.00 | 20.0 |
| Magnesium stearate | 3.00 | 1.0 |

and a second layer consisting of:

| | Weight (mg) | % w/w (in layer) |
|---|---|---|
| Intragranular | | |
| Emtricitabine | 199.99 | 57.1 |
| Tenofovir alafenamide hemifumarate | 28.04 | 8.01 |
| Croscarmellose sodium | 28.00 | 8.0 |
| Microcrystalline cellulose | 88.69 | 25.3 |
| Magnesium stearate | 2.60 | 0.75 |
| Extragranular | | |
| Magnesium stearate | 2.60 | 0.75 |

and optionally a film coating.

In one embodiment, a tablet is provided consisting of a first layer consisting of:

| | Weight (mg) | % w/w (in layer) |
|---|---|---|
| Intragranular | | |
| Rilpivirine HCl | 27.50 | 9.2 |
| Lactose Monohydrate | 55.10 | 18.4 |
| Polysorbate 20 | 0.35 | 0.12 |
| Povidone K29/32 | 3.25 | 1.1 |
| Croscarmellose sodium | 1.10 | 0.37 |
| Extragranular | | |
| Lactose Monohydrate | 134.70 | 44.9 |
| Croscarmellose sodium | 15.00 | 5.0 |
| Microcrystalline cellulose | 60.00 | 20.0 |
| Magnesium stearate | 3.00 | 1.0 |

and a second layer consisting of:

| | Weight (mg) | % w/w (in layer) |
|---|---|---|
| Intragranular | | |
| Emtricitabine | 199.99 | 57.1 |
| Tenofovir alafenamide hemifumarate | 28.04 | 8.01 |
| Croscarmellose sodium | 28.00 | 8.0 |
| Microcrystalline cellulose | 88.69 | 25.3 |
| Magnesium stearate | 2.60 | 0.75 |
| Extragranular | | |
| Magnesium stearate | 2.60 | 0.75 |

and a film coating consisting of 19.5 mg of Opadry II 85F17636 Gray (a combination of polyvinyl alcohol, polyethylene glycol (PEG), talc, titanium dioxide and iron oxide black).

Another aspect of the invention provides a solid oral dosage form comprising tenofovir alafenamide or a pharmaceutically acceptable salt thereof and emtricitabine or a pharmaceutically acceptable salt thereof. In one embodiment, this solid oral dosage form is a tablet. In one embodiment, this solid oral dosage form is a tablet which is coated. In one embodiment, this coating is a film coating, such as Opadry II.

In one embodiment, the tablet comprises microcrystalline cellulose and croscarmellose sodium.

In one embodiment, the tablet comprises microcrystalline cellulose, croscarmellose sodium and magnesium stearate.

In one embodiment, the tablet comprises 20-30 mg of croscarmellose sodium. In one embodiment, the tablet comprises 80-90 mg of microcrystalline sodium. In one embodiment, the tablet comprises 2-7 mg of magnesium stearate.

In one embodiment, the tablet does not comprise lactose. In one embodiment, the tablet does not comprise starch. In one embodiment, the tablet comprises neither lactose nor starch.

In one embodiment, the tablet has a total weight of less than 600 mg, or less than 500 mg, or less than 400 mg, or less than 375 mg. In one embodiment, the tablet has a total weight of 350 mg±50 mg or 350 mg±25 mg, or 350 mg±5 mg, or 350 mg.

In one embodiment the tablet is coated and the tablet has a total weight of less than 600 mg, such as less than 500 mg, less than 400 mg, or less than 375 mg. In one embodiment the tablet is coated and the tablet has a total weight of 360.5 mg±50 mg, such as 360.5 mg±25 mg, 360.5 mg±5 mg, or 360.5 mg.

In one embodiment, over 40% by weight of the tablet is emtricitabine or a salt thereof and tenofovir alafenamide or a salt thereof. In one embodiment, over 50% by weight of the tablet is emtricitabine or a salt thereof and tenofovir alafenamide or a salt thereof. In one embodiment, over 60% by weight of the tablet of the invention is emtricitabine or a salt thereof and tenofovir alafenamide or a salt thereof. In one embodiment, over 64% by weight of the tablet is emtricitabine or a salt thereof and tenofovir alafenamide or a salt thereof. In one embodiment, over 65% by weight of the tablet is emtricitabine or a salt thereof and tenofovir alafenamide or a salt thereof. In one embodiment of the invention, over 65% by weight of the tablet is emtricitabine and tenofovir alafenamide hemifumarate.

In one embodiment, about 40% to about 75% by weight of the tablet is emtricitabine or a salt thereof and tenofovir alafenamide or a salt thereof. In one embodiment, about 50% to about 75% by weight of the tablet is emtricitabine or a salt thereof and tenofovir alafenamide or a salt thereof. In one embodiment, about 50% to about 70% by weight of the tablet is emtricitabine or a salt thereof and tenofovir alafenamide or a salt thereof. In one embodiment, about 60% to about 75% by weight of the tablet of the invention is emtricitabine or a salt thereof and tenofovir alafenamide or a salt thereof. In one embodiment, about 64% to about 75% by weight of the tablet is emtricitabine or a salt thereof and tenofovir alafenamide or a salt thereof. In one embodiment, about 65% to about 75% by weight of the tablet is emtricitabine or a salt thereof and tenofovir alafenamide or a salt thereof.

In one embodiment, the tablet is coated and over 40% by weight of the tablet is emtricitabine or a pharmaceutically acceptable salt thereof and tenofovir alafenamide or a pharmaceutically acceptable salt thereof. In one embodiment, the tablet is coated and over 50% by weight of the tablet is emtricitabine or a pharmaceutically acceptable salt thereof and tenofovir alafenamide or a pharmaceutically acceptable salt thereof. In one embodiment, the tablet is coated and over 58% by weight of the tablet of the invention is emtricitabine or a pharmaceutically acceptable salt thereof and tenofovir alafenamide or a pharmaceutically acceptable salt thereof. In one embodiment, the tablet is coated and over 60% by weight of the tablet is emtricitabine or a pharmaceutically acceptable salt thereof and tenofovir alafenamide or a pharmaceutically acceptable salt thereof. In one embodiment, the tablet is coated and over 63% by weight of the tablet is emtricitabine or a pharmaceutically acceptable salt thereof and tenofovir alafenamide or a pharmaceutically acceptable salt thereof.

In one embodiment, the tablet is coated and about 40% to about 75% by weight of the tablet is emtricitabine or a pharmaceutically acceptable salt thereof and tenofovir alafenamide or a pharmaceutically acceptable salt thereof. In one embodiment, the tablet is coated and about 50% to about 75% by weight of the tablet is emtricitabine or a pharmaceutically acceptable salt thereof and tenofovir alafenamide or a pharmaceutically acceptable salt thereof. In one embodiment, the tablet is coated and about 50% to about 70% by weight of the tablet is emtricitabine or a pharmaceutically acceptable salt thereof and tenofovir alafenamide or a pharmaceutically acceptable salt thereof. In one embodiment, the tablet is coated and about 58% to about 70% by weight of the tablet of the invention is emtricitabine or a pharmaceutically acceptable salt thereof and tenofovir alafenamide or a pharmaceutically acceptable salt thereof. In one embodiment, the tablet is coated and about 60% to about 70% by weight of the tablet is emtricitabine or a pharmaceutically acceptable salt thereof and tenofovir alafenamide or a pharmaceutically acceptable salt thereof. In one embodiment, the tablet is coated and about 63% to about 70% by weight of the tablet is emtricitabine or a pharmaceutically acceptable salt thereof and tenofovir alafenamide or a pharmaceutically acceptable salt thereof.

In one embodiment of the invention, the tablet is coated and over 50% by weight of the tablet is emtricitabine and tenofovir alafenamide hemifumarate. In one embodiment of the invention, the tablet is coated and over 58% by weight of the tablet is emtricitabine and tenofovir alafenamide hemifumarate. In one embodiment of the invention, the tablet is coated and over 63% by weight of the tablet is emtricitabine and tenofovir alafenamide hemifumarate.

In one embodiment of the invention, the tablet is coated and about 50% to about 75% by weight of the tablet is emtricitabine and tenofovir alafenamide hemifumarate. In one embodiment of the invention, the tablet is coated and about 58% to about 70% by weight of the tablet is emtricitabine and tenofovir alafenamide hemifumarate. In one embodiment of the invention, the tablet is coated and about 63% to about 70% by weight of the tablet is emtricitabine and tenofovir alafenamide hemifumarate.

In one embodiment of the invention, the tablet contains less than 250 mg of excipients, for example less than 200 mg, or less than 150 mg, or less than 130 mg, or less than 120 mg of excipients.

In one embodiment of the invention, at least 50% by weight of the tablet is emtricitabine. In one embodiment of the invention, at least 55% by weight of the tablet is emtricitabine.

In one embodiment of the invention, about 50% to about 65% by weight of the tablet is emtricitabine. In one embodiment of the invention, about 55% to about 60% by weight of the tablet is emtricitabine.

In one embodiment, at least 3% by weight of the tablet is tenofovir alafenamide hemifumarate. In one embodiment, at least 5% by weight of the tablet is tenofovir alafenamide hemifumarate. In one embodiment, at least 7% by weight of the tablet is tenofovir alafenamide hemifumarate. In one embodiment, at least 8% by weight of the tablet is tenofovir alafenamide hemifumarate. In one embodiment, the tablet comprises 3-4% by weight tenofovir alafenamide hemifumarate, preferably about 3% tenofovir alafenamide hemifumarate. In another embodiment, the tablet comprises 7-9% by weight tenofovir alafenamide hemifumarate, preferably about 8% by weight tenofovir alafenamide hemifumarate.

In one embodiment, about 3% to about 15% by weight of the tablet is tenofovir alafenamide hemifumarate. In one embodiment, about 5% to about 10% by weight of the tablet is tenofovir alafenamide hemifumarate. In one embodiment, about 7% to about 9% by weight of the tablet is tenofovir alafenamide hemifumarate.

In one embodiment of the invention, the tablet comprises a) tenofovir alafenamide or a pharmaceutically acceptable salt thereof and b) emtricitabine or a pharmaceutically acceptable salt thereof, and the total quantity of degradation products derived from the tenofovir alafenamide or a pharmaceutically acceptable salt thereof is less than about 2.5%, such as less than 2%, for instance about 1.7% or 1.8%, after storage for 3 months at 40° C./75% RH in closed conditions.

In one embodiment of the invention, the tablet comprises a) tenofovir alafenamide hemifumarate and b) emtricitabine, and the total quantity of degradation products derived from the tenofovir alafenamide hemifumarate is less than about 2.5%, such as less than 2%, for instance about 1.7% or 1.8%, after storage for 3 months at 40° C./75% RH in closed conditions.

In one embodiment of the invention, the tablet comprises 7-9% by weight tenofovir alafenamide or a pharmaceutically acceptable salt thereof, preferably about 8% by weight tenofovir alafenamide or a pharmaceutically acceptable salt thereof, and the total quantity of degradation products derived from the tenofovir alafenamide or a pharmaceutically acceptable salt thereof is less than about 2%, for instance about 1.7%, after storage for 3 months at 40° C./75% RH in closed conditions.

In one embodiment of the invention, the tablet comprises 7-9% by weight tenofovir alafenamide hemifumarate, preferably about 8% by weight tenofovir alafenamide hemifumarate, and the total quantity of degradation products derived from the tenofovir alafenamide hemifumarate is less than about 2%, for instance about 1.7%, after storage for 3 months at 40° C./75% RH in closed conditions.

In another embodiment of the invention, the tablet comprises about 8% by weight tenofovir alafenamide hemifumarate and at least 55% by weight emtricitabine, wherein the total quantity of degradation products derived from the tenofovir alafenamide hemifumarate is less than about 2%, for instance about 1.7%, after storage for 3 months at 40° C./75% RH in closed conditions.

In one embodiment of the invention, the tablet comprises 3-4% by weight tenofovir alafenamide or a pharmaceutically acceptable salt thereof, preferably about 3% by weight tenofovir alafenamide or a pharmaceutically acceptable salt thereof, and the total quantity of degradation products derived from the tenofovir alafenamide or a pharmaceutically acceptable salt thereof is less than about 2.5%, such as less than 2%, for instance about 1.8%, after storage for 3 months at 40° C./75% RH in closed conditions.

In one embodiment of the invention, the tablet comprises 3-4% by weight tenofovir alafenamide hemifumarate, preferably about 3% by weight tenofovir alafenamide hemifumarate, and the total quantity of degradation products derived from the tenofovir alafenamide hemifumarate is less than about 2.5%, such as less than 2%, for instance about 1.8%, after storage for 3 months at 40° C./75% RH in closed conditions.

In a preferred embodiment of the invention, the tablet comprises about 3% by weight tenofovir alafenamide hemifumarate and at least 55% by weight emtricitabine, wherein the total quantity of degradation products derived from the tenofovir alafenamide hemifumarate is less than about 2.5%, such as less than 2%, for instance about 1.8%, after storage for 3 months at 40° C./75% RH in closed conditions. In one embodiment of the invention, the tablet comprises a) tenofovir alafenamide or a pharmaceutically acceptable salt thereof and b) emtricitabine or a pharmaceutically acceptable salt thereof, and the total quantity of degradation products derived from the tenofovir alafenamide or a pharmaceutically acceptable salt thereof is less than about 2%, such as less than 1.5% or less than 1%, after storage for 12 months at 30° C./75% RH in closed conditions.

In one embodiment of the invention, the tablet comprises a) tenofovir alafenamide hemifumarate and b) emtricitabine, and the total quantity of degradation products derived from the tenofovir alafenamide hemifumarate is less than about 2%, such as less than 1.5% or less than 1%, after storage for 12 months at 30° C./75% RH in closed conditions.

In one embodiment of the invention, the tablet comprises 7-9% by weight tenofovir alafenamide or a pharmaceutically acceptable salt thereof, preferably about 8% by weight tenofovir alafenamide or a pharmaceutically acceptable salt thereof, and the total quantity of degradation products derived from the tenofovir alafenamide or a pharmaceutically acceptable salt thereof is less than about 2%, such as less than 1.5% or less than 1%, after storage for 12 months at 30° C./75% RH in closed conditions.

In one embodiment of the invention, the tablet comprises 7-9% by weight tenofovir alafenamide hemifumarate, preferably about 8% by weight tenofovir alafenamide hemifumarate, and the total quantity of degradation products derived from the tenofovir alafenamide hemifumarate is less than about 2%, such as less than 1.5% or less than 1%, after storage for 12 months at 30° C./75% RH in closed conditions.

In another embodiment of the invention, the tablet comprises about 8% by weight tenofovir alafenamide hemifumarate and at least 55% by weight emtricitabine, wherein the total quantity of degradation products derived from the tenofovir alafenamide hemifumarate is less than about 2%, such as less than 1.5% or less than 1%, after storage for 12 months at 30° C./75% RH in closed conditions.

In one embodiment of the invention, the tablet comprises 3-4% by weight tenofovir alafenamide or a pharmaceutically acceptable salt thereof, preferably about 3% by weight tenofovir alafenamide or a pharmaceutically acceptable salt thereof, and the total quantity of degradation products derived from the tenofovir alafenamide or a pharmaceutically acceptable salt thereof is less than about 2%, such as less than 1.5%, after storage for 12 months at 30° C./75% RH in closed conditions.

In one embodiment of the invention, the tablet comprises 3-4% by weight tenofovir alafenamide hemifumarate, preferably about 3% by weight tenofovir alafenamide hemifumarate, and the total quantity of degradation products derived from the tenofovir alafenamide hemifumarate is less than about 2%, such as less than 1.5%, after storage for 12 months at 30° C./75% RH in closed conditions.

In a preferred embodiment of the invention, the tablet comprises about 3% by weight tenofovir alafenamide hemifumarate and at least 55% by weight emtricitabine, wherein the total quantity of degradation products derived from the tenofovir alafenamide hemifumarate is less than about 2%, such as less than 1.5%, after storage for 12 months at 30° C./75% RH in closed conditions.

In one embodiment of the invention, less than 20% by weight of the tablet is croscarmellose sodium. In one embodiment of the invention, less than 10% by weight of the tablet is croscarmellose sodium.

In one embodiment of the invention, less than 40% by weight of the tablet is microcrystalline cellulose. In one embodiment of the invention, less than 30% by weight of the tablet is microcrystalline cellulose. In one embodiment of the invention, less than 26% by weight of the tablet is microcrystalline cellulose.

In one embodiment of the invention, the tablet comprises 200 mg emtricitabine and 11.2 mg tenofovir alafenamide hemifumarate, wherein at least 50% of the total weight of the tablet is emtricitabine and tenofovir alafenamide hemifumarate. In one embodiment of the invention, the tablet comprises 200 mg emtricitabine and 11.2 mg tenofovir alafenamide hemifumarate, wherein at least 50% of the total weight of the tablet is emtricitabine and tenofovir alafenamide hemifumarate, and wherein the excipients consist of croscarmellose sodium, microcrystalline cellulose and magnesium stearate. In one embodiment of the invention, this tablet is coated with a film coating, optionally wherein the film coating is Opadry® II and/or the amount of the coating is 2-4% of the weight of the core of the tablet. In one embodiment of the invention, the total weight of this tablet is 350 mg. In one embodiment of the invention, this tablet is coated and the total weight of this tablet is 360.5 mg.

In one embodiment of the invention, the tablet comprises 200 mg emtricitabine and 11.2 mg tenofovir alafenamide hemifumarate, wherein at least 58% of the total weight of the tablet is emtricitabine and tenofovir alafenamide hemifumarate. In one embodiment of the invention, the tablet comprises 200 mg emtricitabine and 11.2 mg tenofovir alafenamide hemifumarate, wherein at least 58% of the total weight of the tablet is emtricitabine and tenofovir alafenamide hemifumarate, and wherein the excipients consist of croscarmellose sodium, microcrystalline cellulose and magnesium stearate. In one embodiment of the invention, this tablet is coated with a film coating, optionally wherein the film coating is Opadry® II and/or the amount of the coating is 2-4% of the weight of the core of the tablet. In one embodiment of the invention, the total weight of this tablet is 350 mg. In one embodiment of the invention, this tablet is coated and the total weight of this tablet is 360.5 mg.

In one embodiment of the invention, the tablet comprises 200 mg emtricitabine and 11.2 mg tenofovir alafenamide hemifumarate, wherein at least 60% of the total weight of the tablet is emtricitabine and tenofovir alafenamide hemifumarate. In one embodiment of the invention, the tablet comprises 200 mg emtricitabine and 11.2 mg tenofovir alafenamide hemifumarate, wherein at least 60% of the total weight of the tablet is emtricitabine and tenofovir alafenamide hemifumarate, and wherein the excipients consist of croscarmellose sodium, microcrystalline cellulose and magnesium stearate. In one embodiment of the invention, this tablet is coated with a film coating, optionally wherein the film coating is Opadry® II and/or the amount of the coating is 2-4% of the weight of the core of the tablet. In one embodiment of the invention, the total weight of this tablet is 350 mg. In one embodiment of the invention, this tablet is coated and the total weight of this tablet is 360.5 mg.

In one embodiment of the invention, the tablet comprises 200 mg emtricitabine and 11.2 mg tenofovir alafenamide hemifumarate, wherein at least 65% of the total weight of the tablet is emtricitabine and tenofovir alafenamide hemifumarate. In one embodiment of the invention, the tablet comprises 200 mg emtricitabine and 11.2 mg tenofovir alafenamide hemifumarate, wherein at least 65% of the total weight of the tablet is emtricitabine and tenofovir alafenamide hemifumarate, and wherein the excipients consist of croscarmellose sodium, microcrystalline cellulose and magnesium stearate. In one embodiment of the invention, this tablet is coated with a film coating, optionally wherein the film coating is Opadry® II and/or the amount of the coating is 2-4% of the weight of the core of the tablet. In one embodiment of the invention, the total weight of this tablet is 350 mg. In one embodiment of the invention, this tablet is coated and the total weight of this tablet is 360.5 mg.

In one embodiment of the invention, the tablet comprises 200 mg emtricitabine and 28 mg tenofovir alafenamide hemifumarate, wherein at least 50% of the total weight of the tablet is emtricitabine and tenofovir alafenamide hemifumarate. In one embodiment of the invention, the tablet comprises 200 mg emtricitabine and 28 mg tenofovir alafenamide hemifumarate, wherein at least 50% of the total weight of the tablet is emtricitabine and tenofovir alafenamide hemifumarate, and wherein the excipients consist of croscarmellose sodium, microcrystalline cellulose and magnesium stearate. In one embodiment of the invention, this tablet is coated with a film coating, optionally wherein the film coating is Opadry® II and/or the amount of the coating is 2-4% of the weight of the core of the tablet. In one embodiment of the invention, the total weight of this tablet is 350 mg. In one embodiment of the invention, this tablet is coated and the total weight of this tablet is 360.5 mg.

In one embodiment of the invention, the tablet comprises 200 mg emtricitabine and 28 mg tenofovir alafenamide hemifumarate, wherein at least 60% of the total weight of the tablet is emtricitabine and tenofovir alafenamide hemifumarate. In one embodiment of the invention, the tablet comprises 200 mg emtricitabine and 28 mg tenofovir alafenamide hemifumarate, wherein at least 60% of the total weight of the tablet is emtricitabine and tenofovir alafenamide hemifumarate, and wherein the excipients consist of croscarmellose sodium, microcrystalline cellulose and magnesium stearate. In one embodiment of the invention, this tablet is coated with a film coating, optionally wherein the film coating is Opadry® II and/or the amount of the coating is 2-4% of the weight of the core of the tablet. In one embodiment of the invention, the total weight of this tablet is 350 mg. In one embodiment of the invention, this tablet is coated and the total weight of this tablet is 360.5 mg.

In one embodiment of the invention, the tablet comprises 200 mg emtricitabine and 28 mg tenofovir alafenamide hemifumarate, wherein at least 63% of the total weight of the tablet is emtricitabine and tenofovir alafenamide hemifumarate. In one embodiment of the invention, the tablet comprises 200 mg emtricitabine and 28 mg tenofovir alafenamide hemifumarate, wherein at least 63% of the total weight of the tablet is emtricitabine and tenofovir alafenamide hemifumarate, and wherein the excipients consist of croscarmellose sodium, microcrystalline cellulose and magnesium stearate. In one embodiment of the invention, this tablet is coated with a film coating, optionally wherein the film coating is Opadry® II and/or the amount of the coating is 2-4% of the weight of the core of the tablet. In one embodiment of the invention, the total weight of this tablet is 350 mg. In one embodiment of the invention, this tablet is coated and the total weight of this tablet is 360.5 mg.

In one embodiment of the invention, the tablet comprises 200 mg emtricitabine and 28 mg tenofovir alafenamide hemifumarate, wherein at least 65% of the total weight of the tablet is emtricitabine and tenofovir alafenamide hemifumarate. In one embodiment of the invention, the tablet comprises 200 mg emtricitabine and 28 mg tenofovir alafenamide hemifumarate, wherein at least 65% of the total weight of the tablet is emtricitabine and tenofovir alafenamide hemifumarate, and wherein the excipients consist of croscarmellose sodium, microcrystalline cellulose and magnesium stearate. In one embodiment of the invention, this tablet is coated with a film coating, optionally wherein the film coating is Opadry® II and/or the amount of the coating is 2-4% of the weight of the core of the tablet. In one embodiment of the invention, the total weight of this tablet is 350 mg. In one embodiment of the invention, this tablet is coated and the total weight of this tablet is 360.5 mg.

In another embodiment of the invention, the tablets disclosed herein are part of a kit comprising (a) a tablet comprising tenofovir alafenamide or a pharmaceutically acceptable salt thereof, and emtricitabine or a pharmaceutically acceptable salt thereof, and (b) a desiccant (e.g. silica gel).

In one embodiment of the invention, the tablet comprises:

| Ingredient | Mass (mg) |
|---|---|
| Emtricitabine or a salt thereof | 150-250 |
| Tenofovir alafenamide or a salt thereof | 5-35 |
| Croscarmellose sodium | 20-35 |
| Microcrystalline cellulose | 70-120 |
| Magnesium stearate | 1-7 |

In one embodiment of the invention, the tablet of the invention comprises:

| Ingredient | Mass (mg) |
|---|---|
| Emtricitabine | 170-230 |
| Tenofovir alafenamide hemifumarate | 10-32 |
| Croscarmellose sodium | 20-35 |
| Microcrystalline cellulose | 70-120 |
| Magnesium stearate | 1-7 |

In one embodiment of the invention, the tablet of the invention consists of:

| Ingredient | Mass (mg) |
|---|---|
| Emtricitabine | 200 ± 20 |
| Tenofovir alafenamide hemifumarate | 18 ± 10 |
| Croscarmellose sodium | 28 ± 3 |
| Microcrystalline cellulose | 100 ± 13 |
| Magnesium stearate | 5.2 ± 1.1 |

and optionally a film coating.

In one embodiment of the invention, the tablet comprises:

| Ingredient | Mass (mg) |
|---|---|
| Emtricitabine or a salt thereof | 150-250 |
| Tenofovir alafenamide or a salt thereof | 5-15 |
| Croscarmellose sodium | 20-35 |
| Microcrystalline cellulose | 90-120 |
| Magnesium stearate | 1-7 |

In one embodiment of the invention, the tablet of the invention comprises:

| Ingredient | Mass (mg) |
|---|---|
| Emtricitabine | 170-230 |
| Tenofovir alafenamide hemifumarate | 10-15 |
| Croscarmellose sodium | 20-35 |
| Microcrystalline cellulose | 90-120 |
| Magnesium stearate | 1-7 |

In one embodiment of the invention, the tablet of the invention consists of:

| Ingredient | Mass (mg) |
|---|---|
| Emtricitabine | 200 ± 20 |
| Tenofovir alafenamide hemifumarate | 11 ± 1 |
| Croscarmellose sodium | 28 ± 3 |
| Microcrystalline cellulose | 106 ± 11 |
| Magnesium stearate | 5.2 ± 1.1 |

and optionally a film coating.

In one embodiment of the invention, the tablet of the invention consists of:

| Ingredient | Mass (mg) |
|---|---|
| Emtricitabine | 200 ± 10 |
| Tenofovir alafenamide hemifumarate | 11 ± 0.6 |
| Croscarmellose sodium | 28 ± 1.4 |
| Microcrystalline cellulose | 106 ± 5 |
| Magnesium stearate | 5.2 ± 0.5 |

and optionally a film coating.

In one embodiment of the invention, the tablet of the invention consists of:

| Ingredient | Mass (mg) |
|---|---|
| Emtricitabine | 200 |
| Tenofovir alafenamide hemifumarate | 11.2 |
| Croscarmellose sodium | 28.0 |
| Microcrystalline cellulose | 105.56 |
| Magnesium stearate | 5.25 |

and optionally a film coating, for example a film coating comprising Opadry II Gray 85F97517 (a combination of polyvinyl alcohol, polyethylene glycol (PEG), talc, titanium dioxide, iron oxide, black).

In one embodiment of the invention, the tablet of the invention consists of:

| Ingredient | Mass (mg) |
|---|---|
| Intragranular | |
| Emtricitabine | 200 |
| Tenofovir alafenamide hemifumarate | 11.2 |

-continued

| Ingredient | Mass (mg) |
|---|---|
| Croscarmellose sodium | 28 |
| Microcrystalline cellulose | 105.56 |
| Magnesium stearate | 2.625 |
| Extragranular | |
| Magnesium stearate | 2.625 |
| Total core weight | 350 |

and a film coating consisting of Opadry II Gray 85F97517 (which contains 40.0% w/w Polyvinyl Alcohol-part hydrolyzed, 24.74% w/w Titanium Dioxide, 20.2% w/w Macrogol/PEG 3350, 14.8% w/w Talc, and 0.26% w/w Iron Oxide, Black).

In one embodiment of the invention, the tablet comprises:

| Ingredient | Mass (mg) |
|---|---|
| Emtricitabine or a salt thereof | 150-250 |
| Tenofovir alafenamide or a salt thereof | 20-35 |
| Croscarmellose sodium | 20-35 |
| Microcrystalline cellulose | 70-100 |
| Magnesium stearate | 1-7 |

In one embodiment of the invention, the tablet of the invention comprises:

| Ingredient | Mass (mg) |
|---|---|
| Emtricitabine | 170-230 |
| Tenofovir alafenamide hemifumarate | 22-32 |
| Croscarmellose sodium | 20-35 |
| Microcrystalline cellulose | 70-100 |
| Magnesium stearate | 1-7 |

In one embodiment of the invention, the tablet of the invention consists of:

| Ingredient | Mass (mg) |
|---|---|
| Emtricitabine | 200 ± 20 |
| Tenofovir alafenamide hemifumarate | 28 ± 3 |
| Croscarmellose sodium | 28 ± 3 |
| Microcrystalline cellulose | 89 ± 9 |
| Magnesium stearate | 5.2 ± 1.1 |

and optionally a film coating.

In one embodiment of the invention, the tablet of the invention consists of:

| Ingredient | Mass (mg) |
|---|---|
| Emtricitabine | 200 ± 10 |
| Tenofovir alafenamide hemifumarate | 28 ± 1.4 |
| Croscarmellose sodium | 28 ± 1.4 |
| Microcrystalline cellulose | 89 ± 4 |
| Magnesium stearate | 5.2 ± 0.5 |

and optionally a film coating.

In one embodiment of the invention, the tablet of the invention consists of:

| Ingredient | Mass (mg) |
|---|---|
| Emtricitabine | 200 |
| Tenofovir alafenamide hemifumarate | 28 |
| Croscarmellose sodium | 28 |
| Microcrystalline cellulose | 89 |
| Magnesium stearate | 5.3 |

and optionally a film coating, for example a film coating comprising Opadry II Blue 85F105057 (a combination of Polyvinyl alcohol, polyethylene glycol (PEG), talc, titanium dioxide, FD&C blue #2).

In one embodiment of the invention, the tablet of the invention consists of:

| Ingredient | Mass (mg) |
|---|---|
| Emtricitabine | 200.00 |
| Tenofovir alafenamide hemifumarate | 28.00 |
| Croscarmellose sodium | 28.00 |
| Microcrystalline cellulose | 88.70 |
| Magnesium stearate | 5.25 |

and optionally a film coating, for example a film coating comprising Opadry II Blue 85F105057 (a combination of Polyvinyl alcohol, polyethylene glycol (PEG), talc, titanium dioxide, FD&C blue #2).

In one embodiment of the invention, the tablet of the invention consists of:

| Ingredient | Mass (mg) |
|---|---|
| Intragranular | |
| Emtricitabine | 200.00 |
| Tenofovir alafenamide hemifumarate | 28.00 |
| Croscarmellose sodium | 28.00 |
| Microcrystalline cellulose | 88.70 |
| Magnesium stearate | 2.625 |
| Extragranular | |
| Magnesium stearate | 2.625 |
| Total core weight | 350 |

and a film coating consisting of Opadry II Blue 85F105057 (which contains 40.0% w/w Polyvinyl Alcohol-part hydrolyzed, 23.32% w/w Titanium Dioxide, 20.2% w/w Macrogol/PEG 3350, 14.8% w/w Talc, and 1.68% w/w FD&C Blue #2/Indigo Carmine Aluminum Lake).

In one embodiment of the invention, the tablet of the invention consists of:

| Ingredient | Mass (mg) |
|---|---|
| Intragranular | |
| Emtricitabine | 200 |
| Tenofovir alafenamide hemifumarate | 28 |
| Croscarmellose sodium | 28 |
| Microcrystalline cellulose | 89 |
| Magnesium stearate | 2.6 |
| Extragranular | |
| Magnesium stearate | 2.6 |
| Total core weight | 350 |

and a film coating consisting of Opadry II Blue 85F105057 (which contains 40.0% w/w Polyvinyl Alcohol-part hydrolyzed, 23.32% w/w Titanium Dioxide, 20.2% w/w Macrogol/PEG 3350, 14.8% w/w Talc, and 1.68% w/w FD&C Blue #2/Indigo Carmine Aluminum Lake).

Manufacturing Methods

Methods for producing the compositions and dosage forms (in particular tablets) described herein are also provided. In some embodiments, the method comprises blending emtricitabine and tenofovir alafenamide hemifumarate with excipients, followed by compression. In some embodiments, emtricitabine and tenofovir alafenamide hemifumarate are first co-blended and granulated with excipients, for example by dry granulation. This step involves, in certain embodiments, roller compaction and/or milling. In some embodiments, the granulation of the co-blended emtricitabine and tenofovir alafenamide hemifumarate are further combined with extragranular excipients, including but not limited to magnesium stearate, then compressed.

In some embodiments, the method comprises (a) compressing the rilpivirine or a pharmaceutically acceptable salt thereof as a first layer, and (b) compressing the tenofovir alafenamide or a pharmaceutically acceptable salt thereof and emtricitabine or a pharmaceutically acceptable salt thereof as a second layer. The first layer and second layer may be compressed separately and subsequently combined. However, more typically, the first layer is formed by compression and subsequently the second layer is compressed onto the first layer. The inventors have discovered that the choice of layer order in the tabletting of multilayer tablets may have an impact on the properties of the tablets (e.g. the adhesion of the layers within the tablet). Accordingly, compressing rilpivirine or a pharmaceutically acceptable salt thereof as a first layer e.g. to a first layer weight of about 300 mg, and then compressing tenofovir alafenamide or a pharmaceutically acceptable salt thereof and emtricitabine or a pharmaceutically acceptable salt thereof as a second layer e.g. to a second layer weight of about 350 mg, is advantageous, because of the enhanced compressibility and flow of the first layer. This is contrary to the process used to produce Complera®/Eviplera® commercially, in which the rilpivirine-containing layer is compressed as the second layer.

In some embodiments, a tablet is provided wherein the first layer obtainable by a method of (a) compressing the rilpivirine or a pharmaceutically acceptable salt thereof as a first layer, and (b) compressing the tenofovir alafenamide or a pharmaceutically acceptable salt thereof and emtricitabine or a pharmaceutically acceptable salt thereof as a second layer. In other embodiments, invention tablet is provided wherein the second layer obtainable by a method of (a) compressing the rilpivirine or a pharmaceutically acceptable salt thereof as a first layer, and (b) compressing the tenofovir alafenamide or a pharmaceutically acceptable salt thereof and emtricitabine or a pharmaceutically acceptable salt thereof as a second layer.

Typically, the methods will include a step of coating the tablet cores after compression, e.g. with a film coating as described above.

In general, tableting methods are well known in the art of pharmacy. Techniques and formulations generally are found in Remington's Pharmaceutical Sciences (Mack Publishing Co., Easton, PA), which is hereby incorporated by reference herein in its entirety.

A tablet can be made by compression or molding, optionally with one or more excipients. Compressed tablets may be prepared by compressing in a suitable machine the active ingredient in a free-flowing form such as a powder or granules, optionally mixed with excipients.

Therapeutic Methods

The solid oral dosage forms (in particular tablets) disclosed herein may be used to treat or prevent HIV (e.g. HIV-1). In some embodiments, the solid oral dosage forms (in particular tablets) disclosed herein may be used to treat or prevent HIV-1 or HIV-2.

In certain embodiments, the solid oral dosage forms (in particular tablets) disclosed herein may be used to treat HIV (e.g. HIV-1). In some embodiments, the solid oral dosage forms (in particular tablets) disclosed herein may be used to treat HIV-1 or HIV-2.

In certain embodiments, the solid oral dosage forms (in particular tablets) disclosed herein may be used to prevent HIV (e.g. HIV-1). In some embodiments, the solid oral dosage forms (in particular tablets) disclosed herein may be used to prevent HIV-1 or HIV-2.

Accordingly, methods for treating a subject having HIV are provided, comprising administering a solid oral dosage form of the invention (in particular a tablet) to the subject. Similarly, a solid oral dosage form of the invention (in particular a tablet) is provided for use in such treatment methods. The invention also provides the use of rilpivirine or a pharmaceutically acceptable salt thereof, tenofovir alafenamide or a pharmaceutically acceptable salt thereof, and emtricitabine or a pharmaceutically acceptable salt thereof, in the manufacture of an oral dosage form of the invention (in particular a tablet) for treating HIV. In some embodiments, the invention provides the use of tenofovir alafenamide or a pharmaceutically acceptable salt thereof, and emtricitabine or a pharmaceutically acceptable salt thereof, in the manufacture of an oral dosage form of the invention (in particular a tablet) for treating HIV.

In certain embodiments, a method of treating an HIV infection in a human having or at risk of having the infection is provided, wherein the method includes administering to the human the solid oral dosage forms disclosed herein. Similarly, a method of preventing HIV infection in a human having or at risk of becoming infected infection is provided, wherein the method includes administering to the human the solid oral dosage forms disclosed herein.

In another embodiment, a use of the solid oral dosage forms disclosed herein for the treatment of an HIV infection in a human having or at risk of having the infection is provided. Similarly, a use of the solid oral dosage forms disclosed herein for the prevention of an HIV infection in a human having or at risk of having the infection is provided.

In another embodiment, a method of using a solid oral dosage form disclosed herein in therapy is provided. In particular, a method of treating the proliferation of the HIV virus, treating AIDS, or delaying the onset of AIDS or ARC symptoms in a mammal (e.g., a human, such as for example men having sex with men or transsexual women having sex with men) is provided, comprising administering to the mammal a solid oral dosage form disclosed herein.

In a particular embodiment, the solid oral dosage forms disclosed herein are provided for use to prevent HIV infection from taking hold if the individual is exposed to the virus and/or to keep the virus from establishing a permanent infection and/or to prevent the appearance of symptoms of the disease and/or to prevent the virus from reaching detectable levels in the blood, for example for pre-exposure prophylaxis (PrEP) or post-exposure prophylaxis (PEP). Accordingly, in certain embodiments, methods for reducing the risk of acquiring HIV (e.g., HIV-1 and/or HIV-2) are provided. For example, methods for reducing the risk of acquiring HIV (e.g., HIV-1 and/or HIV-2) comprise administration of the solid dosage forms disclosed herein. In certain specific embodiments, methods for reducing the risk of acquiring HIV (e.g., HIV-1 and/or HIV-2) comprise administration of a solid oral dosage form disclosed herein in combination with safer sex practices. In certain embodiments, methods for reducing the risk of acquiring HIV (e.g., HIV-1 and/or HIV-2) comprise administration to an individual at risk of acquiring HIV. Examples of individuals at high risk for acquiring HIV include, without limitation, an individual who is at risk of sexual transmission of HIV.

In certain embodiments, the reduction in risk of acquiring HIV is at least about 40%, 50%, 60%, 70%, 80%, 90%, or 95%. In certain embodiments, the reduction in risk of acquiring HIV is at least about 75%. In certain embodiments, the reduction in risk of acquiring HIV is about 80%, 85%, or 90%.

In another embodiment, the use of a solid oral dosage form disclosed herein for the manufacture of a medicament for the treatment of an HIV infection in a human being having or at risk of having the infection is disclosed. Similarly, in another embodiment, the use of a solid oral dosage form disclosed herein for the manufacture of a medicament for the prevention of an HIV infection in a human being having or at risk of having the infection is disclosed.

In another embodiment, an article of manufacture comprising a solid oral dosage form disclosed herein; and packaging material comprising a label which indicates that the solid oral dosage form can be used to treat infection by HIV is disclosed. Similarly, in another embodiment, an article of manufacture comprising a solid oral dosage form disclosed herein; and packaging material comprising a label which indicates that the solid oral dosage form can be used to prevent HIV infection is disclosed.

The methods disclosed herein involve administering an oral dosage form disclosed herein (in particular a tablet) to the subject, typically a human, and will generally involve repeated administrations, typically once daily. The treatment may be prophylactic or therapeutic treatment.

In certain embodiments, the methods disclosed herein involve repeated administrations at intervals less than once daily. For example, in certain embodiments, the methods disclosed herein involve administration of the oral dosage forms disclosed herein every other day, five times per week, four times per week, three times per week, two times per week, or one time per week.

In certain embodiments, the methods disclosed herein involve administration prior to and/or after an event that would expose the individual to HIV or that would otherwise increase the individual's risk of acquiring HIV, e.g., as pre-exposure prophylaxis (PrEP) and/or as post-exposure prophylaxis (PEP). Examples of events that could increase an individual's risk of acquiring HIV include, without limitation, no condom use during anal intercourse with an HIV positive partner or a partner of unknown HIV status; anal intercourse with more than 3 sex partners; exchange of money, gifts, shelter or drugs for anal sex; sex with male partner and diagnosis of sexually transmitted infection; and no consistent use of condoms with sex partner known to be HIV positive.

In certain embodiments, e.g., when administered as PrEP, the solid oral dosage forms disclosed herein are administered 2 to 72 hours, 2 to 48 hours, 2 to 24 hours, or 2 to 12 hours prior to an event that would increase the individual's risk of acquiring HIV (e.g., prior to sex or other exposure to the HIV virus). In some embodiments, the solid oral dosage forms disclosed herein are administered within 72 hours, 60 hours, 48 hours, 24 hours, 12 hours, 9 hours, 6 hours, 4 hours, 3 hours, 2 hours or 1 hour prior to an event that would increase the individual's risk of acquiring HIV (e.g., prior to sex or other exposure to the HIV virus). In certain embodiments, when the solid oral dosage forms disclosed herein are administered prior to an event that would increase the individual's risk of acquiring HIV, they are administered daily prior to the event. In certain embodiments, when the solid oral dosage forms disclosed herein are administered prior to an event that would increase the individual's risk of acquiring HIV, they are administered one to three times prior to the event.

In certain embodiments, e.g., when administered as part of a PrEP regimen or as PEP, the solid oral dosage forms disclosed herein are administered 2 to 48 hours, 2 to 36 hours, 2 to 24 hours, or 2 to 12 hours following an event that would increase the individual's risk of acquiring HIV (e.g., following sex or other exposure to the HIV virus). In certain embodiments, e.g., when administered as PEP, the solid oral dosage forms disclosed herein are administered for 7 days, 14 days, 21 days, 28 days, 30 days, or 45 days following an event that would increase the individual risk of acquiring HIV (e.g., following sex or other exposure to the HIV virus). In certain embodiments, e.g., when administered as PEP, the solid oral dosage forms disclosed herein are administered for 30 days following an event that would increase the individual risk of acquiring HIV (e.g., following sex or other exposure to the HIV virus). In certain embodiments, the solid oral dosage forms disclosed herein are administered less than 1 hour, 2 hours, 3 hours, 4, hours, 5 hours, 6 hours, 7 hours, 8 hours, 9 hours, 12 hours, 18 hours, 24 hours, 36 hours, or 48 hours following an event that would increase the individual's risk of acquiring HIV (e.g., following sex or other exposure to the HIV virus). In certain other embodiments, the solid oral dosage forms disclosed herein are administered for 1 day, 2 days, 3, days 4 days, or 5 days following an event that would increase the individual's risk of acquiring HIV (e.g., following sex or other exposure to the HIV virus). In certain embodiments, when the solid oral dosage forms disclosed herein are administered following to an event that would increase the individual's risk of acquiring HIV, they are administered daily following to the event. In certain embodiments, when the solid oral dosage forms disclosed herein are administered following an event that would increase the individual's risk of acquiring HIV, they are administered one to three times following the event. In certain embodiments, when the solid oral dosage forms disclosed herein are administered following to an event that would increase the individual's risk of acquiring HIV, they are administered once following the event.

In certain embodiments, e.g., when administered as PrEP, the solid oral dosage forms disclosed herein are administered prior to an event that would increase the individual's risk of acquiring HIV (e.g., prior to sex) and following the event. For example, in certain embodiments, e.g., when administered as PrEP, the solid oral dosage forms disclosed herein are administered 2 to 72 hours, 2 to 48 hours, 2 to 24 hours, or 2 to 12 hours prior to an event that would increase the individual's risk of acquiring HIV (e.g., prior to sex) and 2 to 48 hours, 2 to 36 hours, 2 to 24 hours, or 2 to 12 hours following the event. For example, in some embodiments, one or more (e.g., one, two, or three) solid oral dosage forms disclosed herein are administered one to three days prior to an event that would increase the individual's risk of acquiring HIV (e.g., prior to sex) and once per day for a period of one to five days following the event. In some embodiments, one or more (e.g., one, two, or three) solid oral dosage forms disclosed herein are administered 2 to 24 hours prior to an event that would increase the individual's risk of acquiring HIV (e.g., prior to sex) and one or more times (e.g., one, two, or three times) 2 to 48 hours following the event. In some embodiments, the solid oral dosage forms disclosed herein are administered once per week, twice per week, three times per week, four times per week, or five times per week and one or more times (e.g., one, two, or three times) 2 to 48 hours following an event that would increase the individual's risk of acquiring HIV (e.g., prior to sex). In one embodiment, the oral solid dosage forms disclosed herein are administered twice per week (one composition (i.e., tablet) per day) and once (one composition) following an event that increases the individual's risk of acquiring HIV (e.g., one tablet within 24 hours of exposure, such as following sex).

General

The term "fed" in relation to administration of a solid oral dosage form to a human subject means administration of the dosage form orally under fed conditions (moderate fat meal) e.g. administration within about 30 minutes of the human consuming a standardized meal of about 300 to 600 calories and about 10 to about 15 grams of fat.

The term "substantially free" in relation to the presence of a given component within e.g. a composition means that less than 5% by weight of the composition (e.g. less than 1% by weight of the composition) is that given component. The word "substantially" does not exclude "completely" e.g. a composition which is "substantially free" from Y may be completely free from Y. Where necessary, the word "substantially" may be omitted from the definition of the invention.

The term "segregated" as used in relation to certain components (e.g. A and B) within a tablet means that those components are physically discrete such that the presence of one component (e.g. A) does not substantially affect the stability in storage of the other component(s) (e.g. B) from which it is segregated. Typically, when components are segregated in a tablet then they will be present in separate layers in a multilayer tablet. By way of example, components A and B may be present in separate layers in a multilayer tablet, wherein (a) the layer containing component A is substantially free of component B and (b) the layer containing component B is substantially free of component A. The separate layers may be in contact with each other or may be separated e.g. by one or more additional layers.

The term "comprise" and variations thereof, such as "comprises" and "comprising", are to be construed in an open, inclusive sense, that is as "including, but not limited to".

The term "between" with reference to two values includes those two values e.g. the range "between" 10 mg and 20 mg encompasses e.g. 10, 11, 12, 13, 14, 15, 16, 17, 18, 19 and 20 mg.

As used herein the term "about" is understood by the person of skill in the art to reflect the variability in the numerical value it modifies. Values expressed herein are understood to include a range of variability. To reflect this variability, any numerical value used herein incorporates this variability. As such, numerical values used herein encompass that value stated, as well as the value as modified with "about." In certain embodiments, the term "about" in relation to a numerical value x is optional and means, for example, x±10%, x±5%, or x±1%.

"% w/w" means the weight of a component as a percentage of the total weight of e.g. a layer or dosage form in which the component is present. For example, a composition comprising "5% w/w X" refers to a composition in which the weight of component X is 5% of the total weight of the composition.

Reference throughout this specification to "one embodiment" or "an embodiment" means that a particular feature, structure or characteristic described in connection with the embodiment is included in at least one embodiment provided herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The term "pharmaceutically acceptable" with respect to a substance refers to that substance which is generally regarded as safe and suitable for use without undue toxicity, irritation, allergic response, and the like, commensurate with a reasonable benefit/risk ratio.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, PA, (2005), at p. 732, Table 38-5, both of which are hereby incorporated by reference herein.

As used herein, the term "salts" includes co-crystals. The term "co-crystal" refers to a crystalline compound comprising two or more molecular components, e.g, wherein proton transfer between the molecular components is partial or incomplete. Accordingly, the term "pharmaceutically acceptable salt" as used herein encompasses salts and co-crystals as defined herein.

The term "solvate" means a molecular complex comprising a compound and one or more pharmaceutically acceptable solvent molecules. Examples of solvent molecules include water and $C_{1-6}$ alcohols, e.g. ethanol. When the solvate is water, the term "hydrate" may be used.

"Treating" and "treatment" of a disease include the following:

(1) preventing or reducing the risk of developing the disease, i.e. causing the clinical symptoms of the disease not to develop in a subject that may be exposed to or predisposed to the disease but does not yet experience or display symptoms of the disease, (2) inhibiting the disease, i.e. arresting or reducing the development of the disease or its clinical symptoms, and (3) relieving the disease, i.e. causing regression of the disease or its clinical symptoms.

The term "effective amount" refers to an amount that may be effective to elicit the desired biological or medical response, including the amount of a compound that, when administered to a subject for treating a disease, is sufficient to effect such treatment for the disease. The effective amount will vary depending on the compound, the disease and its severity and the age, weight, etc. of the subject to be treated. The effective amount can include a range of amounts.

EXAMPLES

The invention will now be illustrated by the following non-limiting examples.

Example 1—Emtricitabine/Tenofovir Alafenamide Hemifumarate Tablets

The emtricitabine/tenofovir alafenamide hemifumarate formulation was initially developed to a target emtricitabine dose of 200 mg per tablet and target tenofovir alafenamide doses of 25 mg and 40 mg per tablet. Antiviral activity was measured by change in baseline in HIV-1 RNA and DAVG11. Statistically greater reductions in HIV-1 RNA and DAVG11 were observed for the 25 mg tenofovir alafenamide single-agent tablet and the 40 mg tenofovir alafenamide single agent tablet as compared to the tenofovir disoproxil fumarate single-agent tablet, supporting further clinical investigation of 25 mg and 40 mg tenofovir alafenamide.

Emtricitabine/tenofovir alafenamide 200/25 mg and emtricitabine/tenofovir alafenamide 200/40 mg fixed-dose combination tablet formulations containing 200 mg emtricitabine and 25 mg (tablet A) or 40 mg emtricitabine/tenofovir alafenamide (tablet B) as emtricitabine/tenofovir alafenamide were developed and manufactured for a Phase 1 clinical study. The composition of emtricitabine/tenofovir alafenamide 200/25 mg and 200/40 mg fixed-dose combination tablet formulations evaluated were:

| Component | Tablet A Emtricitabine/ tenofovir alafenamide 200/25 mg (mg/tablet) | Tablet B Emtricitabine/ tenofovir alafenamide 200/40 mg (mg/tablet) |
|---|---|---|
| Intragranular | | |
| Emtricitabine | 200.0 | 200.0 |
| Tenofovir Alafenamide hemifumarate | 28.0 | 44.9 |
| Microcrystalline Cellulose | 179.2 | 162.36 |
| Croscarmellose Sodium | 27.0 | 27.0 |
| Magnesium Stearate | 3.375 | 3.375 |
| Extragranular | | |
| Croscarmellose Sodium | 9.0 | 9.0 |
| Magnesium Stearate | 3.375 | 3.375 |
| Total Tablet Core Weight | 450 | 450 |
| Film-Coating | | |
| Opadry II White 85F18422 | 13.5 | 13.5 |

Emtricitabine/tenofovir alafenamide 200/25 mg (tablet A) and 200/40 mg (tablet B) tablets evaluated were manufactured using a dry granulation/tablet compression/film-coating process train. Dry granulation by roller compaction was selected as the means of combining emtricitabine and tenofovir alafenamide in order to minimize exposure of tenofovir alafenamide to moisture during the granulation process. The overall manufacturing process consisted of co-blending and lubricating emtricitabine and tenofovir alafenamide with intragranular excipients, followed by roller compaction and milling. The resulting emtricitabine/tenofovir alafenamide granules were then blended and lubricated with extragranular excipients to produce the emtricitabine/tenofovir alafenamide final powder blend, which was compressed into 450 mg core tablets that were subsequently film-coated with Opadry II White 85F18422.

Example 2—Stability of Emtricitabine/Tenofovir Alafenamide Hemifumarate Tablets The stability of tablets A and B from Example 1 was evaluated at the long-term storage condition of 25° C./60% RH for 24 months and at the accelerated condition of 40° C./75% RH for 6 months. Stability results for emtricitabine and tenofovir alafenamide hemifumarate indicated that limited degradation of emtricitabine occurred for either emtricitabine/tenofovir alafenamide hemifumarate tablet strength at any storage condition. After 6 months at 40° C./75% RH, 4.2% of total tenofovir alafenamide hemifumarate impurities products were observed for tablet A and 3.0% total tenofovir alafenamide hemifumarate impurities products were observed for tablet B.

Dissolution of emtricitabine and tenofovir alafenamide hemifumarate from these tablets did not change. Tablets stored at all conditions exhibited ≥98% release of both active agents at all storage times (monitored using USP apparatus II, in 500 ml of 50 mM sodium citrate pH 5.5, at 37° C. and paddle speed of 75 rpm). Moisture contents of these tablets ranged from 1.3 to 2.5% over the course of the stability study. Overall, these stability data demonstrate that tablet A and tablet B packaged in HDPE bottles with 2 g of desiccant remain physically and chemically stable under accelerated conditions (40° C./75% RH) for 6 months and under long-term storage (25° C./60% RH) for up to 24 months.

Example 3—Excipient Ranging Studies

Formulation development studies were performed by designing, manufacturing, and testing eleven prototype monolayer co-dry granulation emtricitabine/tenofovir alafenamide hemifumarate tablet formulations. These formulations were evaluated for influence of excipient identity and relative composition on tenofovir alafenamide hemifumarate chemical stability. Compositions of the eleven formulations are summarized in the following table:

| | Lot Number | | | | | | | | | | |
|---|---|---|---|---|---|---|---|---|---|---|---|
| | A | B | C | D | E | F | G | H | I | J | K |
| | Formulation Composition (% w/w) | | | | | | | | | | |
| Emtricitabine | 44.44 | 44.44 | 44.44 | 44.44 | 44.44 | 44.44 | 44.44 | 44.44 | 44.44 | 57.14 | 57.14 |
| Tenofovir alafenamide hemifumarate | 2.49 | 2.49 | 2.49 | 2.49 | 2.49 | 2.49 | 2.49 | 6.23 | 6.23 | 3.20 | 8.01 |
| Microcrystalline Cellulose | 43.57 | 21.79 | 4.37 | 23.57 | 23.57 | 45.57 | 43.56 | 39.83 | 47.83 | 30.16 | 25.35 |
| Dibasic Calcium Phosphate, Anhydrous | — | 21.79 | 39.20 | — | — | — | — | — | — | — | — |
| Lactose Monohydrate | — | — | — | 20.00 | — | — | — | — | — | — | — |
| Mannitol | — | — | — | — | 20.00 | — | — | — | — | — | — |
| Croscarmellose Sodium | 8.00 | 8.00 | 8.00 | 8.00 | 8.00 | 6.00 | — | 8.00 | — | 8.00 | 8.00 |
| Crospovidone | — | — | — | — | — | — | 8.00 | — | — | — | — |
| Magnesium Stearate | 1.50 | 1.50 | 1.50 | 1.50 | 1.50 | 1.50 | 1.50 | 1.50 | 1.50 | 1.50 | 1.50 |
| Total Tablet Core Weight (mg) | 450 | 450 | 450 | 450 | 450 | 450 | 450 | 450 | 450 | 350 | 350 |
| Opadry II Gray 85F97517 | — | — | — | — | — | — | — | 3 | 3 | — | 3 |
| Opadry II Blue 85F105057 | 3 | 3 | 3 | 3 | 3 | 3 | 3 | — | — | 3 | — |

30 tablets were packaged in 60 mL HDPE bottles with 2 g of desiccant and polyester coil. Bottles were induction-sealed with a PP cap.

"—" excipient not included in the composition

The following formulation attributes were examined:

- Filler type and excipient matrix composition: microcrystalline cellulose, microcrystalline cellulose and lactose monohydrate, microcrystalline cellulose and mannitol, or microcrystalline cellulose and dibasic calcium phosphate anhydrous.
- Disintegrant type and level: croscarmellose sodium or crospovidone.
- Tenofovir alafenamide hemifumarate drug load: tenofovir alafenamide hemifumarate concentrations of 2.49% and 3.20% w/w in emtricitabine/tenofovir alafenamide hemifumarate 200/10 mg tablets and tenofovir alafenamide hemifumarate concentrations of 6.23% and 8.01% w/w in emtricitabine/tenofovir alafenamide 200/25 mg tablets.

All film-coated tablets were packaged as a 30 count configuration in 60 mL HDPE bottle with 2 grams of silica gel desiccant and a polyester coil. HDPE bottles were induction-sealed using a polypropylene (PP) cap with an aluminum-faced liner. Chemical stability was monitored over 3 months at 40° C./75% RH. For the 5 formulations tested (batches A-E), the total tenofovir alafenamide hemifumarate degradation products (compared to initial) increased by 0.7 to 1.7% after 1 month and by 2.3 to 2.7% after 3 months. Overall, the filler system did not significantly influence tenofovir alafenamide hemifumarate degradation after 3 months at the accelerated conditions.

Example 4—Effect of Tenofovir Alafenamide Hemifumarate Loading on Stability in Emtricitabine/Tenofovir Alafenamide Hemifumarate Tablets The impact of tenofovir alafenamide hemifumarate drug load on tenofovir alafenamide hemifumarate stability in emtricitabine/tenofovir alafenamide 200/10 mg and 200/25 mg tablets was evaluated using a range of tenofovir alafenamide hemifumarate drug loads from 2.49% to 8.01% with concomitant adjustment in microcrystalline cellulose content. Emtricitabine/tenofovir alafenamide 200/10 mg tablet formulations contained 2.49% w/w tenofovir alafenamide hemifumarate or 3.20% w/w tenofovir alafenamide hemifumarate, while emtricitabine/tenofovir alafenamide 200/25 mg tablet formulations contained 6.23% w/w tenofovir alafenamide hemifumarate or 8.01% w/w tenofovir alafenamide hemifumarate. Higher drug loads were achieved by reducing the total tablet weight from 450 mg to 350 mg.

Tenofovir alafenamide hemifumarate chemical stability as a function of drug load is summarized in the table below:

| Tenofovir alafenamide hemifumarate Degradation Products (%) | Tenofovir alafenamide hemifumarate concentration (% w/w) | | | | | | | | | | | | | |
|---|---|---|---|---|---|---|---|---|---|---|---|---|---|---|
| | Tenofovir alafenamide hemifumarate 2.49% | | | Tenofovir alafenamide hemifumarate 3.20% | | | | Tenofovir alafenamide hemifumarate 6.23% | | | Tenofovir alafenamide hemifumarate 8.01% | | | |
| | Lot Number | | | | | | | | | | | | | |
| | A | | | J | | | | H | | | K | | | |
| | Condition: 40° C./75% RH | | | | | | | | | | | | | |
| | Time Point (months) | | | Time Point (months) | | | | Time Point (months) | | | Time Point (months) | | | |
| | 0 | 1 | 3 | 0 | 1 | 3 | 6 | 0 | 1 | 3 | 0 | 1 | 3 | 6 |
| PMPA | 0.22 | 0.60 | 1.32 | 0.26 | 0.49 | 0.82 | 2.04 | 0.23 | 0.49 | 1.00 | 0.21 | 0.48 | 0.77 | 1.33 |
| PMPA Anhydride | 0.29 | 0.43 | 1.21 | 0.29 | 0.37 | 0.76 | 1.97 | 0.28 | 0.37 | 0.85 | 0.27 | 0.37 | 0.67 | 1.24 |
| Monophenyl PMPA | nd | 0.06 | 0.07 | 0.05 | 0.05 | 0.04 | 0.13 | 0.06 | 0.05 | 0.07 | nd | 0.06 | 0.07 | 0.10 |
| PMPA Monoamidate | 0.08 | 0.11 | 0.14 | 0.10 | 0.11 | 0.13 | 0.18 | 0.06 | 0.08 | 0.11 | 0.07 | 0.14 | 0.16 | 0.09 |
| Phenol | nd | nd | 0.07 | nd | nd | nd | 0.08 | nd | tr | 0.07 | 0.09 | tr | 0.05 | 0.07 |
| Unspecified[b] | nd | 0.11 | 0.16 | nd | nd | 0.12 | 0.22 | nd | 0.05 | 0.07 | nd | 0.06 | nd | 0.11 |
| Total tenofovir alafenamide hemifumarate Deg. (%) | 0.6 | 1.3 | 3.0 | 0.7 | 1.0 | 1.8 | 4.6 | 0.6 | 1.0 | 2.2 | 0.6 | 1.1 | 1.7 | 2.9 |

nd: not detected (<0.025%)

tr: trace (0.025% < impurity < 0.05%)

[a] 30 tablets were packaged in 60 mL HDPE bottles with 2 g of desiccant and polyester coil. Bottles were induction-sealed with a PP cap.

[b] represents sum of all unspecified degradation products/impurities

Emtricitabine/tenofovir alafenamide 200/10 mg tablets containing 2.49% w/w tenofovir alafenamide hemifumarate exhibited increases in total tenofovir alafenamide hemifumarate degradation products of 0.7% and 2.4% after 1 and 3 months, respectively. Emtricitabine/tenofovir alafenamide 200/10 mg tablets containing 3.20% w/w tenofovir alafenamide hemifumarate exhibited increases in total tenofovir alafenamide hemifumarate degradation products of 0.3% and 1.1% after 1 and 3 months, respectively. Increasing the tenofovir alafenamide hemifumarate drug load from 2.49% w/w to 3.20% w/w tenofovir alafenamide hemifumarate resulted in a 50% reduction in total tenofovir alafenamide hemifumarate degradation products after 3 months under accelerated conditions.

Emtricitabine/tenofovir alafenamide 200/25 mg tablets containing 8.01% w/w tenofovir alafenamide hemifumarate demonstrated better tenofovir alafenamide hemifumarate chemical stability than tablets containing 6.23% w/w tenofovir alafenamide hemifumarate. After 3 months, total tenofovir alafenamide hemifumarate degradation products in emtricitabine/tenofovir alafenamide 200/25 mg tablets increased by 1.5% for the 6.23% w/w tenofovir alafenamide hemifumarate formulation and 1.1% for the 8.01% w/w tenofovir alafenamide hemifumarate formulation. Based on the results of the tenofovir alafenamide hemifumarate drug load study, tenofovir alafenamide hemifumarate contents of 3.20% w/w and 8.01% w/w were selected for the emtricitabine/tenofovir alafenamide 200/10 mg and 200/25 mg fixed dose combination tablets, respectively.

FIG. 1 shows a plot of the increase in tenofovir alafenamide hemifumarate-related degradation products as a function of tenofovir alafenamide hemifumarate loading at 1 month and 3 months (at 40° C./75% RH).

Example 5

As a result of the excipient and drug load evaluations, two formulations (emtricitabine/tenofovir alafenamide 200/10 mg, tablet C; and emtricitabine/tenofovir alafenamide 200/25 mg, tablet D) were developed for use in further studies. The compositions of these formulations shown in the following table:

| Component | Tablet C Emtricitabine/ tenofovir alafenamide 200/10 mg (mg/tablet) | Tablet D Emtricitabine/ tenofovir alafenamide 200/25 mg (mg/tablet) |
|---|---|---|
| Intragranular | | |
| Emtricitabine | 200.00 | 200.00 |
| Tenofovir Alafenamide Hemifumarate | 11.20 | 28.00 |
| Microcrystalline Cellulose | 105.56 | 88.70 |
| Croscarmellose Sodium | 28.00 | 28.00 |
| Magnesium Stearate | 2.625 | 2.625 |
| Extragranular | | |
| Magnesium Stearate | 2.625 | 2.625 |
| Total Tablet Core Weight | 350 | 350 |
| Film-Coating | | |
| Opadry II Gray 85F97517 | 10.5 | — |
| Opadry II Blue 85F105057 | — | 10.5 |

Figure 10:
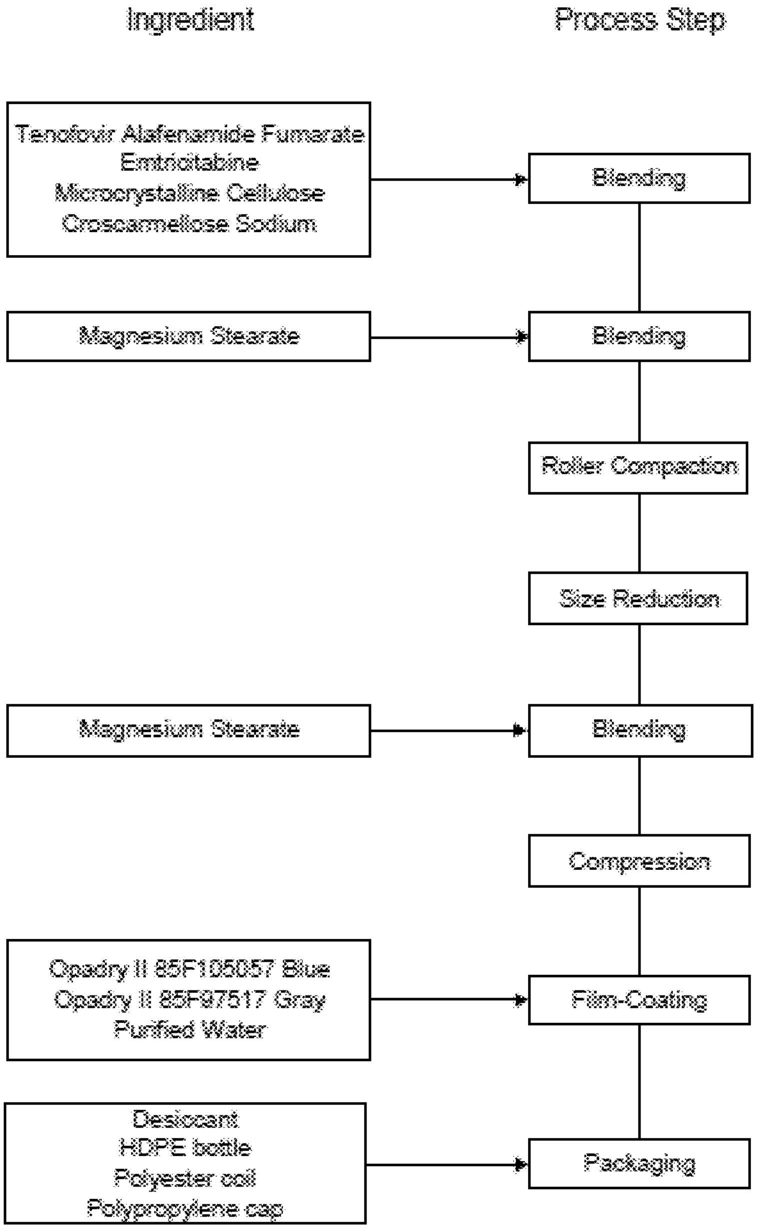
FIG. 10 is a flow diagram illustrating the preparation of a tablet formulation of emtricitabine and tenofovir alafenamide hemifumarate.

Emtricitabine and tenofovir alafenamide hemifumarate were co-blended with microcrystalline cellulose and croscarmellose sodium, followed by lubrication with magnesium stearate. The roller compaction pre-blend was then roller compacted and milled using an oscillating mill. The resultant granules were lubricated with magnesium stearate and compressed into 350 mg tablet cores which that were subsequently film coated. A flow diagram illustrating the process by which tablets C and D were prepared is shown in FIG. 10.

Example 6

Tenofovir alafenamide hemifumarate undergoes solid-state hydrolysis and therefore the inclusion of desiccant in the primary package is included to control the level of moisture in emtricitabine/tenofovir alafenamide hemifumarate tablets. Packaging development was performed on tablets C and D to evaluate the impact of desiccant amount on the chemical stability of tenofovir alafenamide hemifumarate in emtricitabine/tenofovir alafenamide hemifumarate tablets during storage.

Tablets C and D were packaged at 30 count in 60 mL HDPE bottles with either 2 or 3 grams of desiccant and a polyester coil, and sealed with an induction seal. Chemical stability was monitored for up to 6 months at 40° C./75% RH.

Tenofovir alafenamide hemifumarate-related total degradation products in tablet C after 6 months under accelerated conditions were 3.9% and 3.3% for bottles packaged with 2 g and 3 g of desiccant, respectively. In comparison, Tenofovir alafenamide hemifumarate-related total degradation products in tablet D were 2.3% and 2.4% for bottles containing 2 g and 3 g desiccant, respectively.

Example 7—Emtricitabine/Tenofovir Alafenamide Hemifumarate Bioequivalence Studies Randomized, open-label, single-dose, 2-way, crossover studies were performed to determine:

- Study 1: the bioequivalence of emtricitabine and TAF, administered as F/TAF fixed-dose combination tablet (tablet C) simultaneously with elvitegravir and cobicistat or as E/C/F/TAF fixed-dose combination tablet.
- Study 2: the bioequivalence of emtricitabine and TAF, administered as F/TAF fixed-dose combination tablet (tablet D) or as E/C/F/TAF fixed-dose combination tablet.
- Study 3: the bioequivalence of emtricitabine and TAF, administered as F/TAF fixed-dose combination tablet (tablet D) and emtricitabine and TAF from co-administration of Emtriva® (emtricitabine) capsules and TAF single-agent tablets.

Duration of Treatment

Subjects were randomized to one of two treatment sequences (AB or BA) and received a single dose of one of the following treatments (A or B) on days 1 and 7 (studies 1 and 2) or days 1 and 15 (study 3):

Study 1

Treatment A: Single dose of F/TAF (200/10 mg) fixed-dose combination tablet (tablet C) administered simultaneously with EVG 150 mg and COBI 150 mg tablets orally under fed conditions.

Treatment B: Single dose of E/C/F/TAF (150/150/200/10 mg) fixed-dose combination tablet administered orally under fed conditions.

Study 2

Treatment A: Single dose of F/TAF (200/25 mg) fixed-dose combination tablet (tablet D) administered orally under fed conditions.

Treatment B: Single dose of E/C/F/TAF (150/150/200/10 mg) fixed-dose combination tablet administered orally under fed conditions.

Study 3

Treatment A: Single dose of F/TAF (200/25 mg) fixed-dose combination tablet (tablet D) administered orally under fed conditions.

Treatment B: Single dose of Emtriva® 200 mg capsule plus a single TAF 25 mg tablet administered orally under fed conditions.

Studies 1 and 2: In each study, the total duration of the study was 22 days. There was a 6 day washout period between dosing on days 1 and 7, and a 14 day follow-up period.

Study 3: The total duration of the study was 29 days. Doses were administered on days 1 and 15 and there was a 14 day follow-up period.

Criteria for Evaluation

The following plasma pharmacokinetic parameters were calculated: $C_{max}$, $T_{max}$, $C_{last}$, $t_{1/2}$, $AUC_{last}$, $AUC_{inf}$, % $AUC_{exp}$, $V_z$/F, CL/F.

Statistical Methods

Studies 1 and 2

Pharmacokinetics: Plasma concentrations and PK parameters were listed and summarized by treatment group using descriptive statistics. In addition, a parametric analysis of variance using a mixed-effects model appropriate for a crossover design was fitted to the natural logarithmic transformation of the PK parameters ($AUC_{inf}$, $AUC_{last}$, and $C_{max}$). Two-sided 90% confidence intervals (CIs) were constructed for the ratio of geometric least-squares means (GLSMs) of each PK parameter for emtricitabine and tenofovir alafenamide hemifumarate. Bioequivalence of emtricitabine and tenofovir alafenamide hemifumarate in the F/TAF fixed-dose combination (tablet C/tablet D) to the emtricitabine and tenofovir alafenamide hemifumarate components in E/C/F/TAF fixed-dose combination was concluded if the 90% CI of the GLSM (geometric least-squares mean) ratio of the pharmacokinetic parameters for each analyte between two formulations fell within the prespecified bioequivalence boundary of 80% to 125%.

Study 3

Pharmacokinetics: Plasma concentrations and PK parameters were listed and summarized by treatment group using descriptive statistics. In addition, the geometric mean, 95% confidence interval (CI) and the mean and standard deviation (SD) of the natural-log transformed values were presented for individual subject PK parameter data.

For evaluation of bioequivalence of F/TAF and FTC+TAF, the PK parameters (natural-log transformed $AUC_{inf}$, $AUC_{last}$, and $C_{max}$) were compared. A parametric analysis of variance using a mixed-effects model was filled to the natural log-transformed values of PK parameters. The 90% CIs were provided for the geometric mean ratios (GMRs) of PK parameters between pairs of interest. It was concluded that the formulations were bioequivalent if the 90% CIs of the GMRs for selected PK parameters (i.e., $AUC_{inf}$, $AUC_{last}$, and $C_{max}$) fell within the prespecified bioequivalence boundary of 80% to 125%.

Results

Study 1

A total of 100 patients were randomized and received at least one dose of study drug. 98 patients completed the study.

Statistical comparisons of emtricitabine and TAF pharmacokinetic parameters between F/TAF 200/10 mg (tablet C) co-administered with EVG 150 mg and COBI 150 mg and E/C/F/TAF are shown in the table below:

| TAF PK Parameter | N | Test Mean (CV %) | N | Reference Mean (CV %) | GLSM Ratio (Test/ Reference) (%) | 90% CI (%) |
|---|---|---|---|---|---|---|
| F/TAF (200/10 mg) + E + C (Test) vs E/C/F/TAF (150/150/200/10 mg) (Reference) | | | | | | |

-continued

| | N | Test Mean (CV %) | N | Reference Mean (CV %) | GLSM Ratio (Test/ Reference) (%) | 90% CI (%) |
|---|---|---|---|---|---|---|
| $AUC_{last}$ (h · ng/mL) | 97 | 336.6 (33.9) | 99 | 340.2 (33.8) | 97.96 | 94.69, 101.34 |
| $AUC_{inf}$ (h · ng/mL) | 97 | 351.8 (31.0) | 99 | 354.1 (32.9) | 98.34 | 94.81, 101.99 |
| $C_{max}$ (ng/mL) | 97 | 301.6 (48.8) | 99 | 310.3 (48.7) | 96.86 | 89.36, 104.99 |

| Emtricitabine PK Parameter | N | Test Mean (CV %) | N | Reference Mean (CV %) | GLSM Ratio (Test/ Reference) (%) | 90% CI (%) |
|---|---|---|---|---|---|---|
| F/TAF (200/10 mg) + E + C (Test) vs E/C/F/TAF (150/150/200/10 mg) (Reference) | | | | | | |
| $AUC_{last}$ (h · ng/mL) | 97 | 10159.2 (17.2) | 99 | 10086.8 (15.9) | 99.84 | 98.41, 101.29 |
| $AUC_{inf}$ (h · ng/mL) | 97 | 10535.1 (27.0) | 99 | 10294.4 (15.8) | 100.67 | 98.24, 103.16 |
| $C_{max}$ (ng/mL) | 97 | 1660.8 (20.6) | 99 | 1662.6 (19.1) | 99.57 | 96.78, 102.44 |

The GLSM ratios and corresponding 90% CIs of $AUC_{last}$, $AUC_{inf}$, and $C_{max}$ for emtricitabine and tenofovir alafenamide were contained within the 80% to 125% boundary criteria specified for bioequivalence.

Study 2

A total of 56 patients were randomized and received at least one dose of study drug. 54 patients completed the study.

Statistical comparisons of emtricitabine and TAF pharmacokinetic parameters between F/TAF 200/25 mg (tablet D) and E/C/F/TAF are shown in the table below:

| TAF PK Parameter | N | Test Mean (CV %) | N | Reference Mean (CV %) | GLSM Ratio (Test/ Reference) (%) | 90% CI (%) |
|---|---|---|---|---|---|---|
| F/TAF (200/25 mg) vs E/C/F/TAF (150/150/200/10 mg) (Reference) | | | | | | |
| $AUC_{last}$ (h · ng/mL) | 116 | 374.0 (43.4) | 116 | 369.3 (40.6) | 100.32 | 96.48, 104.31 |
| $AUC_{inf}$ (h · ng/mL) | 95 | 396.4 (42.6) | 97 | 389.5 (39.3) | 98.54 | 94.61, 102.62 |
| $C_{max}$ (ng/mL) | 116 | 280.5 (62.9) | 116 | 267.8 (59.8) | 103.63 | 95.46, 112.49 |

| Emtricitabine PK Parameter | N | Test Mean (CV %) | N | Reference Mean (CV %) | GLSM Ratio (Test/ Reference) (%) | 90% CI (%) |
|---|---|---|---|---|---|---|
| F/TAF (200/25 mg) vs E/C/F/TAF (150/150/200/10 mg) (Reference) | | | | | | |
| $AUC_{last}$ (h · ng/mL) | 116 | 9423.9 (19.3) | 116 | 10475.3 (19.7) | 90.01 | 88.88, 91.16 |
| $AUC_{inf}$ (h · ng/mL) | 116 | 9654.6 (19.3) | 116 | 10706.6 (19.6) | 90.20 | 89.06, 91.35 |
| $C_{max}$ (ng/mL) | 116 | 1577.4 (26.8) | 116 | 1601.7 (19.6) | 97.26 | 94.57, 100.03 |

The GLSM ratios and corresponding 90% CIs of $AUC_{last}$, $AUC_{inf}$, and $C_{max}$ for emtricitabine and tenofovir alafenamide were contained within the 80% to 125% boundary criteria specified for bioequivalence.

Study 3

A total of 116 patients were randomized, received at least one dose of study drug and completed the study.

Statistical comparisons of emtricitabine and TAF pharmacokinetic parameters between F/TAF 200/25 mg (tablet D) and Emtriva® 200 mg capsules co-administered with TAF 25 mg tablets are shown in the table below:

| | GLSMs by treatment: Test (F/TAF) Mean (N = 55) | GLSMs by treatment: Reference (FTC + TAF) Mean (N = 55) | GLSM Ratio (Test/Reference) (%) | 90% CI (%) |
|---|---|---|---|---|
| TAF PK Parameter | | | | |
| $AUC_{last}$ (h · ng/mL) | 245.91 | 239.48 | 102.68 | 95.78, 110.09 |
| $AUC_{inf}$ (h · ng/mL) | 254.18[a] | 240.33[b] | 105.77 | 97.26, 115.01 |
| $C_{max}$ (ng/mL) | 209.36 | 226.11 | 92.59 | 82.31, 104.16 |

| | Test (F/TAF) Mean (CV %) | Reference (FTC + TAF) Mean (CV %) | GLSM Ratio (Test/Reference) (%) | 90% CI (%) |
|---|---|---|---|---|
| Emtricitabine PK Parameter | | | | |
| $AUC_{last}$ (h · ng/mL) | 9049.70 | 9410.78 | 96.16 | 94.29, 98.08 |
| $AUC_{inf}$ (h · ng/mL) | 9259.49 | 9636.68 | 96.09 | 94.24, 97.96 |
| $C_{max}$ (ng/mL) | 1813.87 | 1727.84 | 104.98 | 100.75, 109.39 |

[a]N = 43
[b]N = 48

The GLSM ratios and corresponding 90% CIs of $AUC_{last}$, $AUC_{inf}$, and $C_{max}$ for emtricitabine and tenofovir alafenamide were contained within the 80% to 125% boundary criteria specified for bioequivalence.

Conclusions

These studies demonstrate that:

- Emtricitabine and TAF from F/TAF 200/10 mg (tablet C) co-administered with EVG and COBI single-agent tablets were bioequivalent to the exposures of emtricitabine and TAF from the reference treatment of E/C/F/TAF.
- Emtricitabine and TAF from F/TAF 200/25 mg (tablet D) were bioequivalent to the exposures of emtricitabine and TAF from the reference treatment of E/C/F/TAF.
- Emtricitabine and TAF from F/TAF 200/25 mg (tablet D) were bioequivalent to the exposures of emtricitabine and TAF from the reference treatment of the co-administration of an Emtriva® capsule 200 mg, co-administered with a TAF single-agent 25 mg tablet.

Figure 2:
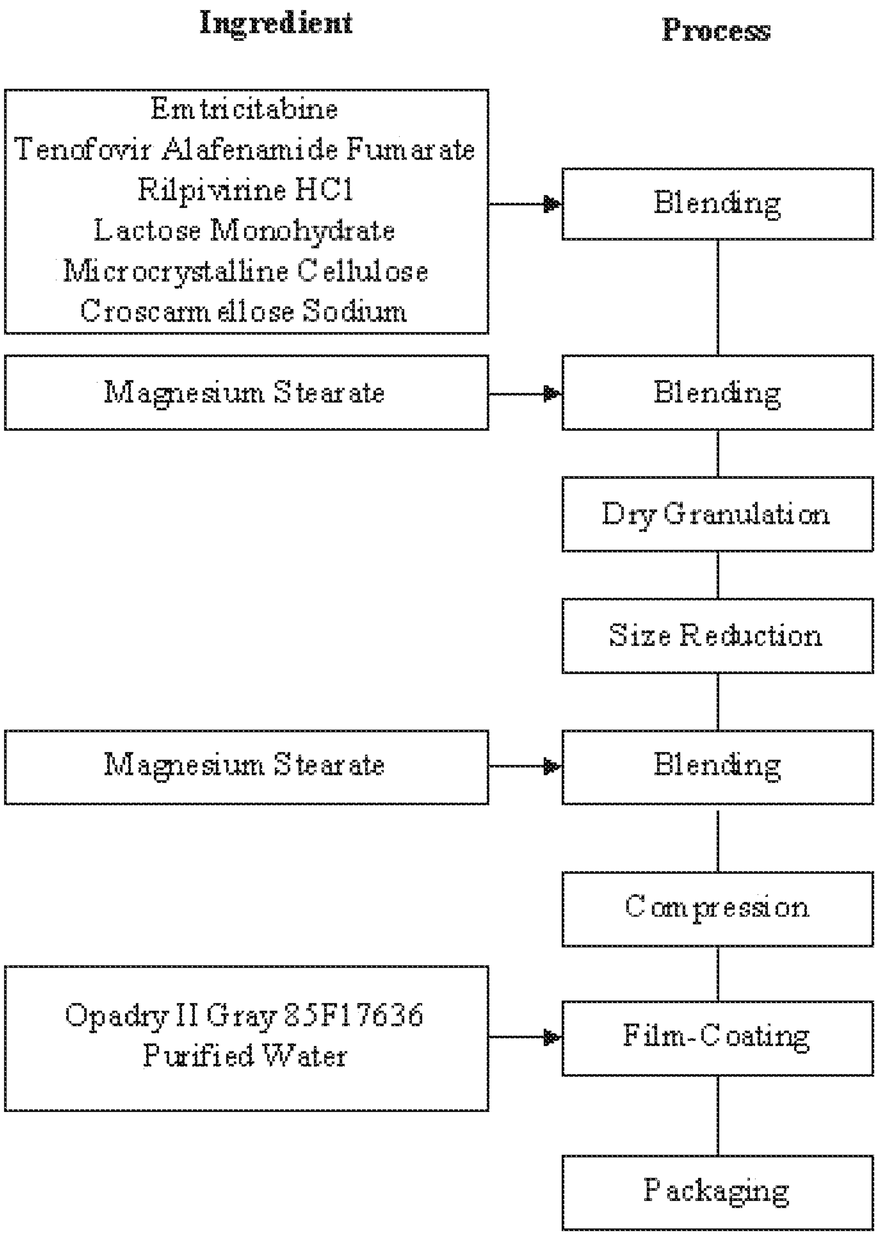
FIG. 2 is a flow diagram illustrating the preparation of a monolayer tablet formulation of emtricitabine, rilpivirine HCl and tenofovir alafenamide hemifumarate.

Example 8—Emtricitabine/Rilpivirine HCl/Tenofovir Alafenamide Hemifumarate Monolayer Tablets A mono-layer formulation (tablet F4) of emtricitabine, rilpivirine HCl and tenofovir alafenamide hemifumarate was prepared by co-dry granulation. FIG. 2 is a flow diagram illustrating the preparation of this formulation. The composition of the co-granulated formulation is shown in the table below:

| Component | Mass (mg/tablet) |
|---|---|
| Emtricitabine | 200.0 |
| Rilpivirine HCl | 27.5 |
| Tenofovir alafenamide hemifumarate | 28.0 |
| Microcrystalline cellulose | 69.9 |
| Croscarmellose sodium | 25.5 |
| Lactose | 69.9 |
| Magnesium Stearate | 4.2 |
| Total Core Weight | 425 |

Example 9—Tenofovir Alafenamide Hemifumarate Stability Studies

Figure 3A:
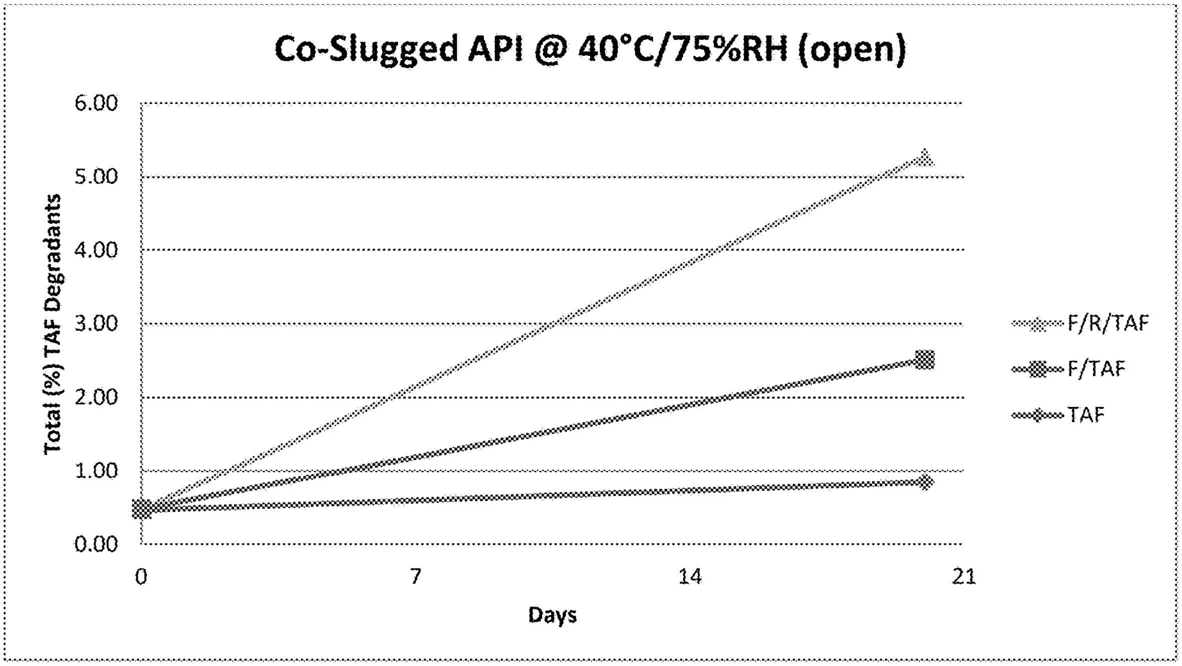
FIGS. 3A and B illustrate the impact on the stability of tenofovir alafenamide hemifumarate of the presence of (i) emtricitabine, and (ii) emtricitabine and rilpivirine HCl.
Figure 3B:
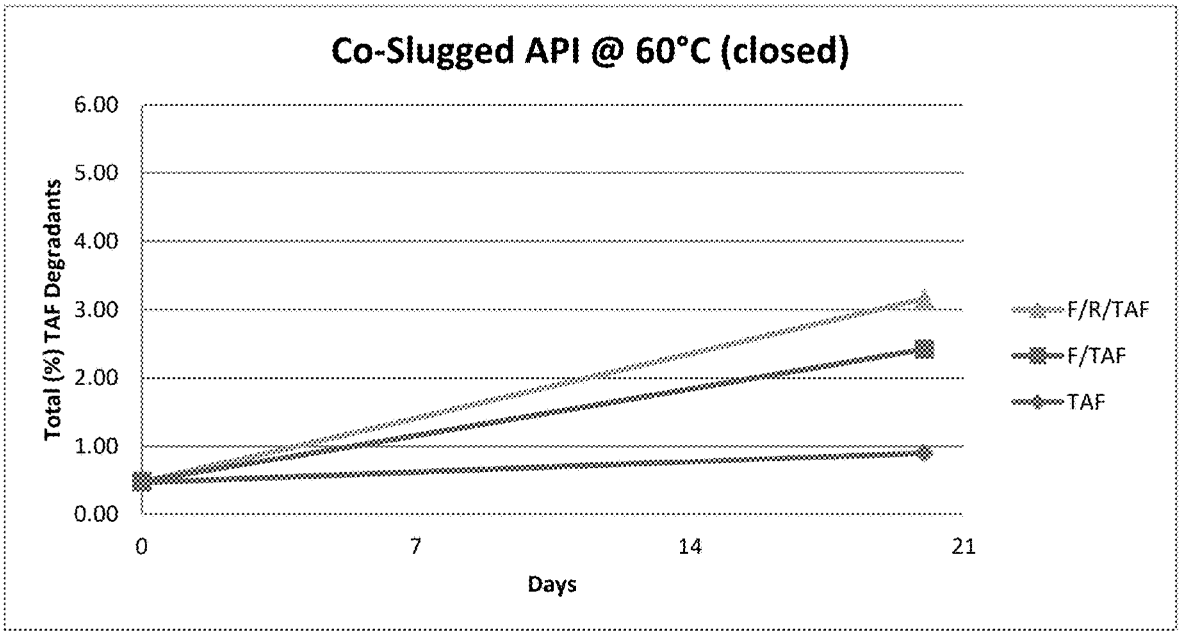
FIG. 3B shows the total degradation of tenofovir alafenamide hemifumarate at 60° C. under closed conditions.

Studies were conducted to assess the stability of tenofovir alafenamide hemifumarate in the presence of (a) emtricitabine, and (b) emtricitabine and rilpivirine HCl. These data are presented in FIGS. 3A and B. FIG. 3A shows the total degradation of tenofovir alafenamide hemifumarate at 40° C./75% RH in open conditions (i.e., unsealed containers with no desiccant present). FIG. 3B shows the total degradation of tenofovir alafenamide hemifumarate at 60° C. in closed conditions. These data show that the rate of degradation of tenofovir alafenamide hemifumarate is increased in the presence of emtricitabine, and is further increased in the presence of both emtricitabine and rilpivirine HCl.

Figure 4:
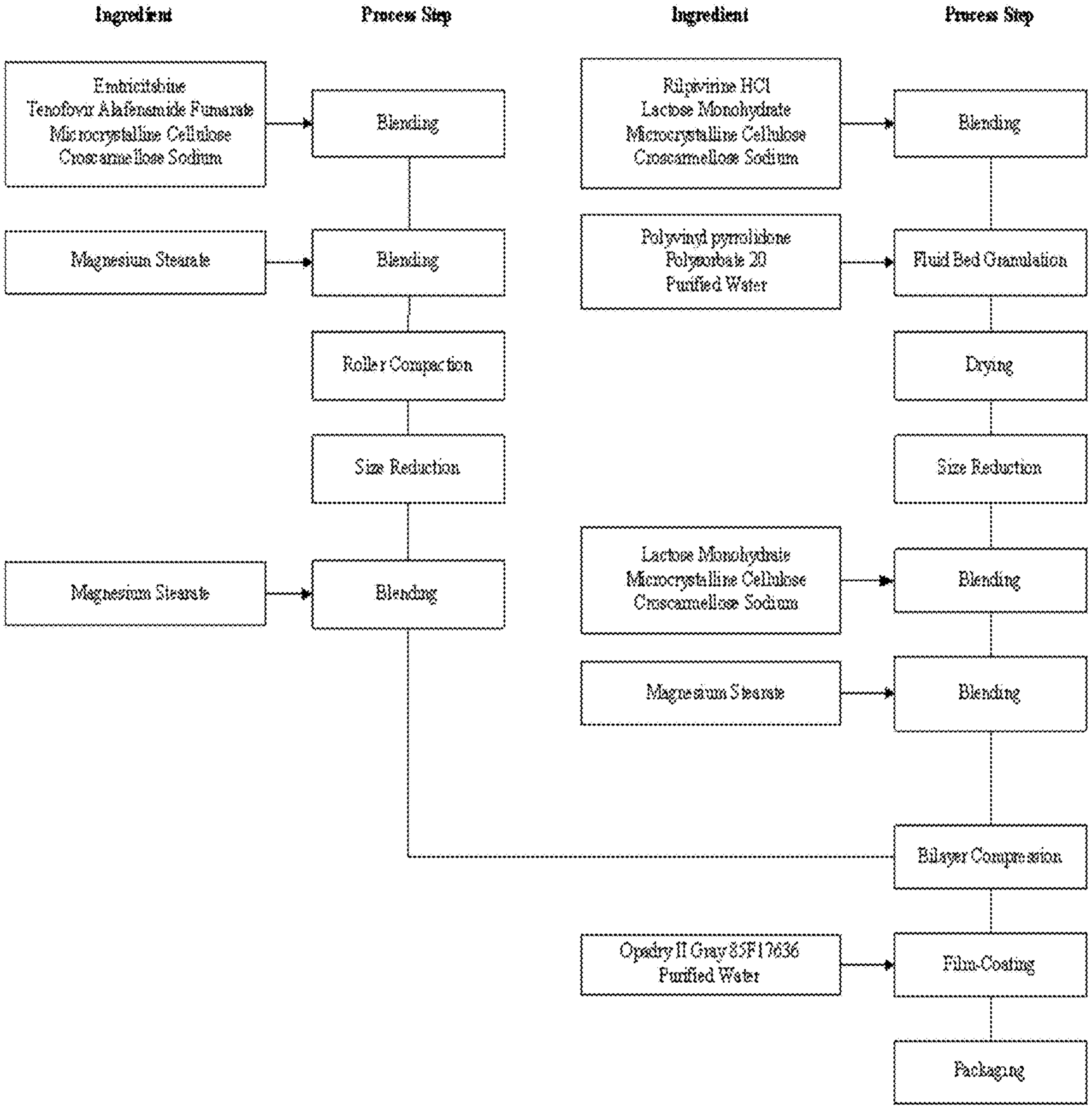
FIG. 4 is a flow diagram illustrating the preparation of a bilayer tablet formulation of emtricitabine, rilpivirine HCl and tenofovir alafenamide hemifumarate.

Example 10—Emtricitabine/Rilpivirine HCl/Tenofovir Alafenamide Hemifumarate Bilayer Tablets A bilayer formulation (tablet F1) of emtricitabine, rilpivirine HCl and tenofovir alafenamide hemifumarate was prepared using the method described in Example 15. FIG. 4 is a flow diagram illustrating the preparation of bilayer tablets. The composition of the formulation is summarized in the table below:

| | Bilayer tablet F1 (mg/tablet) | |
|---|---|---|
| Ingredient | Rilpivirine HCl Layer | Emtricitabine/tenofovir alafenamide hemifumarate Layer |
| Emtricitabine | | 200.0 |
| Rilpivirine HCl | 27.5 | |
| Tenofovir alafenamide hemifumarate | | 28.0 |
| MCC | 60.0 | 88.7 |
| CCS | 16.1 | 28.0 |
| Lactose | 189.8 | |
| Povidone | 3.25 | |
| Starch | | |
| Polysorbate 20 | 0.35 | |
| Magnesium Stearate | 3 | 5.2 |
| Layer Weight | 300 | 350 |
| Tablet Core Weight | 650 | |

Example 11—Dissolution Studies

Figure 5:
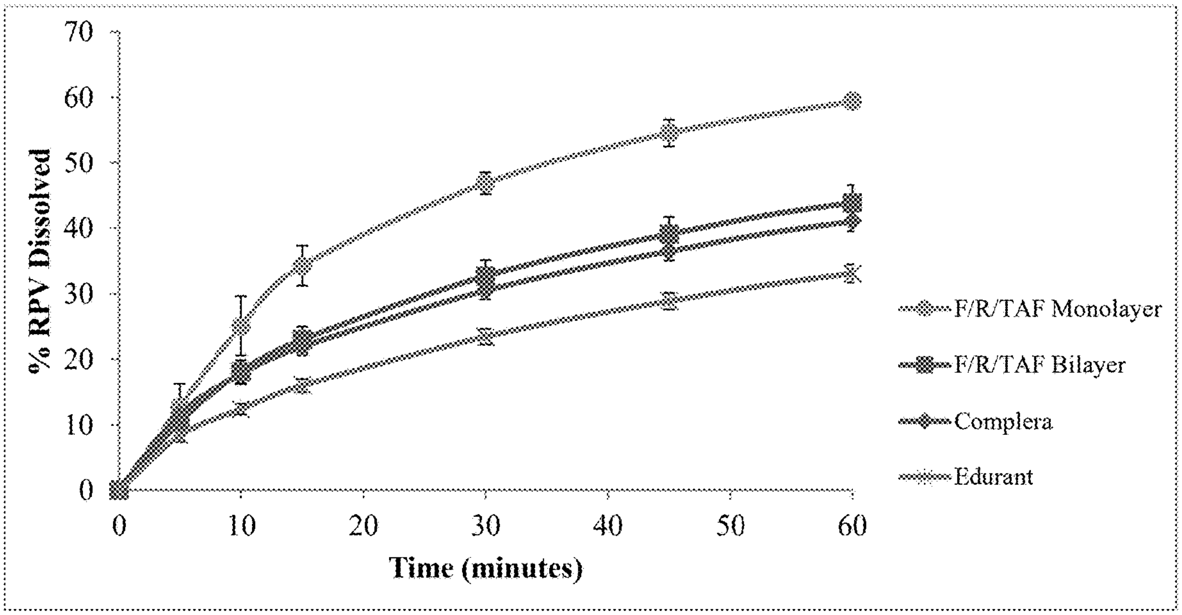
FIG. 5 shows the results of studies carried out on a bilayer tablet formulation of emtricitabine, rilpivirine HCl and tenofovir alafenamide hemifumarate and a monolayer formulation of emtricitabine, rilpivirine HCl and tenofovir alafenamide hemifumarate to assess the dissolution of rilpivirine, as compared to the dissolution of rilpivirine from COMPLERA® and EDURANT®.

Studies were carried out to assess the dissolution profiles of tablets F1 and F4 and to compare these with the dissolution profiles of COMPLERA® and EDURANT®. Dissolution of rilpivirine HCl was measured using USP Apparatus II, in 1000 ml of pH 4.5 sodium acetate with 2% polysorbate 20, at 37° C. and paddle speed of 75 rpm. The results are shown in FIG. 5. These data show that while the bilayer formulation (tablet F1) had comparable rilpivirine HCl dissolution to COMPLERA® and EDURANT®, the monolayer formulation (tablet F4) exhibited enhanced rilpivirine HCl dissolution.

Figure 6A:
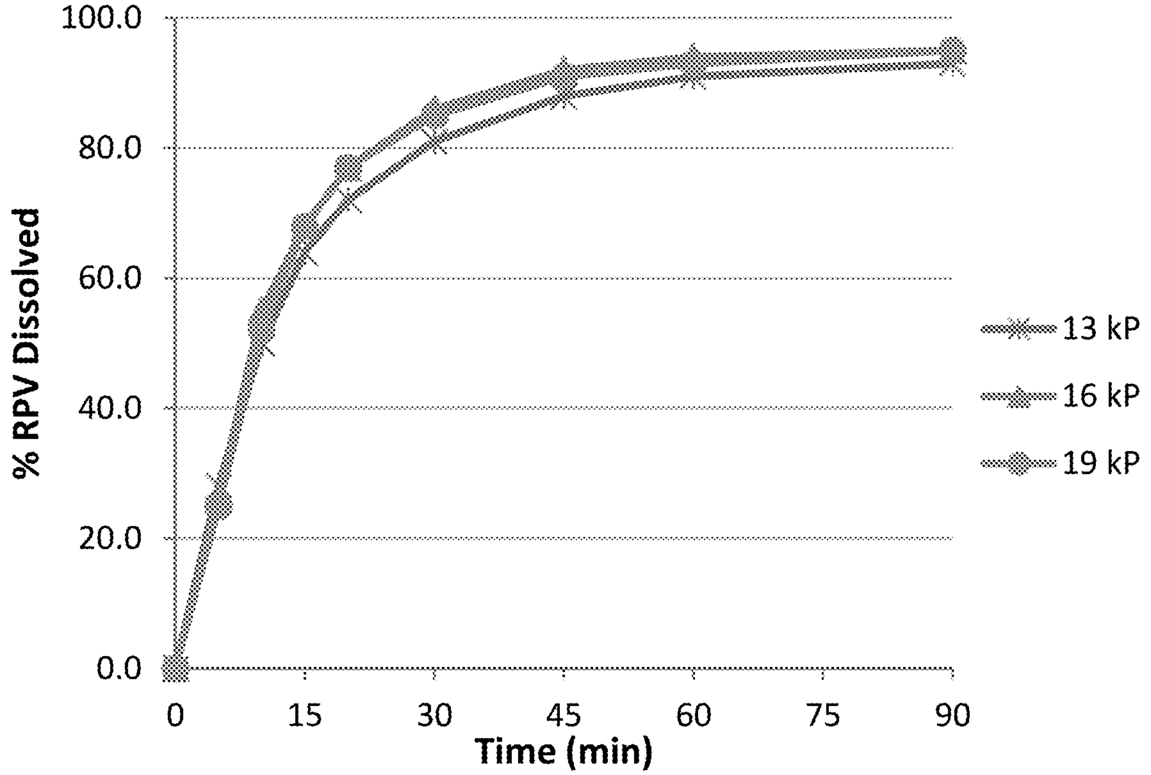
FIGS. 6A, B and C show the results of studies carried out on a bilayer tablet formulation to assess the dissolution of rilpivirine HCl, emtricitabine and tenofovir alafenamide hemifumarate, respectively, as a function of tablet hardness (i.e. at a tablet hardness of 13, 16 and 19 kP.
Figure 6B:
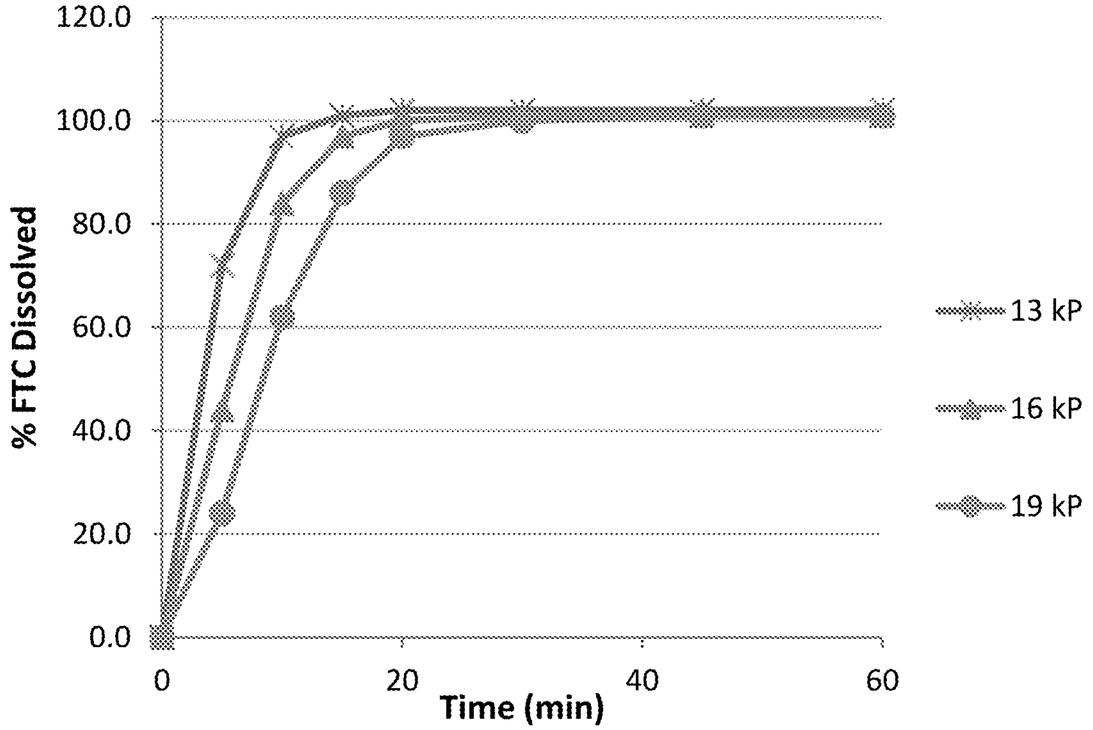
Figure 6C:
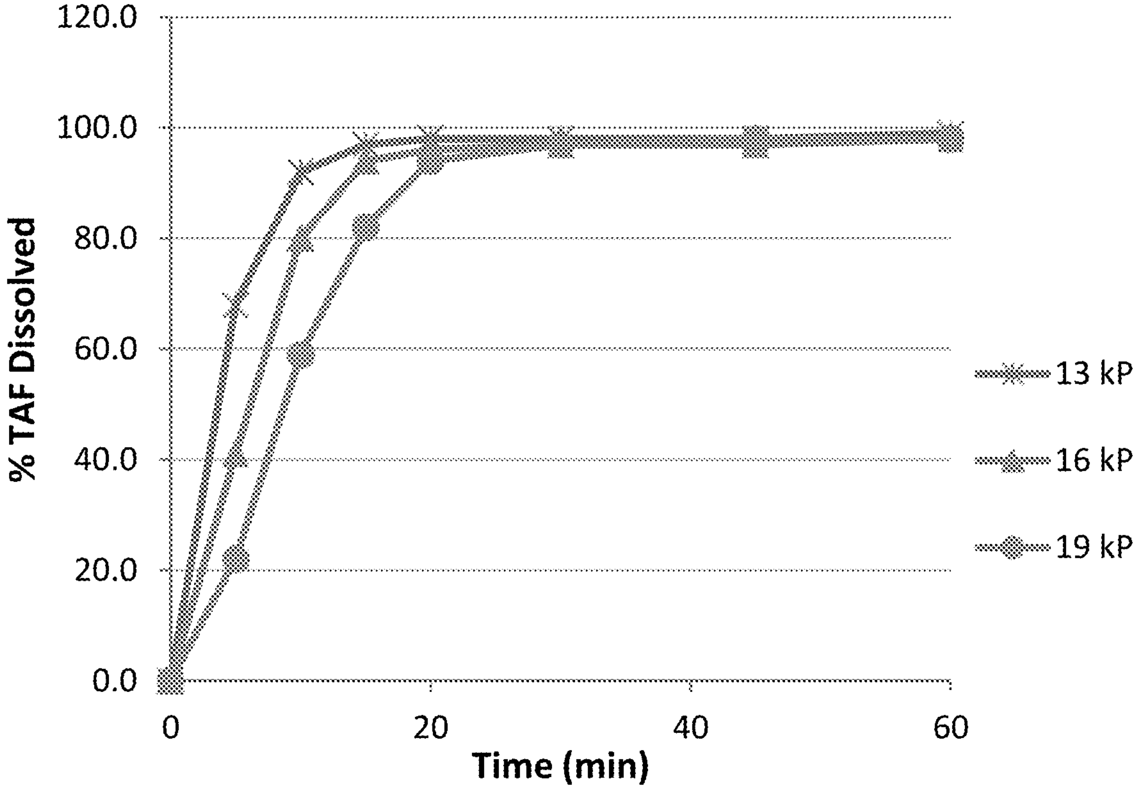

FIGS. 6A, B and C shows the results of studies carried out on a bilayer formulation (F1) to assess how the tablet hardness affects the dissolution of rilpivirine HCl, emtricitabine and tenofovir alafenamide hemifumarate, respectively (i.e. at 13, 16 and 19 kP). Dissolution of rilpivirine HCl in these experiments was measured using USP Apparatus II, in 1000 ml of 0.01N HCl with 0.5% polysorbate 20, at 37° C. and paddle speed of 75 rpm. Dissolution of emtricitabine and tenofovir alafenamide hemifumarate was monitored using USP apparatus II, in 500 ml of 50 mM sodium citrate pH 5.5, at 37° C. and paddle speed of 75 rpm. These data show that all tablets exhibited acceptable dissolution across the selected tablet hardness range (13-19 kP).

Example 12—Emtricitabine/Rilpivirine/Tenofovir Alafenamide Tablet Formulation

The following tablet (tablet E) was selected for use in bioequivalence studies:

| Rilpivirine HCl Layer | Weight (mg/tablet) | % w/w (in layer) |
|---|---|---|
| Intragranular | | |
| Rilpivirine HCl | 27.50 | 9.2 |
| Lactose Monohydrate | 55.10 | 18.4 |
| Polysorbate 20 | 0.35 | 0.12 |
| Povidone K29/32 | 3.25 | 1.1 |
| Croscarmellose sodium | 1.10 | 0.37 |
| Extragranular | | |
| Lactose Monohydrate | 134.70 | 44.9 |
| Croscarmellose sodium | 15.00 | 5.0 |
| Microcrystalline cellulose | 60.00 | 20.0 |
| Magnesium stearate | 3.00 | 1.0 |
| Total Rilpivirine Layer Weight (mg) | 300 | 100 |

| Emtricitabine/tenofovir alafenamide hemifumarate Layer | Weight (mg) | % w/w (in layer) |
|---|---|---|
| Intragranular | | |
| Emtricitabine | 199.99 | 57.1 |
| Tenofovir alafenamide hemifumarate | 28.04 | 8.01 |
| Croscarmellose sodium | 28.00 | 8.0 |
| Microcrystalline cellulose | 88.69 | 25.3 |
| Magnesium stearate | 2.60 | 0.75 |
| Extragranular | | |
| Magnesium stearate | 2.60 | 0.75 |
| Total Emtricitabine/ tenofovir alafenamide hemifumarate Layer Weight | 350 | 100 |
| Total Core Tablet Weight | 650 | |
| Opadry II 85F17636 Gray | 19.5 | |

Example 13—Stability Studies

Three batches of tablet E were tested. The results meet release and stability criteria and are shown in the table below and in FIG. 7:

| Analytical Test | Criteria | Batch 1 | Batch 2 | Batch 3 |
|---|---|---|---|---|
| Assay | 95-110% | FTC: 101.8%<br>TAF: 100.9%<br>RPV: 100.5% | FTC: 100.2%<br>TAF: 99.4%<br>RPV: 99.1% | FTC: 99.1%<br>TAF: 98.9%<br>RPV: 98.8% |
| Content Uniformity (RSD, AV) | USP<905> | FTC: 1.4%, 3.7<br>TAF: 1.5%, 3.6<br>RPV: 0.7%, 1.7 | FTC: 1.5%, 3.6<br>TAF: 1.5%, 3.6<br>RPV: 1.3%, 3.1 | FTC: 1.0%, 2.3<br>TAF: 1.4%, 3.3<br>RPV: 2.1%, 5.0 |
| Water Content | Record | 2.9% | 2.7% | 2.8% |

-continued

| | | | | |
|---|---|---|---|---|
| Emtricitabine Degradation | NMT 0.5% | 0.0% | 0.0% | 0.0% |
| Tenofovir alafenamide hemifumarate Degradation | | | | |
| PMPA | NMT 2.50% | 0.26% | 0.19% | 0.27% |
| PMPA Anhydride | NMT 1.00% | Trace | Trace | 0.11% |
| Monophenyl PMPA | NMT 1.50% | ND | ND | ND |
| PMPA Monoamidate | NMT 1.00% | ND | ND | ND |
| Phenol | NMT 1.00% | Trace | Trace | Trace |
| Unspecified TAF Related | NMT 0.50% | ND | ND | ND |
| Total TAF Related | NMT 3.5% | 0.3% | 0.2% | 0.4% |
| Rilpivirine HCl Degradation | NMT 1.0% | 0.0% | 0.0% | 0.0% |

Trace = <0.10%;
ND = Not Detected (<0.05%)

Figure 7:
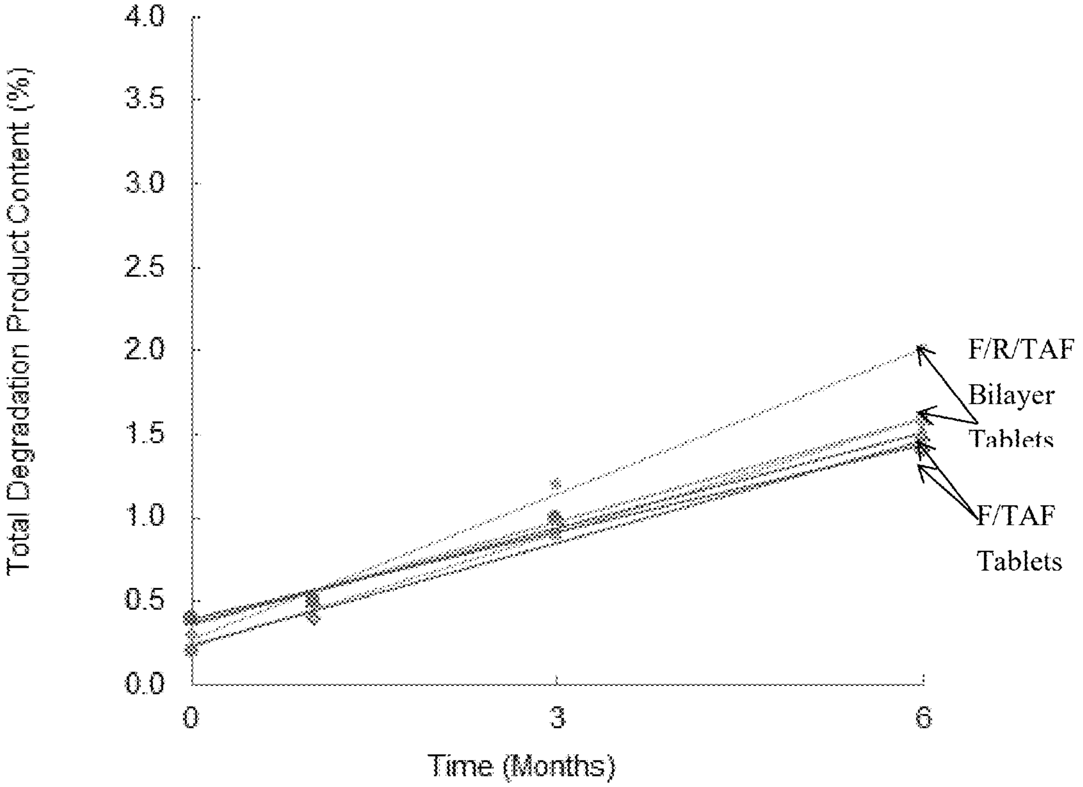
FIG. 7 shows the total tenofovir alafenamide hemifumarate degradation products of various tablets containing rilpivirine HCl, emtricitabine and tenofovir alafenamide hemifumarate, relative to the tenofovir alafenamide hemifumarate degradation products from a tablet containing only emtricitabine and tenofovir alafenamide hemifumarate as active pharmaceutical ingredients.

The stability of Batches 1, 2 and 3 (table above) (assessed in terms of total tenofovir alafenamide degradation products) of rilpivirine HCl/emtricitabine/tenofovir alafenamide hemifumarate tablets is shown relative to that of emtricitabine 200 mg/tenofovir alafenamide hemifumarate 25 mg tablets (assessed at 40° C./75% RH) in FIG. 7.

Figure 8A:
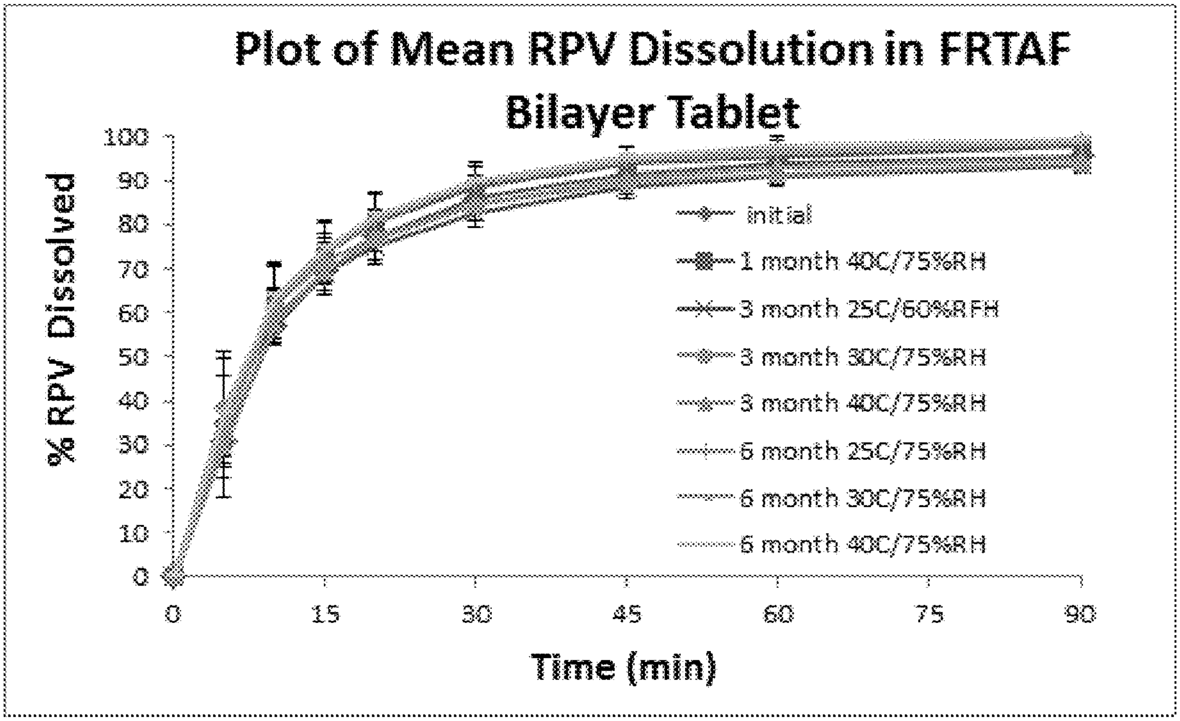
FIGS. 8A, B and C show the results of studies carried out on a bilayer tablet formulation to assess whether the dissolution of rilpivirine HCl, emtricitabine and tenofovir alafenamide hemifumarate, respectively, changes following storage of the tablet for 1 month, 3 months and 6 months under differing conditions.
Figure 8B:
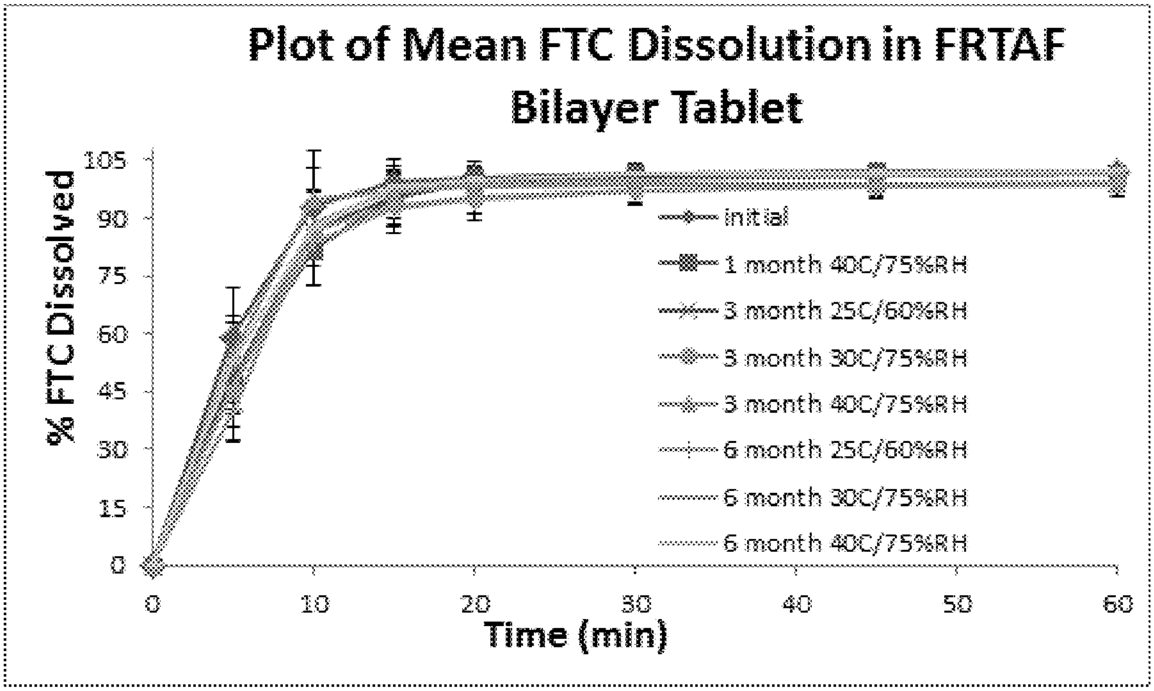
Figure 8C:
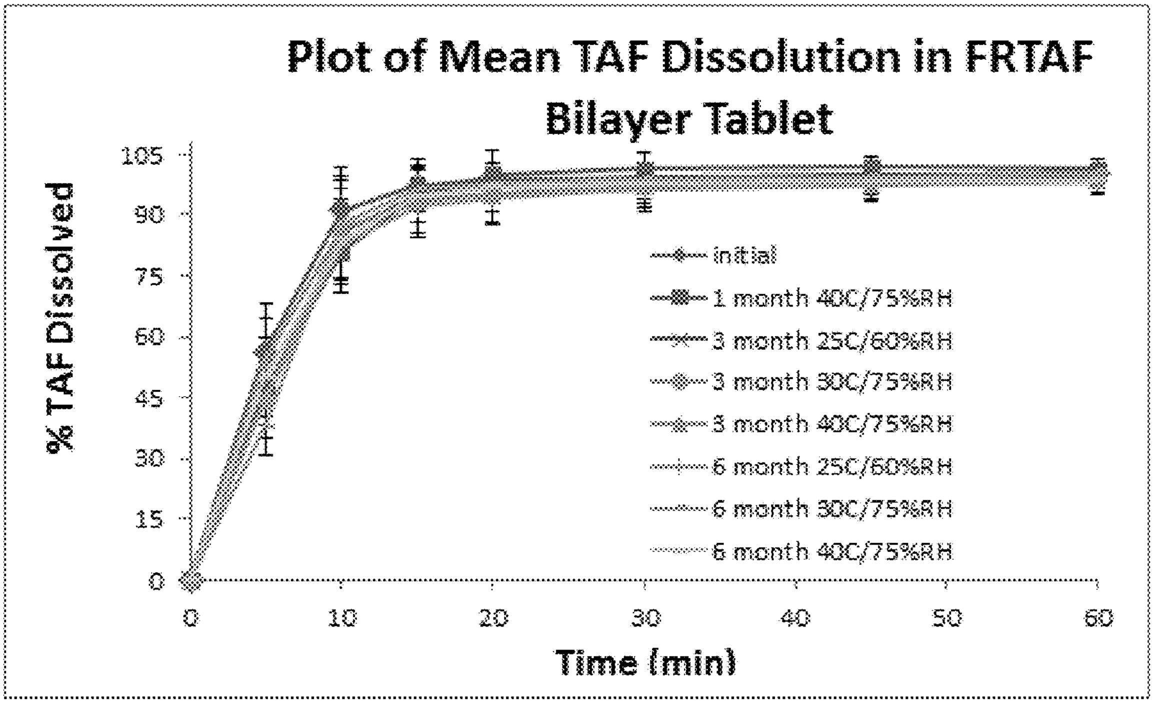

It was also observed that the dissolution of rilpivirine HCl, emtricitabine and tenofovir alafenamide hemifumarate from tablet E did not change following storage of the tablet for 1, 3 and 6 months under varying temperature and humidity conditions (see FIGS. 8A-C). Dissolution of rilpivirine HCl in these studies was monitored using USP Apparatus II, in 1000 ml of 0.01N HCl with 0.5% polysorbate 20, at 37° C. and paddle speed of 75 rpm. Dissolution of emtricitabine and tenofovir alafenamide hemifumarate was monitored using USP apparatus II, in 500 ml of 50 mM sodium citrate pH 5.5, at 37° C. and paddle speed of 75 rpm.

However, the stability of tenofovir alafenamide hemifumarate is sensitive to the water content of the tablet, as shown in the following table, which shows the total degradation of tenofovir alafenamide hemifumarate (Tablet E formulation) at 40° C./75% RH at time zero, 1 month, 3 months and 6 months as a function of the initial water content of the tablet:

| | | | Total tenofovir alafenamide (TAF) hemifumarate Degradation Products (%) | | | | | | | |
|---|---|---|---|---|---|---|---|---|---|---|
| Study Lot Number | Time (months) | Water Content by KF (%) | PMPA | PMPA Anhydride | Monophenyl PMPA | PMPA Monoamidate | Phenol | Total (TAF) hemifumarate Deg. Products (%) | Total emtricitabine Degradation Products (%) | Total rilpivirine HCl Degradation Products (%) |
| AAA | 0 | 2.9 | 0.24 | trace | trace | trace | 0.24 | 0.5 | 0.0 | 0.0 |
| | 1 | 2.3 | 0.35 | 0.13 | trace | trace | 0.21 | 0.7 | 0.0 | 0.0 |
| | 3 | 2.3 | 0.57 | 0.28 | trace | trace | 0.23 | 1.1 | 0.0 | 0.0 |
| | 6 | 2.4 | 0.81 | 0.47 | trace | ND | 0.41 | 1.7 | 0.0 | 0.0 |
| BBB | 0 | 3.5 | 0.25 | trace | trace | trace | 0.23 | 0.5 | 0.0 | 0.0 |
| | 1 | 2.6 | 0.46 | 0.16 | trace | trace | 0.26 | 0.9 | 0.0 | 0.0 |
| | 3 | 2.5 | 0.80 | 0.42 | trace | trace | 0.34 | 1.6 | 0.0 | 0.0 |
| | 6 | 2.6 | 1.12 | 0.67 | trace | ND | 0.53 | 2.3 | 0.0 | 0.0 |
| CCC | 0 | 4.0 | 0.26 | trace | trace | trace | 0.23 | 0.5 | 0.0 | 0.0 |
| | 1 | 2.7 | 0.55 | 0.21 | trace | trace | 0.29 | 1.1 | 0.0 | 0.0 |
| | 3 | 2.6 | 0.96 | 0.58 | trace | trace | 0.41 | 1.9 | 0.0 | 0.0 |
| | 6 | 2.7 | 1.47 | 0.93 | 0.10 | ND | 0.63 | 3.1 | 0.0 | 0.0 |
| DDD | 0 | 4.6 | 0.26 | trace | trace | trace | 0.24 | 0.5 | 0.0 | 0.0 |
| | 1 | 2.7 | 0.68 | 0.26 | trace | trace | 0.34 | 1.3 | 0.0 | 0.0 |
| | 3 | 2.8 | 1.28 | 0.78 | trace | trace | 0.52 | 2.6 | 0.0 | 0.0 |
| | 6 | 2.8 | 2.06 | 1.28 | 0.14 | ND | 0.79 | 4.3 | 0.0 | 0.0 |

As for the emtricitabine and tenofovir alafenamide hemifumarate tablets described above, the stability of tenofovir alafenamide hemifumarate in batches of tablet E packaged with varying levels of desiccant was also investigated. The data are shown in the table below.

| | Tablet E | | | | |
|---|---|---|---|---|---|
| Condition: 40° C./ | Batch X Timepoint (months) | | | Batch Y | |
| 75% RH | 0 | 1 | 3 | 1 | 3 |
| Desiccant amount | N/A | 1 g | | 3 g | |
| Water Content (%) | 2.6 | 2.4 | 2.4 | 2.2 | 2.1 |
| Tenofovir alafenamide hemifumarate Label Strength (%) | 100.4 | 100.9 | 99.2 | 101.2 | 99.5 |
| Tenofovir alafenamide hemifumarate Degradation Products (%) | | | | | |
| PMPA | 0.27 | 0.49 | 0.88 | 0.37 | 0.56 |
| PMPA anhydride | trace | 0.18 | 0.42 | 0.14 | 0.26 |
| Monophenyl PMPA | ND | ND | trace | ND | trace |
| PMPA Monoamidate | ND | trace | trace | trace | trace |
| Phenol | ND | 0.17 | ND | 0.10 | ND |
| Unspecified | ND | ND | 0.12 | ND | trace |
| Total tenofovir alafenamide hemifumarate Degradation Content (%) | 0.3 | 0.8 | 1.4 | 0.6 | 0.8 |

Example 14—Rilpivirine HCl/Emtricitabine/Tenofovir Alafenamide Hemifumarate Bioequivalence Studies A randomized, open-label, single-dose, 3-way, 6-sequence, crossover study was performed to determine the bioequivalence of emtricitabine and tenofovir alafenamide hemifumarate, administered as elvitegravir, cobicistat, emtricitabine, and tenofovir alafenamide hemifumarate (E/C/F/TAF) fixed-dose combination tablet or as rilpivirine HCl/emtricitabine/tenofovir alafenamide hemifumarate fixed-dose combination tablet (tablet E), and the bioequivalence of rilpivirine HCl administered as rilpivirine HCl single tablet or as rilpivirine HCl/emtricitabine/tenofovir alafenamide hemifumarate fixed-dose combination tablet (tablet E).

Duration of Treatment

Three single doses of (a) emtricitabine/rilpivirine/tenofovir alafenamide fixed-dose combination tablet (200/25/25 mg)-tablet E; (b) EDURANT® (rilpivirine, 25 mg, present as 27.5 mg rilpivirine HCl in the tablet) or (c) elvitegravir, cobicistat, emtricitabine, and tenofovir alafenamide (E/C/F/TAF) (150/150/200/10 mg, wherein the tenofovir alafenamide is present as 11.2 mg tenofovir alafenamide hemifumarate in the tablet) fixed-dose combination tablet were administered orally under fed conditions during up to 53 days total study duration.

Criteria for Evaluation

The following plasma pharmacokinetic parameters were calculated: $C_{max}$, $T_{max}$, $C_{last}$, $t_{1/2}$, $AUC_{last}$, $AUC_{inf}$, % $AUC_{exp}$, $V_z/F$, CL/F.

Statistical Methods

Pharmacokinetics: Plasma concentrations and PK parameters were listed and summarized by analyte and treatment group using descriptive statistics. In addition, a parametric analysis of variance using a mixed-effects model appropriate for a crossover design was fitted to the natural logarithmic transformation of the PK parameters ($AUC_{inf}$, $AUC_{last}$, and $C_{max}$). Two-sided 90% confidence intervals (CIs) were constructed for the ratio of geometric least-squares means (GLSMs) of each PK parameter for emtricitabine, rilpivirine HCl, and tenofovir alafenamide hemifumarate. Bioequivalence of emtricitabine, rilpivirine HCl, and tenofovir alafenamide hemifumarate in the rilpivirine HCl/emtricitabine/tenofovir alafenamide hemifumarate fixed-dose combination (tablet E) to the emtricitabine, rilpivirine HCl, and tenofovir alafenamide hemifumarate components in rilpivirine HCl or elvitegravir, cobicistat, emtricitabine, and tenofovir alafenamide hemifumarate fixed-dose combination was concluded if the 90% CI of the GLSM (geometric least-squares mean) ratio of the pharmacokinetic parameters for each analyte between formulations fell within the prespecified bioequivalence boundary of 80% to 125%.

Results

Subject Disposition and Demographics:

A total of 96 subjects were randomized and received at least 1 dose of study drug.

Pharmacokinetics Results: Statistical comparisons of the plasma rilpivirine HCl, emtricitabine and tenofovir alafenamide hemifumarate PK parameters $AUC_{last}$, $AUC_{inf}$, and $C_{max}$ are presented below:

| Emtricitabine PK Parameter | N | Tablet E Test Mean (CV %) | N | Reference Mean (CV %) | GLSM Ratio (Test/ Reference) (%) | 90% CI (%) |
|---|---|---|---|---|---|---|
| Emtricitabine/Rilpivirine HCl/tenofovir alafenamide hemifumarate (200/25/25 mg by weight free base) (Test) vs elvitegravir, cobicistat, emtricitabine, and tenofovir alafenamide hemifumarate (150/150/200/10 mg by weight free base) (Reference) | | | | | | |
| $AUC_{last}$ (h · ng/mL) | 95 | 9381.9 (21.7) | 96 | 10159.4 (21.5) | 92.24 | 90.84, 93.67 |
| $AUC_{inf}$ (h · ng/mL) | 95 | 9603.2 (21.6) | 96 | 10387.1 (21.5) | 92.37 | 90.93, 93.83 |
| $C_{max}$ (ng/mL) | 95 | 1608.6 (26.5) | 96 | 1583.8 (23.8) | 100.81 | 97.52, 104.21 |

| Rilpivirine HCl PK Parameter | N | Tablet E Test Mean (CV %) | N | Reference Mean (CV %) | GLSM Ratio (Test/ Reference) (%) | 90% CI (%) |
|---|---|---|---|---|---|---|
| Emtricitabine/Rilpivirine HCl/tenofovir alafenamide hemifumarate (200/25/25 mg by weight free base) (Test) vs Rilpivirine HCl (25 mg by weight free base) (Reference) | | | | | | |
| $AUC_{last}$ (h · ng/mL) | 95 | 3698.6 (34.9) | 95 | 3373.4 (40.0) | 111.70 | 106.31, 117.38 |
| $AUC_{inf}$ (h · ng/mL) | 95 | 3843.1 (36.2) | 95 | 3540.7 (43.0) | 110.51 | 105.82, 115.42 |
| $C_{max}$ (ng/mL) | 95 | 121.4 (26.1) | 95 | 108.0 (28.7) | 113.52 | 108.40, 118.89 |

| Tenofovir alafenamide hemifumarate PK Parameter | N | Tablet E Test Mean (CV %) | N | Reference Mean (CV %) | GLSM Ratio (Test/ Reference) (%) | 90% CI (%) |
|---|---|---|---|---|---|---|

-continued

| Emtricitabine/rilpivirine HCl/tenofovir alafenamide hemifumarate (200/25/25 mg by weight free base) (Test) vs elvitegravir, cobicistat, emtricitabine, and tenofovir alafenamide hemifumarate (150/150/200/10 mg by weight free base) (Reference) | | | | | | |
|---|---|---|---|---|---|---|
| $AUC_{last}$ (h · ng/mL) | 95 | 250.0 (43.4) | 96 | 238.4 (36.5) | 102.85 | 98.18, 107.75 |
| $AUC_{inf}$ (h · ng/mL) | 82 | 263.6 (42.0) | 85 | 247.4 (36.1) | 103.85 | 98.27, 109.74 |
| $C_{max}$ (ng/mL) | 95 | 198.0 (57.7) | 96 | 191.5 (48.2) | 100.78 | 91.63, 110.85 |

The GLSM ratios and corresponding 90% CIs of $AUC_{last}$, $AUC_{inf}$, and $C_{max}$ for emtricitabine, rilpivirine, and tenofovir alafenamide were contained within the 80% to 125% boundary criteria specified for bioequivalence.

These values were calculated based on the data presented below for each active.

Emtricitabine

The following table shows the summary statistics of the emtricitabine pharmacokinetic parameters:

| Emtricitabine PK Parameter[a] | Tablet E Emtricitabine/rilpivirine HCl/tenofovir alafenamide hemifumarate (Treatment A) (N = 95) | Elvitegravir, cobicistat, emtricitabine, and tenofovir alafenamide hemifumarate (Treatment C) (N = 96) |
|---|---|---|
| $AUC_{last}$ (h · ng/mL) | 9381.9 (21.7) | 10159.4 (21.5) |
| $AUC_{inf}$ (h · ng/mL) | 9603.2 (21.6) | 10387.1 (21.5) |
| $C_{max}$ (ng/mL) | 1608.6 (26.5) | 1583.8 (23.8) |
| $T_{max}$ (h) | 2.00 (1.50, 3.00) | 2.00 (2.00, 3.00) |
| $t_{1/2}$ (h) | 18.71 (15.05, 25.27) | 18.90 (15.89, 26.43) |
| CL/F (L/h) | 21.7 (19.8) | 20.1 (19.6) |
| Vz/F (L) | 650.0 (43.5) | 622.9 (43.5) |

[a]Data are mean (% CV), except $T_{max}$ and $t_{1/2}$, which are reported as median (Q1, Q3).

The following table shows statistical comparisons of emtricitabine pharmacokinetic parameters of $AUC_{last}$, $AUC_{inf}$, and $C_{max}$ (when administered as emtricitabine/rilpivirine HCl/tenofovir alafenamide hemifumarate (tablet E) or elvitegravir, cobicistat, emtricitabine, and tenofovir alafenamide hemifumarate E/C/F/TAF):

| Emtricitabine PK Parameter | N | Tablet E Test GLSM | N | Reference GLSM | GLSM Ratio (Test/Reference) (%) | 90% CI (%) |
|---|---|---|---|---|---|---|
| Emtricitabine/rilpivirine HCl/tenofovir alafenamide hemifumarate (200/25/25 mg by weight free base) (Test) vs elvitegravir, cobicistat, emtricitabine, and tenofovir alafenamide hemifumarate (150/150/200/10 mg by weight free base) (Reference) | | | | | | |
| $AUC_{last}$ (h · ng/mL) | 95 | 9112.91 | 96 | 9879.18 | 92.24 | 90.84, 93.67 |
| $AUC_{inf}$ (h · ng/mL) | 95 | 9316.60 | 96 | 10085.96 | 92.37 | 90.93, 93.83 |
| $C_{max}$ (ng/mL) | 95 | 1534.56 | 96 | 1522.22 | 100.81 | 97.52, 104.21 |

Rilpivirine HCl

The following table provides a summary of the rilpivirine HCl pharmacokinetic parameters following administration of Rilpivirine HCl/emtricitabine/tenofovir alafenamide hemifumarate (tablet E) or rilpivirine HCl:

| Rilpivirine HCl PK Parameter[a] | Tablet E Emtricitabine/rilpivirine HCl/tenofovir alafenamide hemifumarate (Treatment A) (N = 95) | Rilpivirine HCl (Treatment B) (N = 95) |
|---|---|---|
| $AUC_{last}$ (h · ng/mL) | 3698.6 (34.9) | 3373.4 (40.0) |
| $AUC_{inf}$ (h · ng/mL) | 3843.1 (36.2) | 3540.7 (43.0) |
| $C_{max}$ (ng/mL) | 121.4 (26.1) | 108.0 (28.7) |
| $T_{max}$ (h) | 4.00 (4.00, 5.00) | 4.00 (4.00, 5.00) |
| $t_{1/2}$ (h) | 51.65 (36.83, 66.88) | 52.51 (39.29, 66.79) |
| CL/F (L/h) | 7.2 (30.9) | 8.1 (36.6) |
| Vz/F (L) | 546.1 (40.5) | 600.4 (33.6) |

[a]Data are mean (% CV), except $T_{max}$ and $t_{1/2}$, which are reported as median (Q1, Q3).

The following table shows statistical comparisons of rilpivirine HCl pharmacokinetic parameters of $AUC_{last}$, $AUC_{inf}$, and $C_{max}$ (when administered as rilpivirine HCl/emtricitabine/tenofovir alafenamide hemifumarate (tablet E) or rilpivirine HCl):

| Rilpivirine HCl PK Parameter | N | Tablet E Test GLSM | N | Reference GLSM | GLSM Ratio (Test/ Reference) (%) | 90% CI (%) |
|---|---|---|---|---|---|---|
| Emtricitabine/rilpivirine HCl/tenofovir alafenamide hemifumarate (200/25/25 mg by weight free base) (Test) vs rilpivirine HCl (25 mg by weight free base) (Reference) | | | | | | |
| $AUC_{last}$ (h · ng/mL) | 95 | 3510.57 | 95 | 3142.72 | 111.70 | 106.31, 117.38 |
| $AUC_{inf}$ (h · ng/mL) | 95 | 3637.96 | 95 | 3291.86 | 110.51 | 105.82, 115.42 |
| $C_{max}$ (ng/mL) | 95 | 117.48 | 95 | 103.48 | 113.52 | 108.40, 118.89 |

Tenofovir Alafenamide Hemifumarate

The following table shows the summary statistics of the tenofovir alafenamide hemifumarate pharmacokinetic parameters:

| Tenofovir alafenamide hemifumarate PK Parameter[a] | Tablet E Emtricitabine/ rilpivirine HCl/tenofovir alafenamide hemifumarate (Treatment A) (N = 95) | Elvitegravir, cobicistat, emtricitabine, and tenofovir alafenamide hemifumarate (Treatment C) (N = 96) |
|---|---|---|
| $AUC_{last}$ (h · ng/mL) | 250.0 (43.4) | 238.4 (36.5) |
| $AUC_{inf}$ (h · ng/mL) | 263.6 (42.0) | 247.4 (36.1) |
| $C_{max}$ (ng/ml) | 198.0 (57.7) | 191.5 (48.2) |
| $T_{max}$ (h) | 1.50 (1.00, 2.00) | 1.50 (1.00, 2.00) |
| $t_{1/2}$ (h) | 0.42 (0.39, 0.49) | 0.41 (0.37, 0.48) |
| CL/F (L/h) | 109.4 (35.9) | 45.8 (36.2) |
| Vz/F (L) | 72.0 (45.0) | 28.7 (43.6) |

[a]Data are mean (% CV), except $T_{max}$ and $t_{1/2}$, which are reported as median (Q1, Q3). For $AUC_{inf}$, $t_{1/2}$, CL/F, and Vz/F: n = 82 for Treatment A and n = 85 for Treatment C.

The following table shows statistical comparisons of tenofovir alafenamide pharmacokinetic parameters of $AUC_{last}$, $AUC_{inf}$, and $C_{max}$ (when administered as emtricitabine/rilpivirine HCl/tenofovir alafenamide hemifumarate (tablet E) or elvitegravir, cobicistat, emtricitabine, and tenofovir alafenamide hemifumarate):

| Tenofovir alafenamide hemifumarate PK Parameter | N | Tablet E Test GLSM | N | Reference GLSM | GLSM Ratio (Test/ Reference) (%) | 90% CI (%) |
|---|---|---|---|---|---|---|
| Emtricitabine/rilpivirine HCl/tenofovir alafenamide hemifumarate (200/25/25 mg by weight free base) (Test) vs elvitegravir, cobicistat, emtricitabine, and tenofovir alafenamide hemifumarate (150/150/200/10 mg by weight free base) (Reference) | | | | | | |
| $AUC_{last}$ (h · ng/mL) | 95 | 228.27 | 96 | 221.94 | 102.85 | 98.18, 107.75 |
| $AUC_{inf}$ (h · ng/mL) | 82 | 234.87 | 85 | 226.18 | 103.85 | 98.27, 109.74 |
| $C_{max}$ (ng/mL) | 95 | 177.98 | 96 | 176.60 | 100.78 | 91.63, 110.85 |

These studies demonstrate that:

1. The emtricitabine and tenofovir alafenamide hemifumarate components of the emtricitabine/rilpivirine HCl/tenofovir alafenamide hemifumarate (200/25/25 mg by weight free base) fixed-dose combination (tablet E) are bioequivalent to the elvitegravir, cobicistat, emtricitabine, and tenofovir alafenamide hemifumarate (150/150/200/10 mg by weight free base) fixed-dose combination;
2. The rilpivirine HCl component of the emtricitabine/rilpivirine HCl/tenofovir alafenamide hemifumarate (200/25/25 mg by weight free base) fixed-dose combination (tablet E) is bioequivalent to rilpivirine HCl 25 mg (by weight free base) tablet (EDURANT®).

Example 15—Manufacturing Process

The manufacturing/packaging procedure for rilpivirine HCl/emtricitabine/tenofovir alafenamide hemifumarate tablets is divided into five unit processes:

1. mixing of rilpivirine HCl drug substance with intragranular excipients, fluid-bed granulation, milling, and blending with extragranular excipients to yield the rilpivirine HCl final powder blend;
2. mixing of emtricitabine and tenofovir alafenamide hemifumarate drug substances with intragranular excipients, dry granulation, milling, and blending with extragranular excipients to yield emtricitabine/tenofovir alafenamide hemifumarate final powder blend;
3. tablet compression to yield bilayer tablet cores;
4. tablet film-coating to yield film-coated tablets; and
5. packaging.

The manufacturing process steps to produce the final drug product are detailed below.

Rilpivirine HCl Final Powder Blend (Dispensing, Blending, Wet Granulation, Milling, Final Blending)

1. Weigh rilpivirine HCl and the excipients (lactose monohydrate and croscarmellose sodium). Correct the weight of rilpivirine HCl based on the drug content factor (DCF), with a concomitant reduction in the weight of lactose monohydrate.
2. Weigh purified water, polysorbate 20, and polyvinyl pyrollidone. Mix to form the granulation binder fluid until fully dissolved.
3. Add rilpivirine HCl, lactose monohydrate, and croscarmellose sodium to the fluid-bed granulator/dryer and fluidize to pre-mix the components.

4. Spray the entire volume of binder solution while maintaining powder bed fluidization.
5. Dry the granules.
6. Mill the granules using a rotating impeller screening mill.
7. Add the dried, milled granules as well as extragranular lactose monohydrate, microcrystalline cellulose, and croscarmellose sodium and blend in a blender.
8. Add extragranular magnesium stearate and blend.

Emtricitabine/Tenofovir Alafenamide Hemifumarate Final Powder Blend (Dispensing, Blending, Dry Granulation, Milling, Final Blending)

9. Weigh emtricitabine and tenofovir alafenamide hemifumarate drug substances and excipients (microcrystalline cellulose and croscarmellose sodium). Adjust the weight of emtricitabine and tenofovir alafenamide hemifumarate drug substances based on their corresponding DCF, with a concomitant adjustment to the weight of microcrystalline cellulose.
10. Blend in emtricitabine and tenofovir alafenamide hemifumarate drug substance, microcrystalline cellulose, and croscarmellose sodium to a tumble blender and blend.
11. Blend in intragranular portion of magnesium stearate to the tumble blender and blend.
12. Dry granulate the resulting blend using a roller compactor
13. Blend in the extragranular portion of magnesium stearate.

Tableting

14. Compress the rilpivirine HCl final powder blend as the first layer and the emtricitabine/tenofovir alafenamide hemifumarate final powder blend as the second layer to a target rilpivirine HCl layer weight of 300 mg using a target total tablet weight of 650 mg with an appropriate main compression force to achieve a target hardness of 16 kP (range: 13 to 19 kP).

Film-Coating

15. Prepare a suspension of Opadry® II Gray 85F17636. Film-coat the tablet cores to achieve the target tablet weight gain of 3% (range 2-4%). Dry film-coated tablets prior to cooling and discharge.

Figure 9:
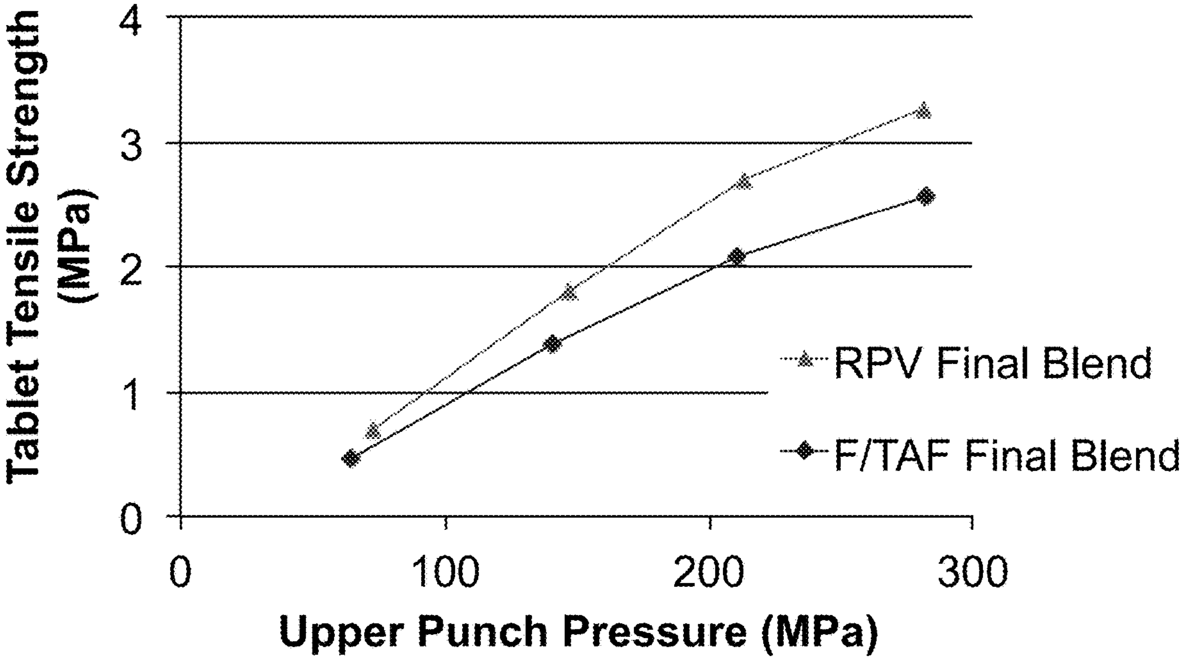
FIG. 9 shows the tensile strength of the individual rilpivirine HCl and emtricitabine/tenofovir alafenamide hemifumarate powder blends as a function of upper punch pressure.

It was observed that the layer order in tabletting has an impact on compressibility and flow, hence why rilpivirine HCl selected as layer 1. FIG. 9 shows the tensile strength of the tablet as a function of upper punch pressure in the final blends of rilpivirine HCl and emtricitabine/tenofovir alafenamide hemifumarate.

A hardness range of 13-19 kP with target of 16 kP selected to optimize friability, based on studies carried out to assess the impact of tablet hardness on friability reported in the following table:

| Tamp Force (N) | Main Compression Force (kN) | Hardness (kp)[a] | Observations During Hardness Testing | Friability (%) | Observations During Friability Testing |
|---|---|---|---|---|---|
| 800 | 11.3 | 10.8 | None | 0.0 | Edge wear |
| 800 | 12.7 | 11.7 | None | 0.0 | Slight edge wear |
| 800 | 15.0 | 14.4 | None | 0.0 | None |
| 800 | 20.0 | 20.3 | None | 0.0 | None |
| 800 | 21.7 | 20.5 | None | 0.0 | None |
| 800 | 25.0 | 20.9 | Capping on layer 1 observed for 5 of 9 tablets | 0.08 | Capping on layer 1 observed for 1 of 10 tablets |

[a]Average value of five to nine tablets

Example 16—Long Term Stability Studies

The long term stability of Tablets C and D was measured over the course of 12 months at 30° C./75% relative humidity (RH). The results of those studies are provided in the following tables:

Tablet C (200 mg Emtricitabine/10 mg Tenofovir Alafenamide)

| | | | Total tenofovir alafenamide (TAF) hemifumarate Degradation (Deg.) Products (%) | | | | | | |
|---|---|---|---|---|---|---|---|---|---|
| Batch | Timepoint (months) | Water Content by KF (%) | PMPA | PMPA Anhydride | Monophenyl PMPA | PMPA Monoamidate | Phenol | Total (TAF) hemifumarate Deg. Products (%) | Total emtricitabine Degradation Products (%) |
| 1 | 0 | 1.3 | 0.21 | 0.19 | — | trace | — | 0.4 | 0.0 |
| | 3 | 1.1 | 0.27 | 0.20 | — | 0.1 | — | 0.6 | 0.0 |
| | 9 | 1.1 | 0.52 | 0.42 | — | 0.15 | 0.18 | 1.3 | 0.0 |
| | 12 | 0.9 | 0.54 | 0.46 | — | 0.15 | 0.22 | 1.4 | 0.0 |
| 2 | 0 | 1.3 | 0.19 | Trace | — | trace | — | 0.2 | 0.0 |
| | 3 | 0.9 | 0.27 | 0.13 | — | 0.1 | — | 0.5 | 0.0 |
| | 9 | 1.0 | 0.53 | 0.39 | — | 0.14 | 0.19 | 1.3 | 0.0 |
| | 12 | 0.9 | 0.54 | 0.46 | trace | 0.15 | 0.23 | 1.4 | 0.0 |
| 3 | 0 | 1.2 | 0.26 | 0.11 | — | trace | — | 0.4 | 0.0 |
| | 3 | 0.9 | 0.30 | 0.14 | — | 0.10 | — | 0.5 | 0.0 |
| | 9 | 1.0 | 0.53 | 0.35 | — | 0.13 | 0.16 | 1.2 | 0.0 |
| | 12 | 0.8 | 0.54 | 0.39 | — | 0.14 | 0.19 | 1.4 | 0.0 |

| Tablet D (200 mg Emtricitabine/25 mg Tenofovir Alafenamide) | | | | | | | | | | |
|---|---|---|---|---|---|---|---|---|---|---|
| | | | Total tenofovir alafenamide (TAF) hemifumarate Degradation Products (%) | | | | | | | |
| Batch | Time (months) | Water Content by KF (%) | PMPA | PMPA Anhydride | Monophenyl PMPA | PMPA Monoamidate | Phenol | Total (TAF) hemifumarate Deg. Products (%) | Total emtricitabine Degradation |
| 1 | 0 | 1.1 | 0.21 | 0.19 | — | trace | — | 0.4 | 0.0 |
| | 3 | 0.8 | 0.28 | 0.17 | — | 0.16 | trace | 0.6 | 0.0 |
| | 9 | 0.9 | 0.39 | 0.29 | — | trace | 0.11 | 0.8 | 0.0 |
| | 12 | 0.7 | 0.40 | 0.30 | — | trace | 0.16 | 0.9 | 0.0 |
| 2 | 0 | 0.9 | 0.17 | trace | — | trace | — | 0.2 | 0.0 |
| | 3 | 0.8 | 0.24 | trace | — | 0.15 | 0.21 | 0.6 | 0.0 |
| | 9 | 0.9 | 0.35 | 0.20 | — | trace | 0.13 | 0.7 | 0.0 |
| | 12 | 0.8 | 0.38 | 0.24 | trace | trace | 0.17 | 0.8 | 0.0 |
| 3 | 0 | 0.9 | 0.26 | 0.11 | — | trace | — | 0.4 | 0.0 |
| | 1 | 0.9 | 0.31 | 0.11 | — | 0.14 | — | 0.6 | 0.0 |
| | 3 | 0.8 | 0.42 | 0.21 | — | trace | 0.10 | 0.7 | 0.0 |
| | 6 | 0.8 | 0.41 | 0.23 | — | trace | 0.14 | 0.8 | 0.0 |

These results demonstrate that TAF in the tenofovir alafenamide hemifumarate tablets (packaged in induction sealed, 60 mL HDPE bottles (30 tablets/bottle) with 3 g of desiccant) is stable under long term storage conditions (30° C./75% RH).

All publications, patents and patent applications are incorporated by reference in their entirety, as though individually incorporated by reference. The invention has been described with reference to various specific and preferred embodiments and techniques. However, it should be understood that many variations and modifications may be made while remaining within the spirit and scope of the invention.

The invention claimed is:

1. A method of treating an HIV infection, wherein the method comprises administering to a human a tablet consisting of:

(a) a tablet core consisting of:

25 mg tenofovir alafenamide, or a pharmaceutically acceptable salt thereof, calculated as tenofovir alafenamide free base;

200 mg emtricitabine, or a pharmaceutically acceptable salt thereof, calculated as emtricitabine free base; and one or more excipients selected from a disintegrant, a lubricant, and a filler, or any combination thereof, wherein the one or more excipients do not include starch; and (b) an optional coating;

wherein about 4% to about 12% by weight of the tablet core is the tenofovir alafenamide, or a pharmaceutically acceptable salt thereof; and wherein the tablet contains only two active pharmaceutical ingredients: tenofovir alafenamide, or a pharmaceutically acceptable salt thereof, and emtricitabine, or a pharmaceutically acceptable salt thereof.

2. The method according to claim 1, wherein the tablet contains a pharmaceutically acceptable salt of tenofovir alafenamide, wherein the pharmaceutically acceptable salt is a fumarate salt.

3. The method according to claim 2, wherein less than about 300 mg of the tablet core is the one or more excipients.

4. The method according to claim 2, wherein less than about 250 mg of the tablet core is the one or more excipients.

5. The method according to claim 2, wherein the one or more excipients consist of the disintegrant, the lubricant, and the filler.

6. The method according to claim 5, wherein less than about 40% by weight of the tablet core is the filler.

7. The method according to claim 5, wherein less than about 20% by weight of the tablet core is the disintegrant.

8. The method according to claim 5, wherein about 0.5 w/w % to about 5 w/w % of the tablet core is the lubricant.

9. The method according to claim 5, wherein:

less than about 40% by weight of the tablet core is the filler;

less than about 20% by weight of the tablet core is the disintegrant; and about 0.5 w/w % to about 5 w/w % of the tablet core is the lubricant.

10. The method according to claim 9, wherein the tablet core has a total weight of less than 600 mg.

11. The method according to claim 9, wherein the tablet core has a total weight of less than 500 mg.

12. The method according to claim 2, wherein the one or more excipients are selected from microcrystalline cellulose, croscarmellose sodium, magnesium stearate, lactose, and crospovidone, or any combination thereof.

13. The method according to claim 12, wherein:

less than about 40% by weight of the tablet core is microcrystalline cellulose or lactose;

less than about 20% by weight of the tablet core is croscarmellose sodium or crospovidone; and about 0.5 w/w % to about 5 w/w % of the tablet core is magnesium stearate.

14. The method according to claim 12, wherein the tablet core contains less than 200 mg of the microcrystalline cellulose or less than 200 mg of the lactose.

15. The method according to claim 2, wherein the tablet core has a total weight of less than 600 mg.

16. The method according to claim 15, wherein the one or more excipients are selected from microcrystalline cellulose, croscarmellose sodium, magnesium stearate, lactose, and crospovidone, or any combination thereof.

17. The method according to claim 16, wherein:

less than about 40% by weight of the tablet core is microcrystalline cellulose or lactose;

less than about 20% by weight of the tablet core is croscarmellose sodium or crospovidone; and about 0.5 w/w % to about 5 w/w % of the tablet core is magnesium stearate.

18. The method according to claim 16, wherein the tablet core contains less than 200 mg of the microcrystalline cellulose or less than 200 mg of the lactose.

19. The method according to claim 2, wherein the tablet core has a total weight of less than 500 mg.

20. The method according to claim 19, wherein the one or more excipients are selected from microcrystalline cellulose, croscarmellose sodium, magnesium stearate, lactose, and crospovidone, or any combination thereof.

21. The method according to claim 20, wherein:

less than about 40% by weight of the tablet core is microcrystalline cellulose or lactose;

less than about 20% by weight of the tablet core is croscarmellose sodium or crospovidone; and about 0.5 w/w % to about 5 w/w % of the tablet core is magnesium stearate.

22. The method according to claim 20, wherein the tablet core contains less than 200 mg of the microcrystalline cellulose or less than 200 mg of the lactose.

23. The method according to claim 1, wherein about 7% to about 9% by weight of the tablet core is the tenofovir alafenamide, or a pharmaceutically acceptable salt thereof.

24. The method according to claim 2, wherein the fumarate salt is tenofovir alafenamide hemifumarate.

25. The method according to claim 2, wherein the coating is a polymeric film coating.

26. The method according to claim 25, wherein the polymeric film coating contains polyvinyl alcohol, titanium dioxide, macrogol, and talc.

27. The method according to claim 1, wherein the HIV infection is HIV-1.

28. The method according to claim 1, wherein the term "about" refers to ±5%.

29. The method according to claim 1, wherein the term "about" refers to ±1%.

* * * * *